(12) United States Patent
Wada et al.

(10) Patent No.: US 10,428,019 B2
(45) Date of Patent: *Oct. 1, 2019

(54) CHIRAL AUXILIARIES

(75) Inventors: Takeshi Wada, Chiba (JP); Mamoru Shimizu, Okinawa (JP)

(73) Assignee: WAVE LIFE SCIENCES LTD., Singapore (SG)

( * ) Notice: Subject to any disclaimer, the term of this patent is extended or adjusted under 35 U.S.C. 154(b) by 159 days.

This patent is subject to a terminal disclaimer.

(21) Appl. No.: 13/825,627

(22) PCT Filed: Sep. 22, 2011

(86) PCT No.: PCT/JP2011/071559
§ 371 (c)(1),
(2), (4) Date: Mar. 22, 2013

(87) PCT Pub. No.: WO2012/039448
PCT Pub. Date: Mar. 29, 2012

(65) Prior Publication Data
US 2013/0178612 A1    Jul. 11, 2013

Related U.S. Application Data

(60) Provisional application No. 61/386,016, filed on Sep. 24, 2010.

(51) Int. Cl.

| | | |
|---|---|---|
| C07H 21/02 | (2006.01) | |
| C07H 21/00 | (2006.01) | |
| C07H 19/00 | (2006.01) | |
| C07H 19/04 | (2006.01) | |
| C07H 19/20 | (2006.01) | |
| C07D 221/06 | (2006.01) | |
| C07D 217/22 | (2006.01) | |
| C07D 211/56 | (2006.01) | |
| C07D 211/40 | (2006.01) | |
| C07D 221/18 | (2006.01) | |
| C07D 209/56 | (2006.01) | |
| C09B 7/02 | (2006.01) | |
| C07D 207/12 | (2006.01) | |
| C07D 207/16 | (2006.01) | |
| C07D 211/44 | (2006.01) | |

(Continued)

(52) U.S. Cl.
CPC ......... *C07D 207/12* (2013.01); *C07D 207/16* (2013.01); *C07D 209/62* (2013.01); *C07D 211/42* (2013.01); *C07D 211/44* (2013.01); *C07D 211/62* (2013.01); *C07D 217/24* (2013.01); *C07D 221/10* (2013.01); *C07D 221/18* (2013.01); *C07H 1/00* (2013.01); *C07H 19/06* (2013.01); *C07H 19/16* (2013.01); *C07H 21/00* (2013.01); *C07H 21/02* (2013.01); *C07H 21/04* (2013.01)

(58) Field of Classification Search
CPC ................ C07D 207/16; C07D 207/12; C07D 209/622; C07D 209/62; C07D 211/44; C07D 211/62; C07D 217/24; C07D 221/10; C07D 221/18; C07D 211/42; C07H 21/00; C07H 21/02; C07H 21/04; C07H 1/00; C07H 19/06; C07H 19/16
See application file for complete search history.

(56) References Cited

U.S. PATENT DOCUMENTS 2,878,264 A * 3/1959 Lunsford ............. C07D 207/12
548/541
3,135,766 A    6/1964 Gould
(Continued)

FOREIGN PATENT DOCUMENTS

CN    1688192 A    10/2005
CN    102675386 A    9/2012
(Continued)

OTHER PUBLICATIONS

Takeshi Wada, "Chapter 1 Development of nucleic acid medicines, 3.3 Chemical synthesis of phosphorus atom-modified nucleic acids, CMC Publication", Frontier of Development of Nucleic Acid Medicine, Feb. 2009, pp. 67-75.
(Continued)

*Primary Examiner* — Lawrence E Crane
(74) *Attorney, Agent, or Firm* — Choate, Hall & Stewart LLP; Xiaodong Li; Surin K. Mong

(57) ABSTRACT

The disclosed and claimed compounds are chiral auxiliaries useful for efficiently producing a phosphorus atom-modified nucleic acid derivative with high stereoregularity. The disclosed and claimed compounds include those represented by the following formula (I) or formula (XI) for introducing the chiral auxiliaries.

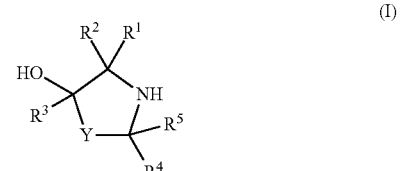

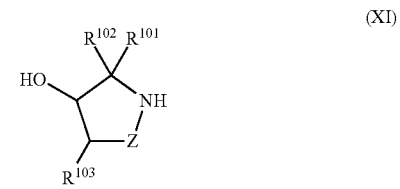

20 Claims, No Drawings

(51) Int. Cl.
*C07D 211/62* (2006.01)
*C07D 217/24* (2006.01)
*C07H 19/06* (2006.01)
*C07H 19/16* (2006.01)
*C07D 209/62* (2006.01)
*C07D 211/42* (2006.01)
*C07D 221/10* (2006.01)
*C07H 1/00* (2006.01)
*C07H 21/04* (2006.01)

(56) References Cited

U.S. PATENT DOCUMENTS

| | | |
|---|---|---|
| 3,484,473 A | 12/1969 | Buckman et al. |
| 3,687,808 A | 8/1972 | Merigan et al. |
| 3,745,162 A * | 7/1973 | Helsley ............... C07D 217/06 546/141 |
| 4,022,791 A * | 5/1977 | Welch, Jr. ............... C07C 45/46 544/130 |
| 4,113,869 A | 9/1978 | Gardner |
| 4,415,732 A | 11/1983 | Caruthers et al. |
| 4,458,066 A | 7/1984 | Caruthers et al. |
| 4,500,707 A | 2/1985 | Caruthers et al. |
| 4,542,142 A | 9/1985 | Martel et al. |
| 4,659,774 A | 4/1987 | Webb et al. |
| 4,663,328 A | 5/1987 | Lafon |
| 4,668,777 A | 5/1987 | Caruthers et al. |
| 4,725,677 A | 2/1988 | Koster et al. |
| 4,735,949 A * | 4/1988 | Domagala ............ C07D 401/04 514/300 |
| 4,840,956 A * | 6/1989 | Domagala ............ C07D 401/04 514/312 |
| 4,845,205 A | 7/1989 | Huynh Dinh et al. |
| 4,923,901 A | 5/1990 | Koester et al. |
| 4,943,629 A | 7/1990 | Devries et al. |
| 4,945,158 A | 7/1990 | Devries et al. |
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| 5,141,813 A | 8/1992 | Nelson |
| 5,151,510 A | 9/1992 | Stec et al. |
| 5,175,273 A | 12/1992 | Bischofberger et al. |
| 5,200,553 A | 4/1993 | Nudelman et al. |
| 5,212,295 A | 5/1993 | Cook |
| 5,223,618 A | 6/1993 | Cook et al. |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,378,825 A | 1/1995 | Cook et al. |
| 5,386,023 A | 1/1995 | Sanghvi et al. |
| 5,432,272 A | 7/1995 | Benner |
| 5,457,187 A | 10/1995 | Gmeiner et al. |
| 5,457,191 A | 10/1995 | Cook et al. |
| 5,459,255 A | 10/1995 | Cook et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,541,307 A | 7/1996 | Cook et al. |
| 5,552,540 A | 9/1996 | Haralambidis |
| 5,565,488 A | 10/1996 | Braunlich et al. |
| 5,576,302 A | 11/1996 | Cook et al. |
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,620,963 A | 4/1997 | Cook et al. |
| 5,622,989 A | 4/1997 | Braunlich et al. |
| 5,623,070 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,677,437 A | 10/1997 | Teng et al. |
| 5,681,940 A | 10/1997 | Wang et al. |
| 5,681,941 A | 10/1997 | Cook et al. |
| 5,688,941 A | 11/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,777,092 A | 7/1998 | Cook et al. |
| 5,783,682 A | 7/1998 | Cook et al. |
| 5,792,844 A | 8/1998 | Sanghvi et al. |
| 5,795,765 A | 8/1998 | Izu et al. |
| 5,808,023 A | 9/1998 | Sanghvi et al. |
| 5,824,503 A | 10/1998 | Kurome et al. |
| 5,834,607 A | 11/1998 | Manoharan et al. |
| 5,846,466 A | 12/1998 | Abe et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,892,024 A | 4/1999 | Chaturvedula et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,965,721 A | 10/1999 | Cook et al. |
| 5,969,118 A | 10/1999 | Sanghvi et al. |
| 5,976,855 A | 11/1999 | Svendsen et al. |
| 5,998,148 A | 12/1999 | Bennett et al. |
| 5,998,602 A | 12/1999 | Torrence et al. |
| 5,998,603 A | 12/1999 | Cook et al. |
| 6,004,813 A | 12/1999 | Serlupi-Crescenzi et al. |
| 6,005,107 A | 12/1999 | Nguyen-Ba et al. |
| 6,015,886 A | 1/2000 | Dale et al. |
| 6,015,887 A | 1/2000 | Teng |
| 6,017,700 A | 1/2000 | Horn et al. |
| 6,025,482 A | 2/2000 | Cook et al. |
| 6,031,092 A | 2/2000 | Just et al. |
| 6,056,973 A | 5/2000 | Allen et al. |
| 6,057,371 A * | 5/2000 | Glennon ............... A61K 31/435 514/649 |
| 6,066,500 A | 5/2000 | Bennett et al. |
| 6,080,543 A | 6/2000 | Engel et al. |
| 6,087,482 A | 7/2000 | Teng et al. |
| 6,107,094 A | 8/2000 | Crooke |
| 6,121,433 A | 9/2000 | Cook et al. |
| 6,124,445 A | 9/2000 | Imbach et al. |
| 6,127,540 A | 10/2000 | Nguyen-Ba et al. |
| 6,133,438 A | 10/2000 | Cook et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,172,209 B1 | 1/2001 | Manoharan et al. |
| 6,191,266 B1 | 2/2001 | Wang |
| 6,194,576 B1 | 2/2001 | Nguyen-Ba et al. |
| 6,207,646 B1 | 3/2001 | Krieg et al. |
| 6,214,551 B1 | 4/2001 | Sanghvi et al. |
| 6,214,805 B1 | 4/2001 | Torrence et al. |

(56) References Cited

U.S. PATENT DOCUMENTS

| | | |
|---|---|---|
| 6,222,025 B1 | 4/2001 | Cook et al. |
| 6,232,463 B1 | 5/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St Clair et al. |
| 6,270,968 B1 | 8/2001 | Dalb.o slashed.ge et al. |
| 6,271,004 B1 | 8/2001 | Warthoe |
| 6,271,357 B1 | 8/2001 | Cook et al. |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,320,040 B1 | 11/2001 | Cook et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,372,492 B1 | 4/2002 | Bennett et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,739 B1 | 8/2002 | Bennett et al. |
| 6,440,943 B1 | 8/2002 | Cook et al. |
| 6,444,656 B1 | 9/2002 | Nguyen-Ba et al. |
| 6,451,524 B1 | 9/2002 | Ecker |
| 6,455,308 B1 | 9/2002 | Freier |
| 6,468,983 B2 | 10/2002 | Silverman et al. |
| 6,495,677 B1 | 12/2002 | Ramasamy et al. |
| 6,500,945 B2 | 12/2002 | Cook |
| 6,506,594 B1 | 1/2003 | Barany et al. |
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,022 B2 | 10/2003 | Michels et al. |
| 6,639,062 B2 | 10/2003 | Manoharan et al. |
| 6,649,750 B1 | 11/2003 | Capaldi et al. |
| 6,670,461 B1 | 12/2003 | Wengel et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,815,542 B2 | 11/2004 | Hong et al. |
| 6,861,518 B2 | 3/2005 | Just et al. |
| 6,867,294 B1 | 3/2005 | Sanghvi et al. |
| 6,900,301 B2 | 5/2005 | Cook et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,030,230 B2 | 4/2006 | Ross et al. |
| 7,045,610 B2 | 5/2006 | Dempcy et al. |
| 7,049,122 B2 | 5/2006 | Chang et al. |
| 7,067,497 B2 | 6/2006 | Hanecak et al. |
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B1 | 4/2007 | Vargeese et al. |
| 7,214,491 B2 | 5/2007 | Yadav et al. |
| 7,227,014 B2 | 6/2007 | Crooke et al. |
| 7,238,795 B2 | 7/2007 | Seela et al. |
| 7,247,621 B2 | 7/2007 | Hong et al. |
| 7,259,150 B2 | 8/2007 | Crooke et al. |
| 7,264,932 B2 | 9/2007 | Latham et al. |
| 7,268,119 B2 | 9/2007 | Cook et al. |
| 7,271,156 B2 | 9/2007 | Krieg et al. |
| 7,285,658 B2 | 10/2007 | Cook et al. |
| 7,288,376 B2 | 10/2007 | Sarma et al. |
| 7,303,895 B1 * | 12/2007 | O'Regan ................ C07K 14/47 435/320.1 |
| 7,304,081 B2 * | 12/2007 | Yao ....................... C07D 207/06 514/370 |
| 7,354,909 B2 | 4/2008 | Klinman et al. |
| 7,381,527 B2 | 6/2008 | Sarma et al. |
| 7,399,845 B2 | 7/2008 | Seth et al. |
| 7,407,943 B2 | 8/2008 | Crooke et al. |
| 7,407,965 B2 | 8/2008 | Chen et al. |
| 7,410,975 B2 | 8/2008 | Lipford et al. |
| 7,414,116 B2 | 8/2008 | Milton et al. |
| 7,425,545 B2 | 9/2008 | Crooke et al. |
| 7,427,672 B2 | 9/2008 | Imanishi et al. |
| 7,429,565 B2 | 9/2008 | Boojamra et al. |
| 7,432,249 B2 | 10/2008 | Crooke |
| 7,432,250 B2 | 10/2008 | Crooke |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,495,088 B1 | 2/2009 | Brakel et al. |
| 7,501,091 B2 | 3/2009 | Munoz et al. |
| 7,507,808 B2 | 3/2009 | Dobie |
| 7,507,811 B2 | 3/2009 | Khvorova et al. |
| 7,511,131 B2 | 3/2009 | Crooke et al. |
| 7,517,520 B2 | 4/2009 | Manolova et al. |
| 7,534,879 B2 | 5/2009 | van Deutekom |
| 7,537,767 B2 | 5/2009 | Bachmann et al. |
| 7,547,684 B2 | 6/2009 | Seth et al. |
| 7,585,847 B2 | 9/2009 | Bratzler et al. |
| 7,598,031 B2 | 10/2009 | Liew |
| 7,598,227 B2 | 10/2009 | Crooke et al. |
| 7,598,230 B2 | 10/2009 | Cook et al. |
| 7,608,594 B2 | 10/2009 | Blagg et al. |
| 7,622,451 B2 | 11/2009 | Blagg et al. |
| 7,629,321 B2 | 12/2009 | Crooke |
| 7,645,747 B2 | 1/2010 | Boojamra et al. |
| 7,662,558 B2 | 2/2010 | Liew |
| 7,666,854 B2 | 2/2010 | Seth et al. |
| 7,666,888 B2 * | 2/2010 | Bartberger ........... C07D 403/06 514/378 |
| 7,683,036 B2 | 3/2010 | Esau et al. |
| 7,695,902 B2 | 4/2010 | Crooke |
| 7,696,345 B2 | 4/2010 | Allerson et al. |
| 7,713,941 B2 | 5/2010 | Cook et al. |
| 7,718,623 B2 | 5/2010 | Kitagawa et al. |
| 7,723,508 B2 | 5/2010 | Crooke et al. |
| 7,732,590 B2 | 6/2010 | Bhanot et al. |
| 7,732,660 B2 | 6/2010 | Helliwell et al. |
| 7,741,305 B2 | 6/2010 | Crooke et al. |
| 7,741,457 B2 | 6/2010 | Seth et al. |
| 7,749,700 B2 | 7/2010 | Baird et al. |
| 7,750,131 B2 | 7/2010 | Seth et al. |
| 7,750,141 B2 | 7/2010 | Crooke et al. |
| 7,750,731 B2 | 7/2010 | Poulsen et al. |
| 7,759,318 B1 | 7/2010 | Perera et al. |
| 7,776,344 B2 | 8/2010 | Hartmann et al. |
| 7,776,874 B2 * | 8/2010 | Yao ....................... C07D 207/06 514/278 |
| 7,777,023 B2 | 8/2010 | Vargeese et al. |
| 7,803,930 B2 | 9/2010 | Crooke et al. |
| 7,807,653 B2 | 10/2010 | Cook et al. |
| 7,807,816 B2 | 10/2010 | Wilton et al. |

(56) References Cited

U.S. PATENT DOCUMENTS

| | | | | |
|---|---|---|---|---|
| 7,811,998 | B2 | 10/2010 | Blagg et al. | |
| 7,812,003 | B2 | 10/2010 | Safe et al. | |
| 7,838,287 | B2 | 11/2010 | Goldsmith et al. | |
| 7,863,252 | B2 | 1/2011 | Crooke et al. | |
| 7,884,086 | B2 | 2/2011 | Bennett et al. | |
| 7,884,117 | B2 * | 2/2011 | Zhang | C07D 487/04 514/378 |
| 7,888,324 | B2 | 2/2011 | Crooke et al. | |
| 7,893,039 | B2 | 2/2011 | Swayze et al. | |
| 7,919,472 | B2 | 4/2011 | Monia et al. | |
| 7,947,658 | B2 | 5/2011 | Aronin et al. | |
| 7,951,934 | B2 | 5/2011 | Freier | |
| 7,960,353 | B2 | 6/2011 | Blagg | |
| 7,960,541 | B2 | 6/2011 | Wilton et al. | |
| 7,973,015 | B2 | 7/2011 | van Ommen et al. | |
| 8,003,619 | B2 | 8/2011 | Hartmann et al. | |
| 8,008,011 | B2 | 8/2011 | Schmutz et al. | |
| 8,008,459 | B2 | 8/2011 | Goldsmith et al. | |
| 8,022,083 | B2 | 9/2011 | Boojamra et al. | |
| 8,039,235 | B2 | 10/2011 | Lin et al. | |
| 8,057,997 | B2 | 11/2011 | Seela et al. | |
| 8,058,288 | B2 * | 11/2011 | Yao | C07D 207/06 514/292 |
| 8,067,173 | B2 | 11/2011 | Liew | |
| 8,076,303 | B2 | 12/2011 | Iyer et al. | |
| 8,084,437 | B2 | 12/2011 | Freier et al. | |
| 8,084,600 | B2 | 12/2011 | Natt et al. | |
| 8,088,582 | B2 | 1/2012 | Sampath et al. | |
| 8,093,222 | B2 | 1/2012 | Freier et al. | |
| 8,093,225 | B2 | 1/2012 | Mamet | |
| 8,101,348 | B2 | 1/2012 | Tuschl et al. | |
| 8,101,358 | B2 | 1/2012 | Liew | |
| 8,101,585 | B2 | 1/2012 | Yu et al. | |
| 8,101,743 | B2 | 1/2012 | Brown-Driver et al. | |
| 8,106,025 | B2 | 1/2012 | Bennett et al. | |
| 8,110,358 | B2 | 2/2012 | Liew | |
| 8,110,558 | B2 | 2/2012 | Bennett et al. | |
| 8,114,597 | B2 | 2/2012 | Liew | |
| 8,124,745 | B2 | 2/2012 | Allerson et al. | |
| 8,133,674 | B2 | 3/2012 | Liew | |
| 8,133,675 | B2 | 3/2012 | Liew | |
| 8,133,876 | B2 | 3/2012 | Bennett et al. | |
| 8,138,328 | B2 | 3/2012 | Crooke et al. | |
| 8,143,230 | B2 | 3/2012 | Bhanot et al. | |
| 8,148,072 | B2 | 4/2012 | Liew | |
| 8,158,598 | B2 | 4/2012 | Bhanot et al. | |
| 8,163,707 | B2 | 4/2012 | Qiu et al. | |
| 8,178,506 | B2 | 5/2012 | Lollo et al. | |
| 8,188,059 | B2 | 5/2012 | Bhanot et al. | |
| 8,206,923 | B2 | 6/2012 | Garza Gonzalez et al. | |
| 8,207,263 | B2 | 6/2012 | Popot et al. | |
| 8,212,011 | B2 | 7/2012 | Blagg | |
| 8,212,012 | B2 | 7/2012 | Blagg | |
| 8,226,759 | B2 | 7/2012 | Shin et al. | |
| 8,232,384 | B2 | 7/2012 | Wilton et al. | |
| 8,257,922 | B2 | 9/2012 | Liew | |
| 8,258,289 | B2 | 9/2012 | Bhanot et al. | |
| 8,350,022 | B2 | 1/2013 | Meier et al. | |
| 8,361,977 | B2 | 1/2013 | Baker et al. | |
| 8,383,660 | B2 * | 2/2013 | Chang | C07D 257/06 514/381 |
| 8,410,070 | B2 | 4/2013 | Miller et al. | |
| 8,415,465 | B2 | 4/2013 | Freier | |
| 8,420,821 | B2 * | 4/2013 | Matsuda | C07C 65/21 546/156 |
| 8,431,693 | B2 | 4/2013 | Manoharan et al. | |
| 8,450,474 | B2 | 5/2013 | Wilton et al. | |
| 8,455,634 | B2 | 6/2013 | Wilton et al. | |
| 8,455,635 | B2 | 6/2013 | Wilton et al. | |
| 8,455,636 | B2 | 6/2013 | Wilton et al. | |
| 8,470,987 | B2 * | 6/2013 | Wada | C07F 9/65586 536/22.1 |
| 8,476,423 | B2 | 7/2013 | Wilton et al. | |
| 8,481,710 | B2 | 7/2013 | Davidson et al. | |
| 8,486,907 | B2 | 7/2013 | Wilton et al. | |
| 8,501,414 | B2 | 8/2013 | Danzer et al. | |
| 8,524,880 | B2 | 9/2013 | Wilton et al. | |
| 8,557,549 | B2 | 10/2013 | Chang et al. | |
| 8,557,844 | B2 | 10/2013 | Platt et al. | |
| 8,592,566 | B2 | 11/2013 | Iwamura et al. | |
| 8,632,963 | B2 | 1/2014 | Shah et al. | |
| 8,633,206 | B2 * | 1/2014 | Promo | C07D 487/04 514/265.1 |
| 8,647,742 | B2 | 2/2014 | Dendukuri et al. | |
| 8,648,186 | B2 | 2/2014 | Monteleone | |
| 8,653,254 | B2 | 2/2014 | Umemoto et al. | |
| 8,669,058 | B2 | 3/2014 | Liew | |
| 8,674,044 | B2 | 3/2014 | Popot et al. | |
| 8,679,750 | B2 | 3/2014 | Hayden et al. | |
| 8,680,063 | B2 | 3/2014 | Aronin et al. | |
| 8,729,036 | B2 | 5/2014 | Zamore et al. | |
| 8,735,417 | B2 * | 5/2014 | Altman | C07D 417/12 514/247 |
| 8,750,507 | B2 | 6/2014 | Roosta et al. | |
| 8,754,107 | B2 * | 6/2014 | George | C07D 207/14 514/211.15 |
| 8,759,507 | B2 | 6/2014 | Van Deutekom | |
| 8,802,659 | B2 | 8/2014 | Thomas et al. | |
| 8,809,516 | B2 | 8/2014 | Manoharan et al. | |
| 8,815,817 | B2 | 8/2014 | Hessel et al. | |
| 8,822,671 | B2 | 9/2014 | Shimizu et al. | |
| 8,859,755 | B2 * | 10/2014 | Wada | C07H 21/02 536/25.3 |
| 8,865,146 | B2 | 10/2014 | Fukuhara et al. | |
| 8,871,785 | B2 | 10/2014 | Boojamra et al. | |
| 8,877,435 | B2 | 11/2014 | Helliwell et al. | |
| 8,883,752 | B2 | 11/2014 | Swayze et al. | |
| 8,883,969 | B2 | 11/2014 | Ide et al. | |
| 8,927,513 | B2 | 1/2015 | Manoharan et al. | |
| 8,952,145 | B2 | 2/2015 | Freier | |
| 8,957,040 | B2 | 2/2015 | Bennett et al. | |
| 8,957,042 | B2 | 2/2015 | Safe et al. | |
| 8,975,389 | B2 * | 3/2015 | Manoharan | C07H 19/073 536/23.1 |
| 8,980,853 | B2 | 3/2015 | Bennett et al. | |
| 8,987,222 | B2 | 3/2015 | Aronin et al. | |
| 8,987,435 | B2 | 3/2015 | Swayze et al. | |
| 8,993,738 | B2 | 3/2015 | Prakash et al. | |
| 9,006,198 | B2 | 4/2015 | Bennett et al. | |
| 9,018,368 | B2 | 4/2015 | Wilton et al. | |
| 9,024,007 | B2 | 5/2015 | Wilton et al. | |
| 9,035,040 | B2 | 5/2015 | Wilton et al. | |
| 9,040,674 | B2 | 5/2015 | Benson et al. | |
| 9,057,066 | B2 | 6/2015 | Hung et al. | |
| 9,120,774 | B2 | 9/2015 | Blagg et al. | |
| 9,121,020 | B2 | 9/2015 | Feinstein et al. | |
| 9,126,927 | B2 * | 9/2015 | Yao | C07D 207/06 |
| 9,127,033 | B2 | 9/2015 | Prakash et al. | |
| 9,127,123 | B2 | 9/2015 | Livingston et al. | |
| 9,132,289 | B2 | 9/2015 | Kawai | |
| 9,139,604 | B2 | 9/2015 | Boojamra et al. | |
| 9,175,286 | B2 | 11/2015 | Wilton et al. | |
| 9,186,367 | B2 | 11/2015 | Thomas et al. | |
| 9,249,416 | B2 | 2/2016 | Wilton et al. | |
| 9,260,716 | B2 | 2/2016 | Davidson et al. | |
| 9,273,315 | B2 | 3/2016 | Hung et al. | |
| 9,284,344 | B2 | 3/2016 | Kim et al. | |
| 9,308,252 | B2 | 4/2016 | Suckow et al. | |
| 9,321,799 | B2 | 4/2016 | Prakash et al. | |
| 9,353,372 | B2 | 5/2016 | Freier | |
| 9,382,540 | B2 | 7/2016 | Prakash et al. | |
| 9,382,575 | B2 | 7/2016 | Eom et al. | |
| 9,394,333 | B2 * | 7/2016 | Wada | C07H 1/00 |
| 9,422,555 | B2 | 8/2016 | Wilton et al. | |
| 9,428,541 | B2 | 8/2016 | Platt et al. | |
| 9,441,229 | B2 | 9/2016 | Wilton et al. | |
| 9,447,415 | B2 | 9/2016 | Wilton et al. | |
| 9,453,228 | B2 | 9/2016 | Kandimalla et al. | |
| 9,476,044 | B2 | 10/2016 | Tuschl et al. | |
| 9,480,740 | B2 | 11/2016 | Reed et al. | |
| 9,481,704 | B2 | 11/2016 | Clarke | |
| 9,572,824 | B2 | 2/2017 | Thomas et al. | |
| 9,598,458 | B2 * | 3/2017 | Shimizu | C07B 53/00 |

(56) References Cited

U.S. PATENT DOCUMENTS

| | | |
|---|---|---|
| 9,605,019 B2 * | 3/2017 | Verdine .................. A61K 31/66 |
| 9,605,262 B2 | 3/2017 | Wilton et al. |
| 9,605,263 B2 | 3/2017 | Rigo |
| 9,611,472 B2 | 4/2017 | Zamore et al. |
| 9,617,547 B2 | 4/2017 | Gemba |
| 9,695,211 B2 | 7/2017 | Wada et al. |
| 9,725,474 B2 | 8/2017 | Murata et al. |
| 9,738,895 B2 | 8/2017 | Swayze et al. |
| 9,744,183 B2 | 8/2017 | Verdine et al. |
| 9,809,616 B2 | 11/2017 | Amblard et al. |
| 9,827,258 B2 | 11/2017 | Thomas et al. |
| 9,885,082 B2 | 2/2018 | Hrdlicka |
| 9,896,688 B2 | 2/2018 | Chang et al. |
| 9,982,257 B2 | 5/2018 | Butler et al. |
| 10,144,933 B2 | 12/2018 | Gemba et al. |
| 10,149,905 B2 | 12/2018 | Gemba et al. |
| 10,160,969 B2 | 12/2018 | Meena et al. |
| 10,167,309 B2 * | 1/2019 | Shimizu .................. C07B 53/00 |
| 2001/0055761 A1 | 12/2001 | Kanemoto et al. |
| 2002/0013792 A1 | 1/2002 | Imielinski et al. |
| 2002/0082227 A1 | 6/2002 | Henry |
| 2002/0137921 A1 | 9/2002 | Cook |
| 2002/0183502 A1 | 12/2002 | Mesmaeker et al. |
| 2003/0045705 A1 | 3/2003 | Cook et al. |
| 2003/0049662 A1 | 3/2003 | Monia et al. |
| 2003/0050261 A1 | 3/2003 | Krieg et al. |
| 2003/0159938 A1 | 8/2003 | Hradil |
| 2003/0198982 A1 | 10/2003 | Seela et al. |
| 2003/0232978 A1 | 12/2003 | Seeberger et al. |
| 2003/0235845 A1 | 12/2003 | van Ommen et al. |
| 2004/0002596 A1 | 1/2004 | Hong et al. |
| 2004/0023901 A1 | 2/2004 | Cook et al. |
| 2004/0023921 A1 | 2/2004 | Hong et al. |
| 2004/0059104 A1 | 3/2004 | Cook et al. |
| 2004/0063647 A1 | 4/2004 | Johnson |
| 2004/0149587 A1 | 8/2004 | Hradil |
| 2004/0203145 A1 | 10/2004 | Zamore et al. |
| 2004/0213780 A1 | 10/2004 | Krainc |
| 2005/0042646 A1 | 2/2005 | Davidson et al. |
| 2005/0059619 A1 | 3/2005 | Krieg et al. |
| 2005/0096284 A1 | 5/2005 | McSwiggen |
| 2005/0159375 A1 | 7/2005 | Srivastava et al. |
| 2005/0169888 A1 | 8/2005 | Hartmann et al. |
| 2005/0176045 A1 | 8/2005 | Fedorov et al. |
| 2005/0203044 A1 | 9/2005 | Zinnen |
| 2005/0215513 A1 | 9/2005 | Boojamra et al. |
| 2005/0227947 A1 | 10/2005 | Chen et al. |
| 2005/0239102 A1 | 10/2005 | Verdine et al. |
| 2005/0261237 A1 | 11/2005 | Boojamra et al. |
| 2005/0277133 A1 | 12/2005 | McSwiggen |
| 2005/0277609 A1 | 12/2005 | Krieg et al. |
| 2006/0003962 A1 | 1/2006 | Ahluwalia et al. |
| 2006/0035858 A1 | 2/2006 | Geary et al. |
| 2006/0035866 A1 | 2/2006 | Cannizzaro et al. |
| 2006/0041115 A1 | 2/2006 | Ravikumar |
| 2006/0063730 A1 | 3/2006 | Monia et al. |
| 2006/0079478 A1 | 4/2006 | Boojamra et al. |
| 2006/0099616 A1 | 5/2006 | van Ommen et al. |
| 2006/0147952 A1 | 7/2006 | van Ommen et al. |
| 2006/0166910 A1 | 7/2006 | Tuschl et al. |
| 2006/0199776 A1 | 9/2006 | Blagg et al. |
| 2006/0199788 A1 | 9/2006 | Cannizzaro et al. |
| 2006/0211644 A1 | 9/2006 | Krieg et al. |
| 2006/0257912 A1 | 11/2006 | Kaemmerer et al. |
| 2006/0264404 A1 | 11/2006 | Boojamra et al. |
| 2007/0027116 A1 | 2/2007 | Cho et al. |
| 2007/0099851 A1 | 5/2007 | Linn |
| 2007/0099860 A1 | 5/2007 | Sah et al. |
| 2007/0123484 A1 | 5/2007 | Bhat et al. |
| 2007/0135363 A1 | 6/2007 | Cook et al. |
| 2007/0149462 A1 | 6/2007 | Iyer et al. |
| 2007/0161547 A1 | 7/2007 | Bhat et al. |
| 2007/0161590 A1 | 7/2007 | Van Bilsen et al. |
| 2007/0196852 A1 | 8/2007 | Heindl et al. |
| 2007/0249589 A1 | 10/2007 | Aebi et al. |
| 2007/0259832 A1 | 11/2007 | Cook et al. |
| 2007/0265224 A1 | 11/2007 | Cook et al. |
| 2007/0270452 A1 | 11/2007 | Blagg et al. |
| 2007/0282097 A1 | 12/2007 | Ohgi et al. |
| 2007/0287831 A1 | 12/2007 | Seth et al. |
| 2007/0299027 A1 | 12/2007 | Hung et al. |
| 2008/0015158 A1 | 1/2008 | Ichiro et al. |
| 2008/0015162 A1 | 1/2008 | Bhanot et al. |
| 2008/0039418 A1 | 2/2008 | Freier |
| 2008/0045473 A1 | 2/2008 | Uhlmann et al. |
| 2008/0064867 A1 | 3/2008 | Leuck et al. |
| 2008/0119426 A1 | 5/2008 | Dale |
| 2008/0200409 A1 | 8/2008 | Wilson et al. |
| 2008/0200423 A1 | 8/2008 | Cook et al. |
| 2008/0209581 A1 | 8/2008 | van Ommen et al. |
| 2008/0221055 A1 | 9/2008 | Sah et al. |
| 2008/0221303 A1 | 9/2008 | Katzhendler et al. |
| 2008/0249291 A1 | 10/2008 | Kwon et al. |
| 2008/0274989 A1 | 11/2008 | Davidson et al. |
| 2009/0012120 A1 | 1/2009 | Borhan et al. |
| 2009/0023675 A1 | 1/2009 | McSwiggen et al. |
| 2009/0053148 A1 | 2/2009 | Kandimalla et al. |
| 2009/0053205 A1 | 2/2009 | Kandimalla et al. |
| 2009/0060898 A1 | 3/2009 | Kandimalla et al. |
| 2009/0062224 A1 | 3/2009 | Kim et al. |
| 2009/0076246 A1 | 3/2009 | van Deutekom |
| 2009/0093425 A1 | 4/2009 | Dowdy et al. |
| 2009/0131372 A1 | 5/2009 | Chen et al. |
| 2009/0162316 A1 | 6/2009 | Verdine et al. |
| 2009/0163709 A1 | 6/2009 | Blagg |
| 2009/0186410 A1 | 7/2009 | Aronin et al. |
| 2009/0187014 A1 | 7/2009 | Blagg |
| 2009/0227543 A1 | 9/2009 | Cannizzaro et al. |
| 2009/0228998 A1 | 9/2009 | van Ommen et al. |
| 2009/0247488 A1 | 10/2009 | Cannizzaro et al. |
| 2009/0263413 A1 | 10/2009 | Iwamura et al. |
| 2009/0275535 A1 | 11/2009 | Boojamra et al. |
| 2009/0306176 A1 | 12/2009 | Schlingensiepen et al. |
| 2010/0008937 A1 | 1/2010 | Peer et al. |
| 2010/0008981 A1 | 1/2010 | Kaemmerer et al. |
| 2010/0022467 A1 | 1/2010 | Boojamra et al. |
| 2010/0022620 A1 | 1/2010 | Crispin et al. |
| 2010/0038543 A1 | 2/2010 | Toda et al. |
| 2010/0048882 A1 | 2/2010 | Blagg et al. |
| 2010/0069472 A1 | 3/2010 | Hung et al. |
| 2010/0074889 A1 | 3/2010 | Qiu et al. |
| 2010/0105630 A1 | 4/2010 | Blagg |
| 2010/0120900 A1 | 5/2010 | van Bilsen et al. |
| 2010/0186626 A1 | 7/2010 | Shin et al. |
| 2010/0203002 A1 | 8/2010 | Fukuhara et al. |
| 2010/0204162 A1 | 8/2010 | Platt et al. |
| 2010/0215642 A1 | 8/2010 | Lan et al. |
| 2010/0273999 A1 | 10/2010 | Jung et al. |
| 2010/0299768 A1 | 11/2010 | Perrin et al. |
| 2010/0311684 A1 | 12/2010 | Cook et al. |
| 2010/0325746 A9 | 12/2010 | Kaemmerer et al. |
| 2011/0009477 A1 | 1/2011 | Yu et al. |
| 2011/0015253 A1 | 1/2011 | Wilton et al. |
| 2011/0015258 A1 | 1/2011 | Wilton et al. |
| 2011/0021365 A1 | 1/2011 | Seela et al. |
| 2011/0039334 A1 | 2/2011 | Bennett et al. |
| 2011/0046203 A1 | 2/2011 | Wilton et al. |
| 2011/0071101 A1 | 3/2011 | Boojamra et al. |
| 2011/0105587 A1 | 5/2011 | Fishcher et al. |
| 2011/0111491 A1 | 5/2011 | Davidson et al. |
| 2011/0136765 A1 | 6/2011 | Promo et al. |
| 2011/0178284 A1 | 7/2011 | Wada et al. |
| 2011/0201599 A1 | 8/2011 | Bahceci et al. |
| 2011/0212520 A1 | 9/2011 | Davidson et al. |
| 2011/0213010 A1 | 9/2011 | Hayden et al. |
| 2011/0257251 A1 | 10/2011 | Gude-Rodriguez et al. |
| 2011/0263686 A1 | 10/2011 | Wilton et al. |
| 2011/0269814 A1 | 11/2011 | Manoharan et al. |
| 2011/0269821 A1 | 11/2011 | Swayze et al. |
| 2011/0288053 A1 | 11/2011 | Boojamra et al. |
| 2011/0294124 A1 * | 12/2011 | Wada et al. .................. 435/6.11 |
| 2011/0294869 A1 | 12/2011 | Petersen |
| 2011/0306652 A1 | 12/2011 | Freier |
| 2011/0312086 A1 | 12/2011 | Van Deutekom |

(56) References Cited

U.S. PATENT DOCUMENTS

| | | |
|---|---|---|
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0059045 A1 | 3/2012 | Prakash et al. |
| 2012/0064137 A1 | 3/2012 | Kawai |
| 2012/0095076 A1 | 4/2012 | Sah et al. |
| 2012/0108800 A1 | 5/2012 | Murata et al. |
| 2012/0136039 A1 | 5/2012 | Aronin et al. |
| 2012/0156138 A1 | 6/2012 | Smith |
| 2012/0157511 A1 | 6/2012 | Manoharan et al. |
| 2012/0190649 A1 | 7/2012 | Thomas et al. |
| 2012/0208864 A1 | 8/2012 | Bhanot et al. |
| 2012/0214865 A1 | 8/2012 | Bennett et al. |
| 2012/0216823 A1 | 8/2012 | Fukuhara et al. |
| 2012/0246747 A1 | 9/2012 | Tuschl et al. |
| 2012/0252745 A1 | 10/2012 | Blagg et al. |
| 2012/0252879 A1 | 10/2012 | Hung et al. |
| 2012/0276037 A1 | 11/2012 | Suzuki et al. |
| 2012/0308609 A1 | 12/2012 | Gibbon et al. |
| 2012/0316224 A1 | 12/2012 | Verdine et al. |
| 2013/0005794 A1 | 1/2013 | Kaemmerer et al. |
| 2013/0046008 A1 | 2/2013 | Bennett et al. |
| 2013/0072671 A1 | 3/2013 | Van Deutekom |
| 2013/0084576 A1 | 4/2013 | Prakash et al. |
| 2013/0116310 A1 | 5/2013 | Wilton et al. |
| 2013/0116420 A1 | 5/2013 | Prakash et al. |
| 2013/0156845 A1 | 6/2013 | Manoharan et al. |
| 2013/0184450 A1 | 7/2013 | Wada et al. |
| 2013/0189782 A1 | 7/2013 | Hung et al. |
| 2013/0197061 A1 | 8/2013 | Hohjoh et al. |
| 2013/0217755 A1 | 8/2013 | Wilton et al. |
| 2013/0236536 A1 | 9/2013 | Phiasivongsa et al. |
| 2013/0243725 A1 | 9/2013 | Clarke |
| 2013/0253033 A1 | 9/2013 | Wilton et al. |
| 2013/0253178 A1 | 9/2013 | Shimizu et al. |
| 2013/0253180 A1 | 9/2013 | Wilton et al. |
| 2013/0274313 A1 | 10/2013 | Wilton et al. |
| 2013/0281684 A1 | 10/2013 | Freier |
| 2013/0302806 A1 | 11/2013 | Van Deutekom |
| 2013/0316969 A1 | 11/2013 | Boojamra et al. |
| 2013/0323836 A1 | 12/2013 | Manoharan et al. |
| 2013/0331438 A1 | 12/2013 | Wilton et al. |
| 2013/0345462 A1 | 12/2013 | Matsuda et al. |
| 2014/0080769 A1 | 3/2014 | Platt et al. |
| 2014/0080896 A1 | 3/2014 | Nelson et al. |
| 2014/0080898 A1 | 3/2014 | Wilton et al. |
| 2014/0107330 A1 | 4/2014 | Freier et al. |
| 2014/0120088 A1 | 5/2014 | Carpentier |
| 2014/0142160 A1 | 5/2014 | Lee et al. |
| 2014/0155587 A1 | 6/2014 | Wilton et al. |
| 2014/0163213 A1 | 6/2014 | Debelak et al. |
| 2014/0194610 A1 | 7/2014 | Verdine et al. |
| 2014/0213635 A1 | 7/2014 | Van Deutekom |
| 2014/0220573 A1 | 8/2014 | Hrdlicka |
| 2014/0221395 A1 | 8/2014 | Dhanoa |
| 2014/0235566 A1 | 8/2014 | Amblard et al. |
| 2014/0243515 A1 | 8/2014 | Wilton et al. |
| 2014/0243516 A1 | 8/2014 | Wilton et al. |
| 2014/0255936 A1 | 9/2014 | Rademakers et al. |
| 2014/0256578 A1 | 9/2014 | Hayden et al. |
| 2014/0275212 A1 | 9/2014 | van Deutekom |
| 2014/0303238 A1 | 10/2014 | Linsley et al. |
| 2014/0309190 A1 | 10/2014 | Thomas et al. |
| 2014/0309283 A1 | 10/2014 | Wilton et al. |
| 2014/0309284 A1 | 10/2014 | Wilton et al. |
| 2014/0309285 A1 | 10/2014 | Wilton et al. |
| 2014/0316121 A1 | 10/2014 | Prakash et al. |
| 2014/0323707 A1 | 10/2014 | Seth et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2014/0373188 A1 | 12/2014 | Zamore et al. |
| 2014/0378527 A1 | 12/2014 | Van Deutekom |
| 2015/0025039 A1 | 1/2015 | Boojamra et al. |
| 2015/0051389 A1 | 2/2015 | Seth et al. |
| 2015/0057330 A1 | 2/2015 | Wilton et al. |
| 2015/0080457 A1 | 3/2015 | Manoharan et al. |
| 2015/0080563 A2 | 3/2015 | van Deutekom |
| 2015/0096064 A1 | 4/2015 | Tuschl et al. |
| 2015/0126725 A1 | 5/2015 | Swayze et al. |
| 2015/0148404 A1 | 5/2015 | de Visser et al. |
| 2015/0159163 A1 | 6/2015 | Prakash et al. |
| 2015/0166999 A1 | 6/2015 | Gemba |
| 2015/0167006 A1 | 6/2015 | Swayze et al. |
| 2015/0197540 A1 | 7/2015 | Shimizu et al. |
| 2015/0211006 A1 | 7/2015 | Butler et al. |
| 2015/0218559 A1 | 8/2015 | Van Deutekom et al. |
| 2015/0259679 A1 | 9/2015 | Bennett et al. |
| 2015/0267197 A1 | 9/2015 | Bennett et al. |
| 2015/0275208 A1 | 10/2015 | Oestergaard et al. |
| 2015/0291636 A1 | 10/2015 | Atamanyuk et al. |
| 2015/0292015 A1 | 10/2015 | Bennett et al. |
| 2015/0307877 A1 | 10/2015 | Freier |
| 2015/0315594 A1 | 11/2015 | Prakash et al. |
| 2015/0322434 A1 | 11/2015 | van Deutekom |
| 2015/0329859 A1 | 11/2015 | Bennett et al. |
| 2015/0335708 A1 | 11/2015 | Froelich et al. |
| 2015/0353931 A1 | 12/2015 | Wilton et al. |
| 2015/0361424 A1 | 12/2015 | van Deutekom |
| 2015/0376615 A1 | 12/2015 | Wilton et al. |
| 2015/0376616 A1 | 12/2015 | Wilton et al. |
| 2015/0376624 A1 | 12/2015 | Gryaznov et al. |
| 2015/0376625 A1 | 12/2015 | Oestergaard et al. |
| 2016/0002281 A1 | 1/2016 | Mayes et al. |
| 2016/0002631 A1 | 1/2016 | Wilton et al. |
| 2016/0002632 A1 | 1/2016 | Wilton et al. |
| 2016/0002635 A1 | 1/2016 | Wilton et al. |
| 2016/0017327 A1 | 1/2016 | Rudnicki et al. |
| 2016/0024496 A1 | 1/2016 | Bennett et al. |
| 2016/0040161 A1 | 2/2016 | Packard et al. |
| 2016/0046939 A1 | 2/2016 | Prakash et al. |
| 2016/0050929 A1 | 2/2016 | Benfatti et al. |
| 2016/0050930 A1 | 2/2016 | Benfatti et al. |
| 2016/0053256 A1 | 2/2016 | Hung et al. |
| 2016/0068837 A1 | 3/2016 | Chang et al. |
| 2016/0076033 A1 | 3/2016 | Torii et al. |
| 2016/0108396 A1 | 4/2016 | Jensen et al. |
| 2016/0122761 A1 | 5/2016 | Prakash et al. |
| 2016/0128928 A1 | 5/2016 | Fukuhara et al. |
| 2016/0129023 A1 | 5/2016 | Thomas et al. |
| 2016/0138022 A1 | 5/2016 | Kandimalla et al. |
| 2016/0159846 A1 | 6/2016 | Prakash et al. |
| 2016/0168570 A1 | 6/2016 | Van Deutekom et al. |
| 2016/0186175 A1 | 6/2016 | Seth et al. |
| 2016/0186178 A1 | 6/2016 | Radovic-Moreno et al. |
| 2016/0186185 A1 | 6/2016 | Prakash et al. |
| 2016/0194349 A1 | 7/2016 | Prakash et al. |
| 2016/0194636 A1 | 7/2016 | Van Deutekom et al. |
| 2016/0214974 A1 | 7/2016 | Schaetzer et al. |
| 2016/0230172 A1 | 8/2016 | Rigo |
| 2016/0237108 A1 | 8/2016 | Fraley et al. |
| 2016/0237432 A1 | 8/2016 | Bennett et al. |
| 2016/0251653 A1 | 9/2016 | Davidson et al. |
| 2016/0251655 A1 | 9/2016 | Freier et al. |
| 2016/0251658 A1 | 9/2016 | Van Deutekom et al. |
| 2016/0264964 A1 | 9/2016 | Cancilla et al. |
| 2016/0312217 A1 | 10/2016 | Hung et al. |
| 2016/0331835 A1 | 11/2016 | Gemba et al. |
| 2016/0331836 A1 | 11/2016 | Gemba et al. |
| 2016/0333349 A1 | 11/2016 | Gemba et al. |
| 2016/0347780 A1 | 12/2016 | Wada et al. |
| 2016/0347784 A1 | 12/2016 | Verdine et al. |
| 2016/0355810 A1 | 12/2016 | Van Deutekom |
| 2016/0369273 A1 | 12/2016 | Freier |
| 2017/0009233 A1 | 1/2017 | Wilton et al. |
| 2017/0009234 A1 | 1/2017 | Wilton et al. |
| 2017/0029445 A1 | 2/2017 | Shimizu et al. |
| 2017/0029457 A1 | 2/2017 | Verdine et al. |
| 2017/0037399 A1 | 2/2017 | . et al. |
| 2017/0044526 A1 | 2/2017 | Wan et al. |

(56) References Cited

U.S. PATENT DOCUMENTS

| | | |
|---|---|---|
| 2017/0067050 A1 | 3/2017 | Tuschl et al. |
| 2017/0114086 A1 | 4/2017 | Clarke |
| 2017/0114340 A1 | 4/2017 | Mueller et al. |
| 2017/0130224 A1 | 5/2017 | Oestergaard et al. |
| 2017/0197903 A1 | 7/2017 | Hoashi |
| 2017/0239280 A1 | 8/2017 | Thomas et al. |
| 2017/0275621 A1 | 9/2017 | Butler et al. |
| 2017/0327824 A1 | 11/2017 | Oestergaard et al. |
| 2017/0349897 A1 | 12/2017 | Rigo |
| 2018/0111958 A1 | 4/2018 | Wada et al. |
| 2018/0216107 A1 | 8/2018 | Frank-Kamenetsky et al. |
| 2018/0216108 A1 | 8/2018 | Vargeese et al. |
| 2018/0222936 A1 | 8/2018 | Verdine et al. |

FOREIGN PATENT DOCUMENTS

| | | |
|---|---|---|
| DE | 1144279 B | 2/1963 |
| DE | 01934150 A1 | 1/1970 |
| DE | 133885 A1 | 1/1979 |
| EA | 008940 B1 | 10/2007 |
| EP | 269258 A2 | 6/1968 |
| EP | 0 002 322 A2 | 6/1979 |
| EP | 192521 A1 | 8/1986 |
| EP | 0506242 A1 | 9/1992 |
| EP | 0531447 A1 | 3/1993 |
| EP | 0604409 A1 | 7/1994 |
| EP | 0655088 A1 | 5/1995 |
| EP | 0779893 A2 | 6/1997 |
| EP | 0831854 A1 | 4/1998 |
| EP | 0973945 A1 | 1/2000 |
| EP | 1097162 A2 | 5/2001 |
| EP | 1100807 A1 | 5/2001 |
| EP | 1185305 | 3/2002 |
| EP | 1244682 A1 | 10/2002 |
| EP | 1311526 A1 | 5/2003 |
| EP | 1418179 A2 | 5/2004 |
| EP | 1499627 A2 | 1/2005 |
| EP | 1539188 A2 | 6/2005 |
| EP | 1556077 A2 | 7/2005 |
| EP | 1560840 A2 | 8/2005 |
| EP | 1562971 A2 | 8/2005 |
| EP | 1670810 A2 | 6/2006 |
| EP | 1670896 A2 | 6/2006 |
| EP | 1795536 A1 | 6/2007 |
| EP | 1957507 A2 | 8/2008 |
| EP | 1984381 A2 | 10/2008 |
| EP | 2021472 A2 | 2/2009 |
| EP | 2062980 A2 | 5/2009 |
| EP | 2066684 A2 | 6/2009 |
| EP | 2149571 A1 | 2/2010 |
| EP | 2161038 A1 | 3/2010 |
| EP | 2170917 A2 | 4/2010 |
| EP | 2173760 A2 | 4/2010 |
| EP | 2176280 A2 | 4/2010 |
| EP | 2282744 A1 | 2/2011 |
| EP | 2285819 A1 | 2/2011 |
| EP | 2316967 A1 | 5/2011 |
| EP | 2320895 A2 | 5/2011 |
| EP | 2360166 A1 | 8/2011 |
| EP | 1 866 319 B1 | 11/2011 |
| EP | 2399588 A1 | 12/2011 |
| EP | 2422819 A2 | 2/2012 |
| EP | 2428227 A1 | 3/2012 |
| EP | 2458005 A1 | 5/2012 |
| EP | 2462153 A2 | 6/2012 |
| EP | 2479182 A1 | 7/2012 |
| EP | 1606407 B1 | 12/2013 |
| EP | 14193887.8 | 11/2014 |
| EP | 14196167.0 | 12/2014 |
| EP | 15182401.8 | 8/2015 |
| EP | 15191074.2 | 10/2015 |
| EP | 15191075.9 | 10/2015 |
| EP | 15191076.7 | 10/2015 |
| EP | 2982758 A1 | 2/2016 |
| EP | 2125852 B1 | 4/2016 |
| EP | 2370451 B1 | 11/2016 |
| EP | 2 534 262 B1 | 12/2016 |
| GB | 1448437 A | 9/1976 |
| GB | 2016273 A | 9/1979 |
| JP | 61-280473 A | 12/1986 |
| JP | 3072345 B1 | 7/2000 |
| JP | 2002-513763 A | 5/2002 |
| JP | 2002/514397 A | 5/2002 |
| JP | 2002-521489 A | 7/2002 |
| JP | 2003-510290 A | 3/2003 |
| JP | 2003/238586 A | 8/2003 |
| JP | 2005-89441 A | 4/2005 |
| JP | 2006-508693 A | 3/2006 |
| JP | 2006-515277 A | 5/2006 |
| JP | 2008-531018 A | 8/2008 |
| JP | 2009-190983 A | 8/2009 |
| JP | 4348044 B2 | 10/2009 |
| JP | 04348077 B2 | 10/2009 |
| JP | 2010-504750 A | 2/2010 |
| JP | 2010/241836 A | 10/2010 |
| JP | 2010/265304 A | 11/2010 |
| JP | 2001-503267 A | 3/2011 |
| JP | A03-074398 | 3/2011 |
| JP | 2011/088935 A | 5/2011 |
| JP | 2011/225598 A | 11/2011 |
| WO | WO-91/10671 A1 | 7/1991 |
| WO | WO-91/16331 A1 | 10/1991 |
| WO | WO-91/17755 A1 | 11/1991 |
| WO | WO-92/03452 A1 | 3/1992 |
| WO | WO-92/20822 A1 | 11/1992 |
| WO | WO-92/20823 A1 | 11/1992 |
| WO | WO-93/08296 A1 | 4/1993 |
| WO | WO-94/17093 A1 | 8/1994 |
| WO | WO-94/22886 A1 | 10/1994 |
| WO | WO-94/22888 A1 | 10/1994 |
| WO | WO-94/22890 A1 | 10/1994 |
| WO | WO-96/02555 A1 | 2/1996 |
| WO | WO-96/07392 A2 | 3/1996 |
| WO | WO-96/14329 A1 | 5/1996 |
| WO | WO-96/19572 A1 | 6/1996 |
| WO | WO-96/36627 A1 | 11/1996 |
| WO | WO-96/37504 A1 | 11/1996 |
| WO | WO-96/39413 A1 | 12/1996 |
| WO | WO-97/06183 A1 | 2/1997 |
| WO | WO-97/09443 A1 | 3/1997 |
| WO | WO-97/14710 A1 | 4/1997 |
| WO | WO-97/47637 A1 | 12/1997 |
| WO | WO-98/02582 A2 | 1/1998 |
| WO | WO-98/03542 A1 | 1/1998 |
| WO | WO-98/07734 A1 | 2/1998 |
| WO | WO-98/016535 A1 | 4/1998 |
| WO | WO-98/18810 A1 | 5/1998 |
| WO | WO-98/39334 A1 | 9/1998 |
| WO | WO-98/46794 A1 | 10/1998 |
| WO | WO-98/53801 A1 | 12/1998 |
| WO | WO-99/00377 A1 | 1/1999 |
| WO | WO-99/05160 A2 | 2/1999 |
| WO | WO-99/12034 A1 | 3/1999 |
| WO | WO-99/56755 A1 | 11/1999 |
| WO | WO-99/58118 A2 | 11/1999 |
| WO | WO-00/00499 A1 | 1/2000 |
| WO | WO-00/04034 A2 | 1/2000 |
| WO | WO-00/06588 A1 | 2/2000 |
| WO | WO-00/09159 A1 | 2/2000 |
| WO | 00/23444 A1 | 4/2000 |
| WO | WO-00/31110 A1 | 6/2000 |
| WO | WO-00/37658 A2 | 8/2000 |
| WO | WO-00/55179 A1 | 9/2000 |
| WO | WO-00/58329 A1 | 10/2000 |
| WO | WO-00/76554 A1 | 12/2000 |
| WO | WO-01/02415 A1 | 1/2001 |
| WO | WO-01/022990 A2 | 4/2001 |
| WO | WO-01/022990 A2 | 4/2001 |
| WO | WO-01/27126 A1 | 4/2001 |
| WO | WO-01/40515 A1 | 6/2001 |
| WO | WO-01/49701 A1 | 7/2001 |
| WO | WO-01/64702 A1 | 9/2001 |
| WO | WO-2001/068663 A1 | 9/2001 |
| WO | WO-01/81303 A1 | 11/2001 |

(56) References Cited

FOREIGN PATENT DOCUMENTS

| | | |
|---|---|---|
| WO | WO-01/85751 A1 | 11/2001 |
| WO | WO-01/88198 A1 | 11/2001 |
| WO | WO-02/12263 A1 | 2/2002 |
| WO | WO-02/14340 A1 | 2/2002 |
| WO | WO-02/15410 A2 | 2/2002 |
| WO | WO-02/20544 A1 | 3/2002 |
| WO | WO-02/22635 A1 | 3/2002 |
| WO | WO-02/24906 A1 | 3/2002 |
| WO | WO-02/32450 A2 | 4/2002 |
| WO | WO-02/57425 A2 | 7/2002 |
| WO | WO-2002/051716 A1 | 7/2002 |
| WO | WO-02/97134 A2 | 12/2002 |
| WO | WO-02/099317 A1 | 12/2002 |
| WO | WO-03/002065 A2 | 1/2003 |
| WO | WO-03/004602 A2 | 1/2003 |
| WO | WO-03/011887 A2 | 2/2003 |
| WO | WO-03/012057 A2 | 2/2003 |
| WO | WO-03/014306 A2 | 2/2003 |
| WO | WO-03/014307 A2 | 2/2003 |
| WO | WO-03/018600 A2 | 3/2003 |
| WO | WO-03/066633 A1 | 8/2003 |
| WO | WO-2003/071001 A1 | 8/2003 |
| WO | WO-2003/072757 A2 | 9/2003 |
| WO | WO-2003/073989 A2 | 9/2003 |
| WO | WO-03/097662 A1 | 11/2003 |
| WO | WO-03/099840 A1 | 12/2003 |
| WO | WO-03/100017 A2 | 12/2003 |
| WO | WO-03/106477 A1 | 12/2003 |
| WO | WO-2004/000351 A1 | 12/2003 |
| WO | WO-2004/003228 A1 | 1/2004 |
| WO | WO-2004/007718 A2 | 1/2004 |
| WO | WO-2004/014312 A2 | 2/2004 |
| WO | WO-2004/014933 A1 | 2/2004 |
| WO | WO-2004/016805 A2 | 2/2004 |
| WO | WO-2004010956 A2 | 2/2004 |
| WO | WO-2004/024919 A1 | 3/2004 |
| WO | WO-2004/039629 A2 | 5/2004 |
| WO | WO-2004041889 A2 | 5/2004 |
| WO | WO-2004044134 A2 | 5/2004 |
| WO | WO-2004044136 A2 | 5/2004 |
| WO | WO-2004044141 A2 | 5/2004 |
| WO | WO-2004044181 A2 | 5/2004 |
| WO | WO-2004/048522 A2 | 6/2004 |
| WO | WO-2004/055162 A2 | 7/2004 |
| WO | WO-2004/080466 A1 | 9/2004 |
| WO | WO-2004/083432 A1 | 9/2004 |
| WO | WO-2004/083446 A2 | 9/2004 |
| WO | WO-2004/085454 A1 | 10/2004 |
| WO | WO-2004/096233 A2 | 11/2004 |
| WO | WO-2004/096235 A2 | 11/2004 |
| WO | WO-2004/096286 A2 | 11/2004 |
| WO | WO-2004093783 A2 | 11/2004 |
| WO | WO-2005/002626 A2 | 1/2005 |
| WO | WO-2005000201 A2 | 1/2005 |
| WO | WO-2005005599 A2 | 1/2005 |
| WO | WO-2005/014609 A2 | 2/2005 |
| WO | WO-2005013901 A2 | 2/2005 |
| WO | WO-2005/019236 A1 | 3/2005 |
| WO | WO-2005/019237 A1 | 3/2005 |
| WO | WO-2005/021568 A2 | 3/2005 |
| WO | WO-2005/023828 A1 | 3/2005 |
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO-2005/039830 A2 | 5/2005 |
| WO | WO-2005/042018 A2 | 5/2005 |
| WO | WO-2005/042716 A2 | 5/2005 |
| WO | WO-2005040180 A2 | 5/2005 |
| WO | WO-2005063976 A2 | 7/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/000057 A1 | 1/2006 |
| WO | WO-2006020676 A2 | 2/2006 |
| WO | WO-2006/022323 A1 | 3/2006 |
| WO | WO-2006/029258 A2 | 3/2006 |
| WO | WO-2006/031267 A2 | 3/2006 |
| WO | WO-2006031461 A2 | 3/2006 |
| WO | WO-2006044531 A2 | 4/2006 |
| WO | WO-2006/049454 A1 | 5/2006 |
| WO | WO-2006/050501 A2 | 5/2006 |
| WO | WO-2006/053861 A1 | 5/2006 |
| WO | WO-2006/065751 A2 | 6/2006 |
| WO | WO-2006/066260 A2 | 6/2006 |
| WO | WO-2006/070284 A1 | 7/2006 |
| WO | WO-2006/080596 A1 | 8/2006 |
| WO | WO-2006/091915 A2 | 8/2006 |
| WO | WO-2006/117400 A2 | 11/2006 |
| WO | WO-2006/121960 A2 | 11/2006 |
| WO | WO-2007/002904 A2 | 1/2007 |
| WO | WO-2007/005941 A2 | 1/2007 |
| WO | WO-2007027775 A2 | 3/2007 |
| WO | WO-2007/041045 A2 | 4/2007 |
| WO | WO-2007/051045 A2 | 5/2007 |
| WO | WO-2007/059041 A2 | 5/2007 |
| WO | WO-2007/064291 A1 | 6/2007 |
| WO | WO-2007/070598 A2 | 6/2007 |
| WO | WO-2007064954 A2 | 6/2007 |
| WO | WO-2007/089584 A2 | 8/2007 |
| WO | WO-2007/089611 A2 | 8/2007 |
| WO | WO-2007/090071 A2 | 8/2007 |
| WO | WO-2007/095316 A2 | 8/2007 |
| WO | WO-2007131232 A2 | 11/2007 |
| WO | WO-2007131237 A2 | 11/2007 |
| WO | WO-2007131238 A2 | 11/2007 |
| WO | WO-2007134014 A2 | 11/2007 |
| WO | WO-2007136988 A2 | 11/2007 |
| WO | WO-2007/139190 A1 | 12/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/005562 A2 | 1/2008 |
| WO | WO-2008/008476 A2 | 1/2008 |
| WO | WO-2008/021136 A2 | 2/2008 |
| WO | WO-2008017081 A1 | 2/2008 |
| WO | WO-2008/049065 A1 | 4/2008 |
| WO | WO-2008/051763 A1 | 5/2008 |
| WO | WO-2008/068638 A2 | 6/2008 |
| WO | WO-2008/073959 A2 | 6/2008 |
| WO | WO-2008/098104 A1 | 6/2008 |
| WO | WO-2008066776 A2 | 6/2008 |
| WO | WO-2008118883 A1 | 10/2008 |
| WO | WO-2008139262 A2 | 11/2008 |
| WO | WO-2008/148801 A2 | 12/2008 |
| WO | WO-2008/151833 A2 | 12/2008 |
| WO | WO-2009/001097 A2 | 12/2008 |
| WO | WO-2009/007855 A2 | 1/2009 |
| WO | WO-2009/014237 A2 | 1/2009 |
| WO | WO-2009046141 A2 | 4/2009 |
| WO | WO-2009/086264 A1 | 7/2009 |
| WO | WO-2009/089659 A1 | 7/2009 |
| WO | WO-2009/098197 A1 | 8/2009 |
| WO | WO-2009/117589 A1 | 9/2009 |
| WO | WO-2009/124238 A1 | 10/2009 |
| WO | WO-2009/135322 A1 | 11/2009 |
| WO | WO-2009/143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A2 | 1/2010 |
| WO | WO-2010/030858 A1 | 3/2010 |
| WO | WO-2010/039543 A2 | 4/2010 |
| WO | WO-2010/042636 A2 | 4/2010 |
| WO | WO-2010/048549 A2 | 4/2010 |
| WO | WO-2010/048585 A2 | 4/2010 |
| WO | WO-2010036696 A1 | 4/2010 |
| WO | WO-2010036698 A1 | 4/2010 |
| WO | WO-2010048552 A2 | 4/2010 |
| WO | 2010/064146 A2 | 6/2010 |
| WO | WO-2010/072831 A1 | 7/2010 |

(56) References Cited

FOREIGN PATENT DOCUMENTS

| | | |
|---|---|---|
| WO | WO-2010080953 A1 | 7/2010 |
| WO | WO-2010/096650 A1 | 8/2010 |
| WO | WO-2010091301 A1 | 8/2010 |
| WO | WO-2010107838 A1 | 9/2010 |
| WO | WO-2010/113937 A1 | 10/2010 |
| WO | WO-2010/118263 A1 | 10/2010 |
| WO | WO-2010120262 A1 | 10/2010 |
| WO | WO-2010/129853 A2 | 11/2010 |
| WO | WO-2010/141471 A2 | 12/2010 |
| WO | WO-2010/146784 A1 | 12/2010 |
| WO | WO-2010/150789 A1 | 12/2010 |
| WO | WO-2011/005761 A1 | 1/2011 |
| WO | WO-2011/005764 A1 | 1/2011 |
| WO | WO-2011/005860 A2 | 1/2011 |
| WO | WO-2011/010706 A1 | 1/2011 |
| WO | WO-2011/015572 A1 | 2/2011 |
| WO | WO-2011/015573 A1 | 2/2011 |
| WO | WO-2011/017521 A2 | 2/2011 |
| WO | WO-2011/017561 A1 | 2/2011 |
| WO | WO-2011/034072 A1 | 3/2011 |
| WO | WO-2011038288 A1 | 3/2011 |
| WO | 2011/045702 A1 | 4/2011 |
| WO | WO-2011/062210 A1 | 5/2011 |
| WO | WO-2011/064974 A1 | 6/2011 |
| WO | WO-2011085271 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2011/133871 A2 | 10/2011 |
| WO | WO-2011127175 A1 | 10/2011 |
| WO | WO-2011127307 A1 | 10/2011 |
| WO | WO-2011/139699 A2 | 11/2011 |
| WO | WO-2011/139911 A2 | 11/2011 |
| WO | WO-2011135396 A1 | 11/2011 |
| WO | WO-2012/030683 A2 | 3/2012 |
| WO | WO-2012/039448 A1 | 3/2012 |
| WO | WO-2012/073857 A1 | 6/2012 |
| WO | WO-2012092367 A1 | 7/2012 |
| WO | WO-2012109395 A1 | 8/2012 |
| WO | WO-2012/151324 A1 | 11/2012 |
| WO | WO-2013/012758 A1 | 1/2013 |
| WO | WO-2013/013068 A2 | 1/2013 |
| WO | WO-2013/022984 A1 | 2/2013 |
| WO | WO-2013/022990 A1 | 2/2013 |
| WO | WO-2013022966 A1 | 2/2013 |
| WO | WO-2013022967 A1 | 2/2013 |
| WO | WO-2013/033223 A1 | 3/2013 |
| WO | WO-2013030588 A1 | 3/2013 |
| WO | WO-2013/089283 A1 | 6/2013 |
| WO | WO-2013/138236 A1 | 9/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/025805 A1 | 2/2014 |
| WO | WO-2014/028739 A1 | 2/2014 |
| WO | WO-2014/059356 A2 | 4/2014 |
| WO | WO-2014062686 A1 | 4/2014 |
| WO | WO-2014062691 A2 | 4/2014 |
| WO | WO-2014062736 A1 | 4/2014 |
| WO | WO-2014/067904 A1 | 5/2014 |
| WO | WO-2014/069520 A1 | 5/2014 |
| WO | WO-2014/076195 A1 | 5/2014 |
| WO | WO-2014/076196 A1 | 5/2014 |
| WO | WO-2014/080004 A1 | 5/2014 |
| WO | WO-2014070771 A1 | 5/2014 |
| WO | WO-2014/099941 A1 | 6/2014 |
| WO | WO-2014/118267 A1 | 8/2014 |
| WO | WO-2014/118272 A1 | 8/2014 |
| WO | WO-2014/130607 A1 | 8/2014 |
| WO | WO-2014/132671 A1 | 9/2014 |
| WO | WO-2014/154486 A1 | 10/2014 |
| WO | WO-2014/154488 A1 | 10/2014 |
| WO | WO-2014/179626 A2 | 11/2014 |
| WO | WO-2014/188001 A1 | 11/2014 |
| WO | WO-2014/192310 A1 | 12/2014 |
| WO | WO-2014/203518 A1 | 12/2014 |
| WO | WO-2014/205451 A2 | 12/2014 |
| WO | WO-2014/207232 A1 | 12/2014 |
| WO | WO-2015/010135 A2 | 1/2015 |
| WO | WO-2015/017675 A2 | 2/2015 |
| WO | WO-2015/032617 A1 | 3/2015 |
| WO | WO-2015/051169 A2 | 4/2015 |
| WO | WO-2015/051214 A1 | 4/2015 |
| WO | WO-2015/051366 A2 | 4/2015 |
| WO | WO-2015054676 A2 | 4/2015 |
| WO | WO-2015057727 A1 | 4/2015 |
| WO | WO-2015057738 A1 | 4/2015 |
| WO | WO-2015/070212 A1 | 5/2015 |
| WO | WO-2015/071388 A1 | 5/2015 |
| WO | WO-2015/089511 A2 | 6/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015143078 A1 | 9/2015 |
| WO | WO-2015/168172 A1 | 11/2015 |
| WO | WO-2015/168589 A2 | 11/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/020399 A1 | 2/2016 |
| WO | WO-2016/021683 A1 | 2/2016 |
| WO | WO-2016/027168 A2 | 2/2016 |
| WO | WO-2016/037191 A1 | 3/2016 |
| WO | WO-2016/079181 A1 | 5/2016 |
| WO | WO-2016/079183 A1 | 5/2016 |
| WO | WO-2016/096938 A1 | 6/2016 |
| WO | WO-2016/102664 A1 | 6/2016 |
| WO | WO-2016112132 A1 | 7/2016 |
| WO | WO-2016/126995 A1 | 8/2016 |
| WO | WO-2016/127000 A1 | 8/2016 |
| WO | WO-2016/127002 A1 | 8/2016 |
| WO | WO-2016/130589 A2 | 8/2016 |
| WO | WO-2016/130806 A2 | 8/2016 |
| WO | WO-2016/138017 A1 | 9/2016 |
| WO | WO-2016/141236 A1 | 9/2016 |
| WO | WO-2016/145142 A1 | 9/2016 |
| WO | WO-2016/154096 A1 | 9/2016 |
| WO | WO-2016/161374 A1 | 10/2016 |
| WO | WO-2016/164896 A2 | 10/2016 |
| WO | WO-2016/167780 A1 | 10/2016 |
| WO | WO-2016168592 A2 | 10/2016 |
| WO | WO-2016/209862 A1 | 12/2016 |
| WO | WO-2017/004261 A1 | 1/2017 |
| WO | WO-2017/011276 A1 | 1/2017 |
| WO | WO-2017/011286 A1 | 1/2017 |
| WO | WO-2017/015109 A1 | 1/2017 |
| WO | WO-2017/015555 A1 | 1/2017 |
| WO | WO-2017/015575 | 1/2017 |
| WO | WO-2017/015575 A1 | 1/2017 |
| WO | WO-2017/019660 A1 | 2/2017 |
| WO | WO-2017/023660 A1 | 2/2017 |
| WO | WO-2017/032726 A1 | 3/2017 |
| WO | WO-2017/035340 A1 | 3/2017 |
| WO | WO-2017/040078 A1 | 3/2017 |
| WO | WO-2017/055423 A1 | 4/2017 |
| WO | WO-2017/059411 A1 | 4/2017 |
| WO | WO-2017/059446 A1 | 4/2017 |
| WO | WO-2017/062862 A2 | 4/2017 |
| WO | WO-2017/067970 A1 | 4/2017 |
| WO | WO-2017/068087 A1 | 4/2017 |
| WO | WO-2017/079291 A1 | 5/2017 |
| WO | WO-2017/081223 A1 | 5/2017 |
| WO | WO-2017/015555 A8 | 6/2017 |
| WO | WO-2017/157672 A1 | 9/2017 |
| WO | WO-2017/157899 A1 | 9/2017 |
| WO | WO-2017/160741 A1 | 9/2017 |
| WO | WO-2017/165489 A1 | 9/2017 |
| WO | WO-2017157672 A1 | 9/2017 |
| WO | WO-2017/178656 A1 | 10/2017 |
| WO | WO-2017180835 A1 | 10/2017 |
| WO | WO-2017/192679 | 11/2017 |
| WO | WO-2017/192679 A1 | 11/2017 |
| WO | WO-2017/194498 A1 | 11/2017 |

(56) References Cited

FOREIGN PATENT DOCUMENTS

| WO | WO-2017/194664 | | 11/2017 |
| WO | WO-2017/194664 | A1 | 11/2017 |
| WO | WO-2017/198775 | A1 | 11/2017 |
| WO | WO-2017/210647 | A1 | 12/2017 |
| WO | WO-2017/221883 | A1 | 12/2017 |
| WO | WO-2018/022473 | A1 | 2/2018 |
| WO | WO-2018/067973 | A1 | 4/2018 |
| WO | WO-2018/098264 | A1 | 5/2018 |

OTHER PUBLICATIONS

Masaru Kihara et al., "New Norepinephrine Potentiators Synthesis and Structure-Activity Relationships of a Series of 4-Phenyl-1, 2, 3, 4-tetrahydroisoquinolin-4-ols.", Chemical & Pharmaceutical Bulletin, vol. 42, No. 1, Jan. 1994, pp. 67-73.
Harrie J.M. Gijsen et al., "Development of two diastereoselective routes towards trans-4-aminomethyl-piperidin-3-ol building blocks", Tetrahedron, vol. 64, No. 10, 2008, pp. 2456-2464.
Search report from International Patent Appl. No. PCT/JP2011/071559, mail date is Dec. 20, 2011.
International Preliminary Report on Patentability Appl. No. PCT/JP2011/071559, mail date is Apr. 25, 2013 (English and Japanese versions).
Extended European search report issued with respect to European application No. 11826893.7, mail date is Apr. 25, 2014.
Steen Uldall Hansen et al., "Azaribofuranoside Analogues as Designed Inhibitors of Purine Nucleoside Phosphorylase. Synthesis and Biological Evaluation", Acta Chemics Scandinavica, vol. 52, 1998, pp. 1214-1222.
Chui Ming Wong, "Synthesis of anisomycin. Part I. The stereospecific synthesis of N-benzoyl-2-(p-methoxybenzyl)-3-hydroxy-4-carboxamido pyrrolidine and the absolute configuration of anisomycin", Canadian journal of Chemistry, vol. 46, 1968, pp. 1101-1104.
Ganguly, A.K. et al., Structure of Halomicin B, J.C.S. Chem. Comm., 395-396 (1974).
Adams, S.P. et al., Hindered dialkylamino nucleoside phosphite reagents in the synthesis of two DNA 51-mers, Journal of the American Chemical Society, 105(3): 661-663 (1983).
Adarsh, et al., Organelle Specific Targeted Drug Delivery—A Review, International Journal of Research in Pharmaceutical and Biomedical Sciences, 2(3): 895-912 (2011).
Agrawal, S. And Tang, J.Y., GEM 91—an antisense oligonucleotide phosphorothioate as a therapeutic agent for AIDS, Antisense Research and Development, 2(4):261-266 (1992).
Agrawal, S. et al., Mixed-backbone oligonucleotides as second generation antisense oligonucleotides: In vitro and in vivo studies, Proc. Natl. Acad. Sci. USA, 94: 2620-2625 (1997).
Aldaye, F.A. et al., Assembling materials with DNA as the guide, Science, 321(5897): 1795-1799 (2008).
Aldrich Chemical Co. Catalog, 2007-2008 Issue, only p. 1719 supplied: see first full entry at col. 1 (S-methyl methanethiosulfonate), Milwaukee, WI.
Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).
Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).
Almer, et al. Solid Support Synthesis of all-Rp-oligo(ribonucleoside phosphorothioate)s, Nucleic Acids Research 24(19): 3811-3820 (1996).
Almer, H. et al., Synthesis of Diribonucleoside Phosphorothioates via Sterospecific Sulfurization of H-Phosphonate Diesters, J. Org. Chem., 57(23): 6163-6169 (1992).
Altschul, S.F. et al., Basic local alignment search tool, Journal of Molecular Biology, 215(3):403-410 (1990).
Altschul, S.F. et al., Gapped Blast and Psi-Blast: a new generation of protein database search programs, Nucleic Acids Research, 25(17):3389-3402 (1997).
Alul, R.H. et al., Oxalyl-CPG: a labile support for synthesis of sensitive oligonucleotide, Nucleic Acids Research, 19(7):1527-1532 (1991).
Alvarez, K. et al., Photocleavable Protecting Groups as Nucleobase Protections Allowed the Solid-Phase Synthesis of Base-Sensitive SATE-Prooligonucleotides, Journal of Organic Chemistry, 64(17): 6319-6328(1999).
Amarzguioui et al., Tolerance for mutations and chemical modifications in a siRNA, Nucleic Acids Research 31(2): 589-595 (2003).
Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).
Athyros, V.G. et al., Antisense technology for the prevention or the treatment of cardiovascular disease: the next blockbuster?, Expert Opin. Investig. Drugs, 17(7): 969-72 (2008).
Ausin, C. et al., Assesment of heat-sensitive thiophosphate protecting groups in the development of thermolytic DNA oligonucleotide prodrugs, Tetrahedron, 66(1):68-79 (2010).
Bachelin et al., Structure of a Stereoregular Phosphorothioate DNA/RNA duplex, Nat. Struct. Biol., 5(4): 271-276 (1998).
Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).
Ballas, Z.K. et al., Induction of NK Activity in Murine and Human Cells by CpG Motifs in Oligodeoxynucleotides and Bacterial DNA, J. Immunoll., 57: 1840-1845 (1996).
Barber, I. et al., The Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).
Barber, I. et al., The Prooligonucleotides Approach II: Synthesis and stability studies of chimeric oligonucleotide models, Bioorganic and Medicinal Chemistry Letters, 5(14):1441-1444 (1995).
Barnes, P.J. and Peterson, S. Efficacy and Safety of Inhaled Corticosteroids in Asthma, Am. Rev. Respir. Dis., 148: SI-S26 (1993).
Battistini et al., Stereoselective Synthesis of Cyclic Dinucloetide Phosphorothioates, Tetrahedron, 49(5): 1115-1132 (1993).
Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).
Beal, P.A. et al., Second Structural Motif for Recognition of DNA by Oligonucleotide-Directed Triple-Helix Formation, Science, 251: 1360-1363 (1991).
Beaucage, S.L. and Iyer, R.P., Advances in the Synthesis of Oligonucleotides by the Phosphoramidite Approach, Tetrahedron, 48(12):2223-2311 (1992).
Benner, S.A. and Sismour, A.M., Synthetic biology, Nature Reviews Genetics, 6(7):533-543 (2005).
Berge, S.M. et al., Pharmaceutical salts, J. Pharm. Sci., 66(1):1-19 (1997).
Besch, R. et al, Specific Inhibition of ICAM-1 Expression Mediated by Gene Targeting with Triplex-forming Oligonucleotides, J. Biol. Chem., 277(26): 32473-32479 (2002).
Bisbal, C. And Silverman, R.H., Diverse functions of RNase L and implication in pathology, Biochimie, 89(6-7):789-798 (2007).
Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).
Bock, L.C. et al., Selections of single-stranded DNA molecules that bind and inhibit human thrombin, Nature, 355: 564-566 (1992).
Bode, C. et al. CpG DNA as a vaccine adjuvant, Expert Rev. Vaccines, 10(4): 499-511 (2011).

(56) References Cited

OTHER PUBLICATIONS

Bodor, N. et al., A convenient synthesis of (acyloxy)alkyl .alpha.-ethers of phenols, The Journal of Organic Chemistry, 48(26):5280-5284 (1983).
Bohringer, M. et al., Why Pentose and not Hexose Nucleic Acids? Part II: Oligonucleotides of 2'3'-dideoxy-β-d-glucopyranosyl ('homo-DNA') production, Helvetica Chimica Acta, 75:1416-1477 (1992).
Bologna, J. et al., Uptake and Quantification of Intracellular Concentration of Lipophilic Pro-Oligonucleotides in HeLa Cells, Antisense and Nucleic Acid Drug Development, 12(1):33-41 (2002).
Boudreau, R.L. et al., Nonallele-specific silencing of mutant and wild-type huntingtin demonstrates therapeutic efficacy in Huntington's disease mice, 17(6): 1053-1063 (2009).
Braasch et al., RNA Interference in Mammalian Cells by Chemically-Modified RNA, Biochemistry 42(26): 7967-7975 (2003).
Brooks, P.C. et al., Insulin-like Growth Factor Receptor Cooperates with Integrin αvβ5 to Promote Tumor Cell Dissemination in Vivo, The Journal of Clinical Investigation, 99(6):1390-1398 (1997).
Brown, J.W.S. and Simpson, C.G., Splice Site Selection in Plant Pre-mRNA Splicing, Ann. Rev. Plant Physiol. Plant Mol. Biol., 49: 77-95 (1998).
Bundgaard, H., (C) Means to Enhance Penetration. (1) Prodrugs as a means to improve the delivery of peptide drugs, Advanced Drug Delivery Reviews, 8:1-38 (1992).
Bundgaard, H., Design and Application of Prodrugs, A Textbook of Drug Design and Development, Edited by Krogsgaard-Larsen, P. and Bundgaard, H., Chapter 5: 113-191 (1991).
Bundgaard, H., Design of Prodrugs, Elsevier, 7-9 and 21-24 (Chapter 1) (1985).
Bunnell. B.A. et al., Targeted Delivery of Antisense Oligonucleotides by Molecular Conjugates, Somatic Cell and Molecular Genetics, 18(6):559-569 (1992).
Burgers et al., Absolute configuration of the diastereomers of adenosine 5' -O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
Carbone, G.M. et al., Selective inhibition of transcription of the Ets2 gene in prostate cancer cells by a triplex-forming oligonucleotide, Nucl. Acid. Res., 31: 833-843 (2003).
Carrillo, H., and Lipman, D.J., the multiple sequence alignment problem in biology, SIAM J. Appl. Math., 48:1073-1082 (1988).
CAS RN 78-96-6, Entered STN: Nov. 16, 1984.
Chatgilialoglu, C. and Snieckus, V., Chemical Synthesis: Gnosis to Prognosis, Kluwer Academic, 293-340 (1996).
Check, E., RNA interference: hitting the on switch, Nature, 448(7156): 855-858 (2007).
Chiu, Y. And Rana, T.M., siRNA function in RNAi: A chemical modification analysis, RNA, 9(9):1034-1048 (2003).
Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Clark, J.H, Flouride IOn as a Base in Organic Synthesis, Chemical Reviews, 1980 American Chemical Society 80(5): 429-452 (1980).
Communication Relating to the Results of the Partial International Search of PCT/IB2015/000395, Annex to Form PCT/ISA/206, 3 pages (Aug. 24, 2015).
Conway, N., The introduction of reporter groups at multiple and/or specific sites in DNA containing phosphorothioate diesters, Nucleic Acids Research, 43-44 (1989).
Cooney, M., et al., Site-Specific Oligonucleotide Binding Represses Transcription of the Human c-myc Gene in Vitro, Science, 241: 456-459 (1988).
Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, Chemical Reviews, 64(4): 317-352, (1964).
Crary, S.M. et al., Specific phosphorothioate substitutions probe the active site of *Bacilus subtilis* ribonuclease P, RNA, 8:933-947 (2002).
Cullen, K.A. et al., Ambulatory surgery in the United States, 2006, National Health Statistics Reports, 11: 1-28 (Jan. 28, 2009—Revised Sep. 4, 2009).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Davis, B.G. et al., Altering the specificity of subtilisin bacillus lentus through the introduction of positive charge at single amino acid sites, Bioorganic & Medicinal Chemistry, 7(11): 2303-2311 (1999).
Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).
Devereux, J. et al., A comprehensive set of sequence analysis programs for the VAX, Nucleic Acids Research, 12(1):387-395 (1984).
Dietz, G.P.H. et al., Delivery of bioactive molecules into the cell: the Trojan horse approach, Molecular and Cellular Neuroscience, 27(2): 85-131 (2004).
Djukanovic, R. et al., Mucosal Inflammation in Asthma, Am. Rev. Respir. Dis., 142: 434-457 (1990).
Dorman et al., Synthesis of Oligodeoxynucleotides and Oligodeoxynucleotide Analogs using Phosphoramidite Intermediates, Tetrahedron, 40(1):95-102 (1984).
Dua, P. et al., Patents on SELEX and therapeutic aptamers, Recent Patents on DNA & Gene Sequences, 2(3):172-186 (2008).
Eaton, W.A. et al., Submillisecond kinetics of protein folding, Curr. Opin. Chem. Biol., 1:10-14 (1997).
Eckstein, F. Phosphorothioates, Essential Components of Therapeutic Oligonucleotides, Nucleic Acid Therapeutics, 1-14 (2014).
Eckstein, F., Oligonucleotides and Analogues A Practical Approach, IRL Press, 1-24 (1991).
Egli, M. et al., Crystal structure of homo-DNA and nature's choice of pentose over hexose in the genetic system, Journal of the American Chemical Society, 128(33):10847-56 (2006).
El Harchaoui, K. et al., Current and future pharmacologic options for the management of patients unable to achieve low-density lipoprotein-cholesterol goals with statins, Am. J. Cardiovasc. Drugs, 8(4): 233-242 (2008).
Elbashir, S.M. et al., Duplexes of 21-nucleotide RNAs mediate RNA interference in cultured mammalian cells, Nature, 411: 494-498 (2001).
Elbashir, S.M. et al., Functional anatomy of siRNAs for mediating efficient RNAi in Drosophila melanogaster embryo lysate, The EMBO Journal, 20(23): 6877-6888 (2001).
Ellington, A.D. and Szostak, J.W., In vitro selection of RNA molecules that bind specific ligands, Nature, 346: 818-822 (1990).
Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: 1-10 (2015).
Epton, R., Innovation and Perspectives in Solid Phase Synthesis, Peptides, Proteins and Nucleic Acids, 21:157-162 (1994).
Eschenmoser, A. et al., Why pentose- and not hexose nucleic acids? Introduction to the problem, conformational analysis of oligonucleotide single strands containing 2', 3'-dideoxyglucopyranosyl building blocks ('homo-DNA'), and reflections on the conformation of A- and B-DNA, Helvetica Chimica Acta, 75:218-259 (1992).
Eschenmoser, A., Chemical etiology of nucleic acid structure, Science, 284(5423):2118-24 (1999).

(56) References Cited

OTHER PUBLICATIONS

Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).
Famulok, M. Oligonucleotide aptamers that recognize small molecules, Curr. Opin. Struct. Biol., 9: 324-329 (1999).
Fendrich et al., Determination of the Absolute P-configuration of a Phthalidyl[Phosphonate Thymidine-Thymidine Dimer, Nucleosides Nucleotides Nucleic Acids., 22(5-8): 1127-1129 (2003).
Ferreira, F. et al., Lewis acid deprotection of silyl-protected oligonucleotides and base-sensitive oligonucleotide analogues, Tetrahedron Letters, 45(33):6287-6290 (2004).
File Registry on STN, RN 18217-60-2, Entered STN: Nov. 16, 1984.
File Registry on STN, RN 871246-91-2, Entered STN: Jan. 5, 2006.
Fire, A. et al., Potent and specific RNA interference by double-stranded RNA in Caenorhadbditis elegans, Nature, 391: 806-811 (1998).
Forster, A.C. and Symons, R.H. Self-cleavage of plus and minus RNAs of a virusoid and a structural model for the active sites, Cell, 49(2): 211-220 (1987).
Forster, A.C. and Symons, R.H. Self-Cleavage of Virusoid RNA is performed by the Proposed 55-Nucleotide Active Site, Cell, 50: 9-16 (1987).
Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologist's Perspective, Toxicology Pathology, 43: 78-89 (2015).
Frederiksen, J.K. et al., Separation of RNA Phosphorothioate Oligonucleotides by HPLC, Methods of Enzymology, 468:289-309 (2009).
Freier, S.M. et al., Improved free-energy parameters for predictions of RNA duplex stability, Proc. Nat. Acad. Sci. USA, 83: 9373-9377 (1986).
Froehler, B.C. et al., Synthesis of DNA via deoxynucleoside H-phosphonate intermediates, Nucleic Acids Research, 14(13): 5399-5407 (1986).
Fujii et al., Acylphosphonates. 5.1A new method for stereospecific generation of phosphorothioate via aroylphosphonate intermediate, Tetrahedron Letters, 27(8): 935-938 (1986).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).
Gauglitz, G.G. et al., Hypertrophic Scarring and Keloids: Pathomechanisms and Current Emerging Treatment Strategies, Mol. Med., 17(1-2): 113-125 (2011).
Goraczmiak, R. et al., Gene silencing by synthetic U1 Adaptors, Nature Biotechnology 27(3): 257-263 (2008).
Gosselin, G. et al., New insights regarding the potential of the pronucleotide approach in antiviral chemotherapy, 43(1):195-208 (1996).
Gough, G.R. et al., Recovery and recycling of synthetic units in the construction of oligodeoxyribonucleotides on solid supports, Tetrahedron Letters, 22(42): 4177-4180 (1981).
Graham, M.J. et al., Antisense inhibition of proprotein convertase subtilisin/kexin type 9 reduces serum LDL in hyperlipidemic mice, J. Lipid Res., 48(4): 763-767 (2007).
Grajkowski, A. et al., Design and Development of Thermolytic DNA Oligonucleotide Prodrugs, Annals of the New York Academy of Sciences, 1058:26-38 (2005).

Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3): 805-815 (2007).
Grajkowski, A. et al., Thermolytic CpG-containing DNA oligonucleotides as potential immunotherapeutic prodrugs, Nucleic Acids Research, 33(11):3550-3560 (2005).
Green, L.S. et al., Inhibitory DNA Ligands to Platelet-Derived Growth Factor B-Chain, Biochemistry, 35: 14413-14424 (1996).
Green, L.S. et al., Nuclease-resistant nucleic acid ligands to vascular permeability factor/vascular endothelial growth factor, Chem. Biol., 2(10): 683-695 (1995).
Griffiths-Jones, S. et al., miRBase: microRIVA sequences, targets and gene nomenclature, Nucleic Acids Research, 34 (Database Issue): D140-D144 (2006).
Griffiths-Jones, S. The microRNA Registry, Nucleic Acids Research, 32 (Database Issue): D109-D111 (2004).
Groebke, K. et al., Why pentose and not hexose nucleic acids? Part V. Purine-purine pairing in homo-DNA: guanine, isoguanine, 2,6-diaminopurine and xanthine. Helvetica Chimica Acta. 81: 375-474 (1998).
Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).
Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).
Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).
Guga et al., Unusual Thermal Stability of RNA/[RP-PS]-DNA/RNA Triplexes Containing a Homopurine DNA Strand, Biophys J., 92(7): 2507-2515 (2007).
Guga, P. and Stec, W.J., Synthesis of Phosphorothioate Oligonucleotides with Stereodefined Phsphorothioate Linkages, Current Protocols in Nucleic Acid Chemistry, Unit 4.17: 4.17.1-4.17.28 (2003).
Guga, P., P-chiral oligonucleotides in biological recognition processes, Current Topics in Medicinal Chemistry, 7:695-713 (2007).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).
Hacia, J.G. et al., Phosphorothioate oligonucleotide-directed triple helix formation, Biochemistry, 33:5367-5369 (1994).
Hanagata, N., Structure-dependent immunostimulatory effect of CpG oligodeoxynucleoties and their delivery system, Int. J. Nanomedicine, 7: 2181-95 (2012).
Harper, S.Q. et al., RNA interference improves motor and neuropathological abnormalities in a Huntington's disease mouse model, Proc. Natl. Acad. Sci. USA, 102(16): 5820-5825 (2005).
Hau, P. et al., Results of G004, a phase IIb actively controlled clinical trial with the TGF-b2 targeted compound AP 12009 for recurrent anaplastic astrocytoma, Journal of Clinical Oncology, 2006 ASCO Annual Meeting Proceedings (Post-Meeting Edition), 24(18, Jun. 20 Supplement): 1566 (2006).
Hayashi, S. et al., Studies on Antitumor Substances, Chemical & Pharmaceutical Bulletin, 12(11): 1271-1276 (1964).
Henry, A.A. and Romesberg, F.E., Beyond A, C, G and T: augmenting nature's alphabet, Current Opinion in Chemical Biology, 7(6): 727-733 (2003).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Herbert, B-S. et al., Nonradioactive detection of telomerase activity using the telomeric repeat amplification protocol, Nat. Protoc., 1(3): 1583-1590 (2006).

(56) References Cited

OTHER PUBLICATIONS

Herdewijn, Oligonucleotide Synthesis, Methods in Molecular Biology, 288: 1-435 (2005).
Heuberger, B.D. and Switzer, C., A Pre-RNA Candidate Revisited: Both Enantiomers of Flexible Nucleoside Triphosphates are DNA Polymerase Substrates, Journal of the American Chemical Society, 130(2):412-413 (2008).
Higuchi, T. et al., Pro-drugs as Novel Delivery Systems, ACS Symposium Series, 14 (1975).
Hirao, I., Unnatural base pair systems for DNA/RNA-based biotechnology, Current Opinion in Chemical Biology,10:622-627 (2006).
Hohjoh, H., Disease-Causing Allele-Specific Silencing by RNA Interference, Pharmaceuticals, 6: 522-535 (2013).
Hunziker, J. et al., Why Pentose-And Not Hexose-Nucleic Acids? Part III. Oligo(2',3'-dideoxy-β-D-glucopyranosyl)nucleotides. ('Homo-DNA'): Base-Pairing Properties, Helvetica Chimica Acta, 76(1):259-352 (1993).
Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).
International Preliminary Report on Patentability and Written Opinion of the Searching Authority for PCT/JP2011/055018 (Oct. 11, 2012) with English Translation thereof.
International Preliminary Report on Patentability for Application No. PCT/JP2010/065900, 6 pages (dated Mar. 29,2012).
International Preliminary Report on Patentability for Application No. PCT/JP2010/065900, 7 pages (dated Apr. 19,2012). (English Translation).
International Preliminary Report on Patentability for PCT/JP2013/004303, 1 page (dated Jan. 13, 2015).
International Search Report for PCT/IB2009/007923, 4 pages (dated Sep. 6, 2010).
International Search Report for PCT/IB2015/000395, 7 pages (dated Oct. 30, 2015).
International Search Report for PCT/JP2010/065900, 1 page (dated Sep. 15, 2010).
International Search Report for PCT/JP2011/55018 (dated Mar. 29, 2011).
International Search Report for PCT/JP2013/004303, 3 pages (dated Aug. 13, 2013).
International Search Report for PCT/US2010/041068, 1 page (dated Sep. 1, 2010).
International Search Report for PCT/US2011/064287, 2 pages (dated Apr. 12, 2012).
International Search Report for PCT/US2012/046805, 2 pages (dated Sep. 19, 2012).
International Search Report for PCT/US2013/050407, 5 pages (dated Jan. 9, 2014).
Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.
Isis Pharmaceuticals, Intellectual Property: Capturing Value From Innovation, Isis' Annual Meeting of Stockholders and Open House, Intellectual Property Poster, 1 page (2012). Received from Internet <http://www.isispharm.com/Site_Gfx/pdf/2012_Annual_Meeting_IP_Poster.pdf>.
Iwamoto et al., Stereocontrolled Synthesis of H-phosphonate DNA, Nucleic Acids Symposium Series, (50):159-60 (2006).
Iwamoto, N. et al., Stereocontrolled solid-phase synthesis of oligonucleoside H-phosphonates by an oxazaphospholidine approach, Angewandte Chemie International Edition, 48(3):496-499 (2009).
Iyer, R.P. et al., A novel nucleoside phosphoramidite synthon derived from 1 R, 2S-ephedrine, Tetrahedron Asymmetry 6(5):1051-1054 (1995).
Iyer, R.P. et al., Acyloxyaryl prodrugs of oligonucleoside phosphorothioates, Bioorganic and Medicinal Chemistry Letters, 6(16):1917-1922 (1996).
Iyer, R.P. et al., Bioreversible oligonucleotide conjugates by site-specific derivatization, Bioorganic and Medicinal Chemistry Letters, 7:871-876 (1997).
Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).
Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).
Iyer, R.P., et al., Prodrugs of Oligonucletides: The Acyloxyalkyl Esters of Oligodeoxyribonucleoside Phosphorothioates, Bioorganic Chemistry, 23:1-21 (1995).
Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).
Jiang, J. et al., Allele-Specific Silencing of Mutant Myh6 Transcripts in Mice Suppresses Hypertrophic Cardiomyopathy, Science, 342: 111-114 (2013).
Jin et al., A Stereoselective Synthesis of Dinucleotide Boranophosphate, Using Chiral Indole-Oxazaphosphorine Intermediates, Tetrahedron Letters, 39: 6433-6436 (1998).
Jin et al., Stereoselective Synthesis of Dithymidine Phosphorothioates Using Xylose Derivatives as Chiral Auxiliaries, J. Org. Chem., 63(11): 3647-3654 (1998).
Johansson et al., Studies towards synthesis of dinucleoside arylphosphonates with metal complexing properties, Nucleosides Nucleotides & Nucleic Acids, 22(5-8): 1459-61 (2003).
Johansson et al., Synthesis of dinucleoside pyridylphosphonates involving palladium(o)-catalysed phosphorus-carbon bond formation as a key step, Chem. Commun., 2564-2565 (2001).
Johansson et al., the case for configurational stability of H-phosphonate diesters in the presence of diazabicyclo[5.4.0]undec-7-ene (DBU), Bioorg Med Chem., 9(9): 2315-22 (2001).
Jopling, C.L. et al., Modulation of Hepatitis C Vicus RNA Abundance by a Liver-Specific MicroRNA, Science, 309: 1577-1581 (2005).
Joyce, G.F. et al., the case for an ancestral genetic system involving simple analogues of the nucleotide, Proceedings of the National Academy of Sciences, 84:4398-4402 (1987).
Joyce, G.F. The antiquity of RNA-based evolution, Nature, 418(6894): 214-221 (2002).
Kakeya, N. et al., Studies on Prodrugs of Cephalosporins. I. Synthesis and Biological Properties of Glycyloxybenzoyloxymethyl and Glycylaminobenzoyloxymethyl Esters of 7 -[2-(2-Aminothiazol-4-yl)-(Z)-2-methoxyiminoacetamido]-3-methyl-3-cephem-4-carboxylic Acid, Chem. Pharm. Bull., 32(2): 692-698 (1984).
Kamada, A.K. et al., Issues in the Use of Inhaled Glucocorticoids, Am. J. Respir. Crit. Care. Med., 153: 1739-1748 (1996).
Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).
Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).
Kers et al., A new type of nucleotide analogue with 4-pyridylphosphonate internucleotide linkage, Tetrahedron Letters, 40(22): 4263-4266 (1999).
Kim, N.W. et al., Specific Association of Human Telomerase Activity with Immortal Cells and Cancer, Science, 226: 2011-2015 (1994).
Kim, S-H. and Cech, T.R., Three-dimensional model of the active site of the selfsplicing rRNA precursor of Tetrahymena, Proc. Natl. Acad. Sci. U S A., 84(24): 8788-8792 (1987).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Kool, E.T., Replacing the Nucleobases in DNA with Designer Molecules, Accounts of Chemical Research, 35:936-943 (2002).

(56) References Cited

OTHER PUBLICATIONS

Kordasiewicz, H.B. et al., Sustained therapeutic reversal of Huntington's disease by transient repression of huntingtin synthesis, Neuron, 74(6): 1031-1044 (2012).

Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).

Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).

Koziolkewicz et al., Stereodifferentiation-the effect of P chirality of oligo(nucleoside phosphorothioates) on the activity of bacterial RNase H, Nucl. Acids Res., 23(24): 5000-5005 (1995).

Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).

Kraszewski et al., Studies on Reactions of Nucleoside H-phosphonates with Bifunctional Reagents. Part 1. Reaction with amino alcohols, J. Chem. Soc., Perkin Trans., 1: 1699-1704 (1993).

Krieg, A.M. et al., CpG motifs in bacterial DNA trigger direct B-cell activation, Nature, 374: 546-549 (1995).

Krieg, A.M. et al., P-Chirality-Dependent Immune Activiation by Phosphorothioate CpG Oligodeoxynucleotides, Oligonucleotides, 13:491-499 (2003).

Krueger, a.T. et al., Synthesis and properties of size-expanded DNAs: toward designed, functional genetic systems, Accounts of Chemical Research, 40:141-150 (2007).

Krutzfeldt, J. et al., Silencing of microRNAs in vivo with 'antagomirs', Nature, 438: 685-689 (2005).

LaPLANCHE, L.A. et al., Phosphorothioate-modified oligodeoxyribonucleotides. III. NMR and UV spectroscopic studies of the Rp-Rp, Sp-Sp, and Rp•Sp duplexes, [d(GGsAATI'CC)2, derived from diastereomeric 0-ethyl phosphorothioates, Nucleic Acids Research, 14(22): 9081-9093 (1986).

Latimer, L.J.P. et al, Synthetic repeating sequence DNAs containing phosphorothioates: nuclease sensitivity and triplex formation, Nucleic Acids Research, 17(4): 1549-1561 (1989).

Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).

Lavergne, T. et al., A Base-Labile Group for 2'-OH Protection of Ribonucleosides: A Major Challenge for RNA Synthesis, Chem. Eur. J, 14, 9135-9138 (2008).

Lesnikowski et al., Studies on Stereospecific Formation of P-Chiral Internucleotide Linkage. Synthesis of (RP, RP)- and (SP, SP)-Thymidylyl (3', 5') Thymidylyl (3', 5') Thymidine DI (O,O-Phosphorothioate) Using 2-Nitrobenzyl Group as a New S-Protection, Tetrahedron Letters 30(29) 3821-3824 (1989).

Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).

Li L.C., Small RNA Mediated Gene Activation, RNA and the Regulation of Gene Expression: A Hidden Layer of Complexity, Edited by Kevin V. Morris, Chapter 13, Caister Academic Press (2008).

Li, L-C. et al., Small dsRNAs induce transcriptional activation in human cells, PNAS, 103(46): 17337-17342 (2006).

Li-Tsang, C.W. et al., Prevalence of hypertrophic scar formation and its characteristics among the Chinese population, Burns, 31: 610-616 (2005).

Liang, X-h. et al., Identification and characterization of intracellular proteins that bind oligonucleotides with phosphorothioate linkages, Nucleic Acids Research, 43(5): 2927-2945, Supplemental Data pp. 1-20 (2015).

Lima, W. et al., Single-Stranded ssRNAi Activate RNAi in Animals, Cell, 150: 883-894 (2012).

Lima, W.F. et al., the influence of antisense oligonucleotide-induced RNA structure on *Escherichia coli* RNase H1 activity, J. Biol. Chem., 272(29):18191-9 (1997).

Limbach, P.A. et al., Summary: the modified nucleosides of RNA, Nucleic Acids Research, 22(12):2183-2196 (1994).

Lin et al., Synthesis and resolution of dinucleotide (TpAZT) phosphoramidates, Synthetic Commun., 33(14): 2553-2562 (2003).

Liu, W. et al., Increased Steady-State Mutant Huntingtin mRNA in Huntington's Disease Brain, Journal of Huntington's Disease 2: 491-500 (2013).

Lu, X. et al., Antisense-Mediated Inhibition of Human Immunodeficiency Virus (HIV) Replication by Use of an HIV Type 1-Based Vector Results in Severely Attenuated Mutants Incapable of Developing Resistance, Journal of Virology, 78(13): 7079-7088 (2004).

Lu, Y. And Just, G., Stereoselective synthesis of dithymidine phosphorothioates using d-xylose derived chiral auxiliaries, Tetrahedron, 57(9):1677-1687 (2001).

Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).

Lu, Y., Recent advances in the stereocontrolled synthesis of antisense phosphorothioates, Mini Reviews in Medicinal Chemistry, 6(3): 319-330 (2006).

Machine Translation of JP 2010-265304 (2010). <http://dossier1.ipdl.inpit.go.jp/AIPN/odse_top_dn.ipdl?NOOOO=7400>.

Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).

Machytka et al., Synthesis and NMR characterization of diastereomeric CPSMeG derivatives, Nucleosides Nucleotides Nucleic Acids., 19(5-6): 903-15 (2000).

Maher III, L.J., et al., Inhibition of DNA Binding Proteins by Oligonucleotide-Directed Triple Helix Formation, Science, 245: 725-730 (1989).

Mann, M.J. et al., Therapeutic applications of transcription factor decoy oligonucleotides, J. Clin. Invest., 106:1071-1075 (2000).

Mannironi, C. et al., In Vivo Selection of Dopamine RNA Ligands, Biochemistry, 36: 97269734 (1997).

Martin, P., a New Access to 2'-O-alkylated Ribonucleosides and Properties of 2'-O-Alkylated Oligoribonucleotides, Helv. Chim. Acta., Abstract Only, 78: 486-504 (1995).

Martin, P., Stereoselective Synthesis of 2'-O-(2-Methoxyethyl)ribonucleosides: Neighboring-Group Participation of the Methoxyethoxy Group in the Ribosylation Step, Helv. Chim. Acta, 79: 1930-1938 (1996).

Masahiro, T. et al., Nematicidal and antimicrobial constituents from Allium grayi Regel and Allium fistulosum L. var. caespitosum, Agricultural and Biological Chemistry, 52(9): 2383-2385 (1988).

Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).

Maung, J. et al., Alternatives to 1-H-tetrazole in the preparation of phosphonate diesters and phosphonamidates from phosphonyl dichlorides, Tetrahedron Lett., 45: 6497-6499 (2004).

Mauritz, R.P. et al., Elucidation of the Hydrolytical Properties of α-Hydroxybenzylphosphonates as a New Potential Pro-Oligonucleotide Concept, Nucleosides and Nucleotides, 18(6-7):1417-1418 (1999).

Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides and Nucleotides, 16(7-9):1209-1212 (1997).

McBRIDE, J.L. et al., Prelinical Safety of RNAi-Mediated HTT Suppression in the Rhesus Macaque as a Potential Therapy for Huntington's Disease, Molecular Therapy, 19: 1-11 (2011).

(56) References Cited

OTHER PUBLICATIONS

Medical News Today, AVI BioPharma Announces FDA Clears IND Applications for Clinical Trials of RNA Therapeutic Agents for Treatment of Ebola and Marburg Viruses, Accessed Apr. 2, 2015, 2 pages (Dec. 30, 2008).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).
Methods in Enzymology, Edited by Widder, K. and Green, R., Drug and Enzyme Targeting, Academic Press, 112: 309-396 (1985).
Mignet, N. et al., Synthesis and evaluation of glucuronic acid derivatives as alkylating agents for the reversible masking of internucleoside groups of antisense oligonucleotides, Carbohydrate Research, 303:17-24 (1997).
Mignet, N. et al., The Prooligonucleotide Approach. V: Influence of the phosphorus atom environment on the hydrolysis of enzymolabile dinucleoside phosphotriesters, Bioorganic and Medicinal Chemistry Letters, 7(7):851-854 (1997).
Milkowski, J.D. et al., Thiol Protection with the Acetamidomethyl Group: S-Acetamidomethyl-l-cysteine Hydrochloride, Organic Syntheses, 6: 5 (1988).
Misaki, S et al., Dehydration of 2-Trifluoromethyl-3,3,3-Trifluoropropanil with Base, Journal of Flourine Chemistry 24: 531-533 (1984).
Monteys, A.M. et al., Single nucleotide seed modification restores in vivo tolerability of a toxic artificial miRNA sequence in the mouse brain, Nucleic Acids Res., 42(21): 13315-13327 (2014).
Morales-Rojas, H. And Kool, E.T., A porphyrin C-nucleoside incorporated into DNA, Organic Letters, 4(25):4377-4380 (2002).
Morcos, P.A., Achieving targeted and quantifiable alteration of mRNA splicing with Morpholino oligos, Biochem. Biophys. Res. Commun., 358(2): 521-527 (2007).
Morvan, F. et al., Cellular uptake and intracellular quantification of fluorescent labeled T20 Me-SATE prooligonucleotides, Nucleosides Nucleotides Nucleic Acids, 20(4-7):1165-1168 (2001).
Morvan, F. et al., Kinetics study of the biotransformation of an oligonucleotide prodrug in cells extract by matrix-assisted laser desorption/ionization time-of-flight mass spectrometry, Nucleosides, Nucleotides and Nucleic Acids, 20(2-4):1159-1163 (2001).
Morvan, F. et al., The Oligonucleotide Prodrug Approach: The Pro-Oligonucleotides, Pharmaceutical Aspects of Oligonucleotides, 79-97 (2000).
Moser, H. E. et al., Sequence-Specific Cleavage of Double Helical DNA by Triple Helix Formation, Science, 238: 645-650 (1987).
Nawrot et al., DNA Oligonucleotides Containing Stereodefined Phosphorothioate Linkages in Selected Positions, Current Protocols in Nucleic Acid Chemistry, Unit 4.34: 4.34.1-4.34.15 (2009).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).
Nowotny, M. et al., Structure of human RNase H1 complexed with an RNA/DNA hybrid: insight into HIV reverse transcription, Mol Cell, 28(2):264-76 (2007).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
O'Connell, D. et al., Calcium-dependent oligonucleotide antagonists specific for L-selectin, Proc. Natl. Acad. Sci. USA, 93: 5883-5887 (1996).
Ohgi, T. et al., A New RNA Synthetic Method with a 2'-O-(2-Cyanoethoxymethyl) Protecting Group, Organic Letters, 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., An oxazaphospholidine approach for the stereocontrolled synthesis of oligonucleoside phosphorothioates, Journal of the America Chemical Society, 125(27):83078317 (2003).
Oka, N. et al., Diastereocontrolled Synthesis of Dinucleoside Phosphorothioates Using a Novel Class of Activators, Dialkyl(cyanomethyl)ammonium Tetrafluoroborates, Journal of the American Chemical Society, 124(18):4962-4963 (2002).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).
Oka, N. et al., Stereocontrolled synthesis of dinucleoside boranophosphates by an oxazaphospholidine method, Nucleic Acids Symposium Series, (49): 131-132 (2005).
Oka, N. et al., Stereocontrolled synthesis of oligonucleoside phosphorothioates and PO/PS-chimeric oligonucleotides by using oxazaphospholidine derivaties, Nucleic Acids Symposium Series, 52: 335-336 (2008).
Oka, N. et al., Stereocontrolled Synthesis of Oligoribonucleoside Phosphorothioates by an Oxazaphospholidine Approach, Organic Letters, 11(4):967-970 (2009).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Otting, G. et al., Why Pentose- and Not Hexose-Nucleid Acids? Part IV. 'Homo-DNA': 1 H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).
Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).
Pan, Q-W. et al., New therapeutic opportunities for Hepatitis C based on small RNA, World J. Gastroenterol., 13(33): 4431-4436 (2007).
Parrish et al., Functional Anatomy of a dsRNA Trigger: Differential Requirement for the Two Trigger Strands in RNA Interference, Molecular Cell, 6:1077-1087 (2000).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Perrino, E. et al., New sulfurated derivatives of valproic acid with enhanced histone deacetylase inhibitory activity, Bioorganic & Medicinal Chemistry Letters, 18(6): 1893-1897 (2008).
Peyrottes, S. et al., SATE pronucleotide approaches: an overview, Mini-Reviews Medicinal Chemistry, 4(4):395-408 (2004).
Pfister, E.L. et al., Five siRNAs targeting three SNPs may provide therapy for three-quarters of Huntington's disease patients, 19(9): 774-778 (2009).
Pharmacology Review(s), Application Number: 203568Orig1s000, Center for Drug Evaluation and Research, Food and Drug Administration, Department of Health & Human Services, 2013.

(56) References Cited

OTHER PUBLICATIONS

Pitsch, S. et al., Reliable Chemical Synthesis of Oligoribonucleotides (RNA) with 2'-O-[(Triisopropylsilypoxy]methyl(2'-O-tom)-Protected Phosphoramidites, Helvetica Chimica Acta, 84: 3773-3795 (2001).
Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1571 (2005).
Poijarvi, P. et al., The chemical stability of S-(2-acylthioethyl) and S-acyloxymethyl protected thymidyly1-3',5'-thymidine phosphoromonothiolates and their deacylation products in aqueous solution, Nucleosides Nucleotides and Nucleic Acids, 20(1-2):77-91 (2001).
Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).
Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).
Poijarvi, P., Prodrug Approaches of Nucleotides and Oligonucleotides, Current Medicinal Chemistry, 13(28):3441-3465 (2006).
Pon, R. T., Solid-Phase Supports for Oligonucleotide Synthesis, Current Protocols in Nucleic Acid Chemistry, 3.1.1-3.1.28 (2000).
Potter et al, Stereospecificity of nucleases towards phosphorothioate-substituted RNA: stereochemistry of transcription by T7 RNA polymerase, Nucleinc Acids Research, 15(10): 4145-4162 (1987).
Potter, B.V.L. et al., Synthesis and Configurational Analysis of Dinucleoside Phosphate Isotopically Chiral at Phosphorus. Stereochmical Course of Penicillium citrum Nuclease P1 Reaction, Biochemistry, 22: 1369-1377 (1983).
Prakash, T.P. et al., 2'-O-[2-(Methylthio )ethyl]-Modified Oligonucleotide: An Analogue of 2'-O-[2-(Methoxy)-ethyl]-Modified Oligonucleotide with Improved Protein Binding Properties and High Binding Affinity to Target RNA, Biochemistry, 41: 11642-11648 (2002).
Prhavc, M. et al., 2'-O-[2-[2-(N,N-Dimethylamino)ethoxy]ethyl] Modified Oligonucleotides: Symbiosis of Charge Interaction Factors and Stereoelectronic Effects, Organic Letters, 5(12): 2017-2020 (2003).
Puri, N. et al, Targeted Gene Knockout by 2'-O-Aminoethyl Modified Triplex Forming Oligonucleotides, J. Biol. Chem., 276: 28991-28998 (2001).
Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).
Reese, C.B. and Yan, H., Solution phase synthesis of ISIS 2922 (Vitravene) by the modified H-phophane approach, J. Chem. Soc., Perkin Trans. I, 2619-2633 (2002).
Reither, S. and Jeltsch, A., Specificity of DNA triple helix formation analyzed by a FRET assay, BMC Biochemistry, 3: 9 pages (2002).
Revankar, G. R. and Rao, T.S., DNA with Altered Bases, DNA and Aspects of Molecular Biology, Comprehensive Natural Products Chemistry, 7.09: 313-339 (1999).
Robinson, D.S. et al., Predominant TH2-Like Bronchoalveolar T-Lymphocyte Population in Atopic Asthma, The New England Journal of Medicine, 326: 298-304 (1992).
Schoning, K.-U. et al., Chemical Etiology of Nucleic Acid Structure: The α-Threofuranosyl-(3'->2') Oligonucleotide System, Science, 290(5495):1347-1351 (2000).
Schultz, C., Prodrugs of Biologically Active Phospate Esters, Bioorganic and Medicinal Chemistry, 11(6):885-898 (2003).
Schulz, W.G. And Cai, S.L., Synthetic Genetics, Chemical and Engineering News, 5 (2012).
Seela et al, Diastereomerically pure Rp and Sp dinucleoside H-phosphonates. The stereochemical course of their conversion into P-methylphosphonates, phosphorothioates and [18O] chiral phosphates, Journal of Organic Chemistry, 56(12): 3861-3869 (1991).
Seidman, M.M. and Glazer, P.T. The potential for gene repair via triple helix formation, The Journal of Clinical Investigation, 112(4): 487-494 (2003).
Senn, J.J. et al., Non-CpG-Containing Antisense 2-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).
Sergueeva et al., Synthesis of Dithymidine Boranophosphates via Stereospecific Boronation of H-phosphonate Diesters and Assignment of their Configuration, Tetrahedron Letters, 40: 2041-2044 (1999).
Seth, P.P. et al., An Exocyclic Methylene Group Acts as a Bioisostere of the 2'Oxygen Atom in LNA, J. Am. Chem. Soc, 132(42): 14942-14950 (2010).
She, X. et al., Synergy between Anti-Endoglin (CD105) Monoclonal Antibodies and TGF-β in Suppression of Growth of Human Endothelial Cells, Int. J. Cancer, 108: 251-257 (2004).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Sierzchala et al., Oxathiaphospholane Method of Stereocontrolled Synthesis of Diribonucleoside 3', 5'—Phosphorotioates, Journal of Organic Chemistry 61(19): 6713-6716 (1996).
Silverman, R.H., A scientific journey through the 2-5A/RNase L system, Cytokine Growth Factor Reviews, 18(5-6):381-388 (2007).
Singhrao, S.K. et al., Increased Complement Biosynthesis by Microglia and Complement Activation on Neurons in Huntington's Disease, Experimental Neurology, 159: 362-376 (1999).
Skotte, N.H. et al., Allele-specific suppression of mutant huntingtin using antisense oligonucleotides: providing a therapeutic option for all Huntington disease patients, PLoS One, 9(9): e107434 1-18 (2014).
Small, L.D. et al.,Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Sonveaux, E., Protecting Groups in Oligonucleotide Synthesis, Protocols for Oligonucleotide Conjugates, Methods in Molecular Biology, Edited by AGRAWAL, S., Humana Press, 26: 1-71 (1994).
Spinelli, N. et al., Use of Allylic Protecting Groups for the Synthesis of Base-Sensitive Prooligonucleotides, European Journal of Organic Chemistry, 49-56 (2002).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaselenol-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-H-2,1-benzoxathiol-3-one 1-oxide—A New Reagent for Stereospecific Oxidation of Nucleoside H-Phosphonothioate Diesters, Tetrahedron Letters, 33(22): 3189-3192 (1992).
Stawinski, J. and Thelin, M., 3H-1,2-benzothiaselenol-3-one. A new selenizing reagent for nucleoside H-phosphonate and H-phosphonothioate diesters, Tetrahedron Letters, 33(47): 7255-7258 (1992).

(56) References Cited

OTHER PUBLICATIONS

Stec et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).

Stec et al., Oxathiaphospholane Method of Stereocontrolled Synthesis of Diribonucleoside 3', 5'-Phosphorothiptes, J. Org. Chem., 61(19): 6713-6716 (1996).

Stec et al., Stereocontrolled Synthesis of Oligo (nucleoside phosphorothioate)s, Angew. Chem. Int. Ed. Engl., 33:709-722 (1994).

Stec et al., Stereospecific Synthesis of P-Chiral Analogs of Oligonucleotides, Methods in Molecular Biology, 20: 285-313 (1993).

Stec, Oligo(nucleoside Phosphorothioate)s: The Quest of P-Chirality, in Phosphorus, Sulfur, and Silicon, 177(6): 1775-1778 (2002).

Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).

Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).

Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).

Stein, C.A. and Cheng, Y.C., Antisense oligonucleotides as therapeutic agents—is the bullet really magical?, Science, 261(5124):1004-12 (1993).

Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).

Suska, A. et al., Antisense oligonucleotides: Stereocontrolled synthesis of phosphorothioate oligonucleotides, Pure and Applied Chemistry, 65(4):707-714 (1993).

Takeno, H. et al., Selection of an RNA Molecule that Specifically Inhibits the Protease Activity of Subtilisin, J. Biochem., 125: 1115-1119 (1999).

Tamura et al., Preparation of Stereoregulated Antisense Oligodeoxyribonucleoside Phoshorothioate and Interaction with its Complementary DNA and RNA, Nucleosides & Nucleotides, 17(1-3): 269-282 (1998).

Tang, J. et al., Enzymatic Synthesis of Stereoregular (All Rp) Oligonucleotide Phosphorothioate and Its Properties, Nucleosides Nucleotides, 14(3-5):985-990 (1995).

Tawarada, R. et al., Mechanistic studies on oxidative condensation of a thymidine 3'-H-phosphonate derivative with 3'-O-acetylthymidine, Archive for Organic Chemistry, (3):264-273 (2009).

Thayer, J.R. et al., Separation of oligonucleotide phosphorothioate distereoisomers by pellicular anion-exchange chromatography, Journal of Chromatography A, 1218: 802-808 (2011).

Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).

Tosquellas, G. et al., First synthesis of alternating Sate-phosphotriester/phosphodiester prooligonucleotides on solid support, Bioorganic and Medicinal Chemistry Letters, 8(20): 2913-2918 (1998).

Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).

Tosquellas, G. et al., The pro-oligonucleotide approach: solid phase synthesis and preliminary evaluation of model pro-dodecathymidylates, Nucleic Acids Research, 26(9):2069-2074 (1998).

Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).

Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).

Tsai, C.H. et al., Enzymatic synthesis of DNA on glycerol nucleic acid templates without stable duplex formation between product and template, Proceedings of the National Academy of Science, 104(37):14598-14603 (2007).

Tuerk, C. and Gold, L., Systematic Evolution of Ligans by Exponential Enrichment: RNA Ligands to Bacteriophage T4 DNA Polymerase, Science, 249: 505-510 (1990).

Turner, D.H. et al, Improved Parameters for Prediction of RNA Structure, Cold Spring Harbor Symposia on Quantitative Biology, LII: 123-133 (1987).

Turner, D.H. et al., Free Energy Increments for Hydrogen Bonds in Nucleic Acid Base Pairs, J. Am. Chem. Soc., 109: 3783-3785 (1987).

Umemoto, T et al., Oligoribonucleotide Synthesis by the use of 1-(2-cyanoethoxy)ethyl (CEE) as a 2'-hydroxy protecting group, Tetrahedron Letters 45: 9529-9531 (2004).

Uphoff, K.W. et al., In vitro selection of aptamers: the death of pure reason, Curr. Opin. Struct. Biol., 6: 281-288 (1996).

Usman, N et al., Automated Chemical Synthesis of Long Oligoribonucleotides Using 2'-O-Siylylated Ribonucleoside 3'-O-Phosphoramidites on a Controlled-Pore Glass Support, J. Am. Chem. Soc. 109(25): 7845-7854 (1987).

Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthyl)ethyl]phosphoramidothioates, Journal of the American Chemical Society, 114(26):10197-10202 (1992).

Van Der Veken, P. et al., Irreversible inhibition of dipeptidyl peptidase 8 by dipeptide-derived diaryl phosphonates, Journal of Medicinal Chemistry, 50(23): 5568-5570 (2007).

Vasquez, K.M. et al., Chromosomal mutations induced by triplex-forming oligonucleotides in mammalian cells, Nucl. Acids Res. 27(4): 1176-1181 (1999).

Verma, S. and Eckstein, F., Modified Oligonucleotides: Synthesis and Strategy for Users, Annu. Rev. Biochem., 67: 99-134 (1998).

Vermeulen, A. et al., Double-Stranded Regions Are Essential Design Components Of Potent Inhibitors of RISC Function, RNA, 13: 723-730 (2007).

Vives, E. et al., Lipophilic pro-oligonucleotides are rapidly and efficiently internalized in HeLa cells, Nucleic Acids Research, 27(20):4071-4076 (1999).

Vlassov, V.V. et al., Transport of oligonucleotides across natural and model membranes, Biochimica et Biophysica Acta, 1197: 95-108 (1994).

Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Letters, 32(26):3005-3008 (1991).

Vuyisich, M. and Beal, P.A., Regulation of the RNA-dependent protein kinase by triple helix formation, Nuc, Acids Res., 28(12): 2369-74 (2000).

Wada et al., Stereocontrolled Synthesis of Phosphorothioate RNA by the Oxazaphospholidine Approach, Nucleic Acids Symp. Ser., 48: 57-58 (2004).

Wada, T. et al., Chemical synthesis and properties of stereoregulated phosphorothioate RNAs, Nucleic Acids Symposium Series, 51:119-120 (2007).

Wada, T. et al., Stereocontrolled synthesis of phosphorothioate DNA by an oxazaphospholidine approach, Nucleic Acids Research Supplement, 3:109-110 (2003).

Wagner, C.R. et al., Pronucleotides: toward the in vivo delivery of antiviral and anticancer nucleotides, Medicinal Research Reviews, 20(6):417-451 (2000).

(56) References Cited

OTHER PUBLICATIONS

Walker, J.R. et al., Structure of the Ku heterodimer bound to DNA and its implications for double-strand break repair, Nature, 412: 607-614 (2001).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. et al., Synthesis, biophysical properties and biological activity of second generation antisense oligonucleoties containing chiral phosphorothioate linkages, Nucleic Acid Research, 27 pages, online advance access (2014).
Wang H, et al., Therapeutic gene silencing delivered by a chemically modified siRNA against mutant SOD 1 slows ALS progression, The Journal of Biological Chemistry, 283(23):15845-15852 (2008).
Wang, J.-C. et al., A stereoselective synthesis of dinucleotide phosphorothioate triesters through a chiral indol-oxazaphosphorine intermediate, Tetrahedron Letters, 38(5):705-708 (1997).
Warby, S.C. et al., CAG expansion in the Huntington disease gene is associated with a specific and targetable predisposing haplogroup, Am. J. Hum. Genet., 84(3): 351-366 (2009).
Weidner, J.P. et al., Alkyl and Aryl Thiolsulfonates, Journal of Medicinal Chemistry, 7(5): 671-673 (1964).
Weiser, T.G., et al., An estimation of the global volume of surgery: a modeling strategy based on available data, Lancet, 372(9633): 139-144 (2008).
Welz et al., 5-(Benzylmercapto)-1H-tetrazole as activator for 2'-O-TBDMS phosphoramidite building blocks in RNA synthesis, Tetrahedron Letters, 43: 795-797 (2002).
Wengel, J., Synthesis of 3'-C- and 4'-C-Branched Oligodeoxynucleotides and the Development of Locked Nucleic Acid (LNA), Acc. Chem. Res., 32: 301-310 (1999).
Widdison, W. C. et al., Semisynthetic Maytansine analogues for the targeted treatment of cancer, Journal of Medicinal Chemistry, 49(14): 4392-4408 (2006).
Wild, E. et al., Quantification of mutant huntingtin protein in cerebrospinal fluid from Huntington's disease patients, The Journal of Clinical Investigation, 125(5): 1979-1986 (2015).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).
Wright, P. et al., Large scale synthesis of oligonucleotides via phosphoramidite nucleosides and a high-loaded polystyrene support, Tetrahedron Letters, 34(21):3373-3736 (1993).
Written Opinion for PCT/IB2009/007923, 8 pages (dated Sep. 6, 2010).
Written Opinion for PCT/IB2015/000395, 10 pages (dated Oct. 30, 2015).
Written Opinion for PCT/JP11/55018, 3 pages (dated Mar. 29, 2011).
Written Opinion for PCT/JP11/71559, 6 pages (dated Dec. 20, 2011).
Written Opinion for PCT/JP2010/065900, 5 pages (dated Sep. 15, 2010).
Written Opinion for PCT/JP2013/004303, 6 pages (dated Aug. 13, 2013).
Written Opinion for PCT/US2010/041068, 11 pages, (dated Sep. 1, 2010).
Written Opinion for PCT/US2011/064287, 14 pages (dated Apr. 12, 2012).
Written Opinion for PCT/US2012/046805, 9 pages (dated Sep. 19, 2012).
Written Opinion for PCT/US2013/050407, 12 pages (dated Jan. 9, 2014).
Xiang, Y. et al., Effects of RNase L mutations associated with prostate cancer on apoptosis induced by 2',5'-oligoadenylates, Cancer Research, 63(20):6795-6801 (2003).
Xiong, H.Y. et al., The human splicing code reveals new insights into the genetic determinants of disease, Science, 347(6218): 144 (2015).
Xu, D. and Esko, J.D., Demystifying Heparan Sulfate- Protein Interactions, Annu. Rev. Biochem., 83: 129-157 (2014).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Yamada, O. et al., Diastereoselective Synthesis of 3,4-Dimethoxy-7-morphinanone: A Potential Route to Morphine, Organic Letters, 2(18): 2785-2788 (2000).
Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).
Yanai, H. et al., Suppression of immune responses by nonimmunogenic oligodeoxynucleotides with high affinity for high-mobility group box proteins (HMGBs), PNAS Early Edition, 1-6 (2011).
Yu, S. et al., A One-Pot Formal [4 + 2] Cycloaddition Approach to Substituted Piperidines, Indolizidines, and Quinolizidines. Total Synthesis of Indolizidine (-)-2091, Journal of Organic Chemicals, 70:7364-7370 (2005).
Zhang, L. et al., A simple glycol nucleic acid, Journal of the American Chemical Society, 127(12):4174-4175 (2005).
Zhang, R.S. et al., Synthesis of two mirror image 4-helix junctions derived from glycerol nucleic acid, Journal of the American Chemical Society, 130(18):5846-5847 (2008).
Zhao, J. et al., Genome-wide Identification of Polycomb-Associated RNAs by RIP-seq, Molecular Cell, 40: 939-953 (2010).
Zlatev et al., Phosphoramidate dinucleosides as hepatitis C virus polymerase inhibitors, J Med Chem., 51(18): 5745-57 (2008).
Zon, Automated synthesis of phosphorus-sulfur analogs of nucleic acids-25 years on: potential therapeutic agents and proven utility in biotechnology, New J. Chem., 34(5): 795-804 (2010).
Zon, G and Stec, W.J., Phosphorothioate oligonucleotides, Oligonucleotides and Analogues: A Practical Approach, 87-108 (1991).
Arai, K. et al., Synthesis and properties of novel 2'-O-alkoxymethyl-modified nucleic acids, Bioorganic & Medicinal Chemistry Letters, 21(21): 6285-6287 (2011).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications, Biochemistry, 44: 9045-9057 (2005).
Kiviniemi, A. et al., Solid-Supported 2'-O-Glycoconjugation of Oligonucleotides by Azidation and Click Reactions, Bioconjugate Chemistry, 22(6): 1249-1255 (2011).
Pontiggia, R. et al., 2-C-Methyluridine modified hammerhead riboxyme against the estrogen receptor, Bioorganic & Medicinal Chemistry Letters, 20: 2806-2808 (2010).
Pontiggia, R. et al., DNAzymes and ribozymes carrying 2'-C-methyl nucleotides, Nucleic Acids Sumposium Series, 52: 521-522 (2008).
Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apsppp], Tetrahedron 51(10): 2991-3014 (1995).
Rozners, E. et al., Evaluation of 2'-hydroxyl protection in RNA-synthesis using the H-phosphonate approad, Nucleic Acids Research, 22(1): 94-99 (1994).

(56) References Cited

OTHER PUBLICATIONS

Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).
Saneyoshi, H. et al., A General Method for the Synthesis of 2'-O-Cyanoethylated Oligoribonucleotides Having Promising Hybridization Affinity for Dna and Rna and Enhanced Nuclease Resistance, The Journal of Organic Chemistry, 70(25): 10453-10460 (2005).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).
International Search Report for PCT/JP2011/077313, 2 pages (dated Jan. 10, 2012).
Aartsma-Rus, A. et al., Targeted exon skipping as a potential gene correction therapy for Duchenne muscular dystrophy, Neuromuscular Disorders, 12: S71-S77 (2002).
Ager, D.J. The Peterson olefination reaction, Organic Reactions, 38: 1-223 (2004).
Agrawal, S. and Kandimalla, E.R., Antisense and/or Immunostimulatory Oligonucleotide THerapeutics, Current Cander Drug Targets, Bentham Science, 1(3): 1 page. URL: <http.www.eurekaselect.com/65087/article> [Retrieved Apr. 3, 2016 ].
Block, S.S. and Weidner, J.P. Vibrational Behavior and Structure of Disulfide Dioxides (Thiolsulfonates), Applied spectroscopy, 20(2): 71-73 (1966).
Boczkowska, M. et al., Stereodefined Phosphorothioate Analogues of DNA: Relative Thermodynamics Stability of the Model PS-DNA/RNA complexes, Biochemistry, 41: 12483-12487 (2002).
Bonora, G.M. et al., Large Scale, liquid phase synthesis of oligonucleotides by the phosphoramidite approach, Nucleic Acids Research, 21(5): 1213-1217 (1993).
Brill, W. et al., Thioalkylation of Nucleoside-H-Phosphonates and Its Application to Solid Phase Synthesis of Oligonucleotides, Tetrahedron Letters, 36(5):703-706 (1995).
Bumcrot. D et al., RNAi therapeutics: a potential new class of pharmaceutical drugs, Nat. Chem. Biol., 2:711-9 (2006).
Campbell, J. et al., Hybrid polymer/MOF membranes for Organic Solvent Nanofiltration (OSN): Chemical modification and the quest for perfection, Journal of Membrane Science, 503: 166-176 (2015).
CAS Registry Number 1225524-67-3: STN Entry Date May 28, 2010: α-[(2-methylphenyl)methyl]-2-Pyrrolidinemethanol.
CAS Registry Number 1225524-68-4: STN Entry Date May 28, 2010: α-[(4-methylphenyl)methyl]-2-Pyrrolidinemethanol.
CAS Registry Number 1225525-00-5: STN Entry Date May 28, 2010: α-[(2,4,6-trimethylphenyl)methyl]-2-Pyrrolidinemethanol.
CAS Registry Number 1225564-20-0: STN Entry Date May 28, 2010: α-[(4-ethylphenyl)methyl]-2-Pyrrolidinemethanol.
CAS Registry Number 1225594-74-0: STN Entry Date May 28, 2010: α-[(2-chioro-6-fluorophenyl)methyl]-2-Pyrrolidinemethanol.
CAS Registry Number 1225682-42-7: STN Entry Date May 30, 2010: α-[(4-chiorophenyl)methyl]-2-Pyrrolidinemethanol.
CAS Registry Number 1226037-41-7: STN Entry Date May 30, 2010: α-[(3-chiorophenyl)methyl]-2-Pyrrolidinemethanol.
CAS Registry Number 1226118-97-3: STN Entry Date May 30, 2010: α-[(3-bromophenyl)methyl]-2-Pyrrolidinemethanol.
CAS Registry Number 1226119-02-3: STN Entry Date May 30, 2010: α-[(4-bromophenyl)methyl]-2-Pyrrolidinemethanol.
CAS Registry Number 1226146-65-1: STN Entry Date May 30, 2010: α-[(2,4-dimethylphenyl)methyl]-2-Pyrrolidinemethanol.
CAS Registry Number 1226160-20-8: STN Entry Date May 30, 2010: α-[(2,5-dimethylphenyl)methyl]-2-Pyrrolidinemethanol.
CAS Registry Number 1228178-36-4: STN Entry Date May 30, 2010: α-[(2-fluorophenyl)methyl]-2-Pyrrolidinemethanol.
CAS Registry Number 1226188-05-2: STN Entry Date May 30, 2010: α-[[4-(1-methylethyl)phenyl]methyl]-2-Pyrrolidinemethanol.

CAS Registry Number 1226204-20-1: STN Entry Date May 30, 2010: α-[(3-methylphenyl)methyl]-2-Pyrrolidinemethanol.
CAS Registry Number 1226231-44-2: STN Entry Date May 30, 2010: α-[(2-methylphenyl)methyl]-2-Pyrrolidinemethanol.
CAS Registry Number 1226352-28-8: STN Entry Date May 30, 2010: α-[(2,4-diclorophenyl)methyl]-2-Pyrrolidinemethanol.
CAS Registry Number 1226352-38-0: STN Entry Date May 30, 2010: α-[(3,4-diclorophenyl)methyl]-2-Pyrrolidinemethanol.
CAS Registry Number 1226413-27-9: STN Entry Date May 30, 2010: α-(phenylmethyl)-2-Pyrrolidinemethanol.
CAS Registry Number 1226419-15-3: STN Entry Date May 30, 2010: α-[(4-flurophenyl)methyl]-2-Pyrrolidinemethanol.
CAS Registry Number 1263282-82-1: STN Entry Date Feb. 21, 2011: (S)-[(diphenyl)methyl]-2-Pyrrolidinemethanol.
Chang., W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmci.2016.07.064.
Crooke, S.T. and Geary, R.S. Clinical pharmacological properties of mipomersen (Kynamno), a second generation antisense inhibitor of apolipoprotein B, Br. J. Clin. Pharmacol., 76: 269-276 (2012).
Crooke, S.T., Molecular mechanisms of action of antisense drugs, Biochemica et Biophysica Acta, 1489: 31-44 (1999).
De Koning, M.C. et al., Simple and Efficient Solution-Phase Synthesis of Oligonucleotides Using Extractive Work-Up, Organic Process Research & Development, 10: 1238-1245 (2006).
Deleavey, G.F. and Damha, M.J. Designing chemically modified oligonucleotides for targeted gene silencing, Chem. Biol., 19: 937-54 (2012).
Documents submitted to and/or received from the United States Securities and Exchange Commission: downloaded from EDGAR (Feb. 2, 2015 to Dec. 10, 2015).
Documents submitted to and/or recieved from the United States Securities and Exchange Commission: downloaded from EDGAR (Dec. 17, 2015 to Oct. 4, 2016).
Eckstein, F. et al., Stereochemistry of polymerization by DNA-dependent RNA-polymerase from *Escherichia coli*: an investigation with a diesteromeric ATP-analogue, Proc. Natl. Acad. Sci. USA, 73: 2987-90 (1976).
Gaffney, P.R.J. et al., Liquid-Phase Synthesis of 2'-Methyl-RNA on a Homostar Support through Organic-Solvent Nanofiltration, Chem. Eur. J., 21: 1-10 (2015).
Guerciolini, R., Allete-selective Silencing of Mutant Huntingtin by Stereopure Oligonucleotides, WAVE Life Sciences, Huntington's Disease Society of America, HDSA Presentation 2016 (Jun. 3, 2016).
Hammond. S.M. and Wood, M.J. Genetic therapies for RNA mis-splicing diseases, Trends Genet., 27: 196-205 (2011).
Hartmann, B. et al., Sequence effects on energetic and structural properties of phosphorothioate DNA: a molecular modelling study, Nucleic Acids Research, 27(16): 3342-3347 (1999).
Hartmann, G. et al., Delineation of a CpG Phosphorothioate Oligodeoxynucleotide for Activating Primate Immune Response in Vitro and in Vivo, The Journal of Immunology, 164(3): 1817-1624 (2000).
Heger, W. et al., Embryotoxic effects of thalidomide derivatives on the non-human primate Callithrix jacchus: 3 Teratogenic potency of the EM 12 enantiomers, Arch. Toxicol., 62: 205-208 (1988).
International Preliminary Report on Patentability for PCT/JP2013/069107, 10 pages (Jan. 15, 2015).
International Search Report of PCT/JP2013/069107, 2 pages (dated Oct. 1, 2013).
Iwamoto, N. et al., Optimization of Therapeutic Phosphorothioate Ollgonucleotides by P-Chirality Control, WAVE Life Sciences, PSJ Congress: The Pharmaceutical Society of Japan, (Mar. 25, 2015-Mar. 26, 2016).
Jahns, H., et al., Sterochemical bias introduced during RNA synthesis modulates the activity of phosphorothioate siRNAs, Nat. Commun., 6: 6317 (2015).
Karwowski, B. et al., Sterocontrolled Synthesis of LNA Dinucleoside Phosphorothioate by the Oxathiaphospholane Approach, Bioorganic & Medicinal Chemistry Letters, 11: 1001-1003 (2001).

(56) References Cited

OTHER PUBLICATIONS

Kim, D. et al., Immunostimulation and anti-DNA antibody production by backbone modified CpG-DNA, Biochemical and Biphysical Research Communicationes, 379: 362-367 (2009).
Kim, S. et al., Liquid-Phase RNA Synthesis by Using Alkyl-Chain-Soluble Support, Chem. Eur. J., 19: 8615-8620 (2013).
Koziolkiewicz, M., et al., Sterodifferentiation—the effect of P chirality of oligo(nucleoside phosphorothioates) on the activity of bacterial RNase H, Nucleic Acids Res., 23: 5000-5 (1995).
Krieg, A.M. et al., P-chirality-dependent immune activation by phosphorothioate CpG oligodeoxynucleotides, Oligonucleotides, 13(6): 491-499 (2003).
Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).
Kwon, H-J. et al., NF-kappaB-dependent regulation of tumor necrosis factor-alpha gene expression by CpG-oligodeoxynucleotides, Biochem. Biophys, Res. Commun., 311(1): 129•138 (2003).
Levin, A.A. et al., Basic Principles of the Pharmacokinetics of Antisense Oligonucleotide Drugs, Antisense Drug Technology: Principles, Strategies, and Applications, Second Edition, Chapter 7: 183-215 (2008).
Lima, W.F., et al., Human RNase H1 discriminates between subtle variation in the structure of the heteroduplex substrate, Mol. Pharmacol., 71: 83-91 (2007).
Linton, M.F., et al., Transgenic Mice Expressing High Plasma Concentrations of Human Apolipoproteins B100 and Lipoprotein (a), J. Clin. Invest., 92: 3029-37 (1993).
Matsuno, Y. et al., Synthetic Method for Oligonucleotide Block by Using Alkyl-Chain-Soluble Support, Org. Lett., 18: 800-803 (2016).
Meade, M.F., et al., Efficient delivery of RNAi prodrugs containing reversible change-neutralizing phosphotriester backbone modifications, Nat. Biotech., 32: 1256-61 (2014).
Meena, Control of Human RNase H Mediated Cleavage by Steropure Phosphorothioate Oligonucleotides, WAVE Life Sciences, TIDES Meeting (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Therapeutic Implications of Controlling P-Chirality in Phosphorothioate Oligonucleotides, TIDES Poster (May 12-15, 2014).
Meena, Optimization of Antisense Drugs by P-Sterochemistry Control, WAVE Life Sciences, OTS Annual Meeting 2014, Oligonucleotides Therapeutics Society (Oct. 12-14, 2014).
Molenkamp, B.G. et al., Local Administration of PF•3512676 CpG-B Instigates Tumor-Specific CD8+ T-Cell Reactivity in Melanoma Patients, Clin, Cancer Res., 14(14): 4532-4542 (2008).
Molina, A.G. et al., Acetylated and Methylated β-Cyciodextrins as Viable Soluble Supports for the Synthesis of Short 2'-Oligodeoxyribonucleotides in Solution, Molecules, 17: 12102-12120 (2012).
Molina, A.G. et al., Assembly of Short Oligoribonucleotides from Commercially Available Building Block on a Tetrapodal Soluble Support, Current Organic Synthesis, 12: 1-6 (2015).
Molina, A.G. et al., Solution Phase synthesis of short oligoribonucleotides on a precipitative tetrapodal support, Belistein Journal of Organic Chemistry, 10:2279-2285 (2014).
Molina, A.G., Synthesis of Short Oligonucleotides on a Soluble Support by the Phosphoramidte Method, University of Turku, 1-66 (2015).
Nielsen, J. and Caruthers, M.H., Directed Arbuzov-type reactions of 2-cyano-1,1-dimethylethyl deoxynucleoside phosphites, J. Am. Chem. Soc., 110: 6275-6 (1988).
Nukaga, Y., et al., Sterocontrolled Solid-Phase Synthesis of Phosphate/Phosphorothioate (PO/PS) Chimeric Oligodeoxyribonucleotides on an Automated Synthesizer Using an Oxazaphosphoadine-Phosphoramidite Method, J. Org. Chem., A-J, 10 pages (Publication Date (Web): Mar. 3, 2016).

Pèrez, B. et al., Antisense Mediated Splicing Modulation For Inherited Metabolic Diseases: Challenges for Delivery, Nucleic Acid Therapies, 24(1): 48-56 (2014).
Regan, J.F., et al., A Rapid Molecular Approach for Chromosonal Phasing, PLOS ONE, 1-15 (2015).
Schmitz, C. et al., Synthesis of P-Sterogenic Phosphoramidite and Phosphorodismadite Ligands and Their Application in Asymmetric Catalysis, Eur. J. Org. Chem., 6205-6230 (2015).
Sharma, V.K. et al. Antisense Oligonucleotides: modifications and clinical trials, Med. Chem. Commun., 5: 1454-71 (2014).
Sproat, B.S., RNA Synthesis Using 2'-O-(Tert•Butyldimethylsilyl) Protection, Methods in Molecular Biology, 288: 17-31 (2005).
Stec, W.J. and Zon. G., Stereochemical Studies of the Formation of Chiral Internucleotide Linkages by Phosphormadite COupling in the Synthesis of Oligodeocyribonucleotides, Tetrahedron Letters, 25(46): 5279-5282 (1984).
Stec, W.J. et al., Automated Solid-Phase Synthesis, Separation, and Sterochemistry of Phosphorothioate Analogues of Oligodeocyribonucleotides, J. Am. Chem. Soc., 106: 6077-6079 (1984).
Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).
Swayze, E.E. et al., Antisense oligonucleotides containing locked nucleic acid improve potency but cause significant hepatotoxicity in animals, Nucleic Acids Research, 35(20: 687-700 (2007).
Takahashi, D. et al., Novel diphenylmethyl-Derived Amide Protecting Group for Efficient Liquid-Phase Peptide Synthesis: AJIPHASE, Org. Lett. 14(17): 4514-4517 (2012).
Tam, Journal of Hematotherapy & Stem Cell Research, 12: 467-471 (2003).
U.S. Food and Drug Administration, Development of New Stereoisomeric Drugs, 8 pages (May 1, 1992) URL: http://fda.gov/Drugs/GuidanceComplianceRegulatoryInformation/Guidances/ucm122883.htm [Retrieved Jun. 15, 2016].
WaVe Life Sciences Poster, Therapeutic Implications of Controlling P-Chirality in Phosphorothioate Oligonucleotides, TIDES, San Diego (May 3-6, 2014).
WAVE Life Sciences Press Release, WAVE Life Sciences Added to the Russell 2000© Index, 2 pages (Jun. 27, 2016).
WAVE Life Sciences Press Release, WAVE Life Sciences Announces Plan to Deliver Six Clinical Programs by 2018, 6 pages (Jan. 29, 2016).
WAVE Life Sciences Press Release, WAVE Life Sciences Announces Pricing of Inital Public Offering, 3 pages (Nov. 11, 2015).
WAVE Life Sciences Press Release, WAVE Life Sciences Appoints Dr. Michael Panzara as Head of Neurology Franchise, 4 pages (Jul. 12, 2016).
WAVE Life Sciences Press Release, WAVE Life Sciences Appoints Keith Regnante as Chief Financial Officer, 4 pages (Aug. 17, 2016).
WAVE Life Sciences Press Release, WAVE Life Sciences Appoints Roberto Guerciolini, M. Senior Vice President and Head of Early Development, 2 pages (Apr. 7, 2015).
WAVE Life Sciences Press Release, WAVE Life Sciences Close $18 Million Series A Financing to Advance Steropure Nucleic Acid Therapeutics, 3 pages (Feb. 2, 2015).
WAVE Life Sciences Press Release, WAVE Life Sciences Enters Collaboration with Pfizer to Develop Genetically Targeted Therapies for the Treatment of Metabolic Diseases, 5 pages (May 5, 2016).
WAVE Life Sciences Press Release, WAVE Life Sciences Expands Steropure Synthetic Chemistry Platform Capabilities, Augments Patent Portfolio with Addition of Single-Stranded RNAi (ssRNAi), 3 pages (Jun. 8, 2015).
WAVE Life Sciences Press Release, WAVE Life Sciences Raises $66 Million in Series B Financing, 3 pages (Aug. 18, 2015).
WAVE Life Sciences Press Release, WAVE Life Sciences Receives Orphan Drug Designation from FDA for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).

(56) References Cited

OTHER PUBLICATIONS

WAVE Life Sciences Press Release, WAVE Life Sciences Reports Fourth Quarter and Full Year 2015 Financial Results and Provides Business Updates, 10 pages (Mar. 30, 2016).
WAVE Life Sciences Press Release, WAVE Life Sciences Reports Second Quarter 2016 Financial Results and Provides Business Update, 10 pages (Aug. 15, 2016).
WAVE Life Sciences Press Release, WAVE Life Sciences to Advance Next-Generation Nucleic Acid Terapies to Address Unmet Need in Duchenne Muscular Dystrophy, 6 pages (May 9, 2016).
WAVE Life Sciences Press Release, WAVE Life Sciences to Present at the Deutsche Bank 41st Annual Health Care Conference, 2 pages (Apr. 29, 2016).
WAVE Life Sciences Press Release, WAVE Life Sciences to Present at the Jefferies 2016 Healthcare Conference, 2 pages (Jun. 1, 2016).
WAVE Life Sciences Press Release, WAVE Life Sciences to Present at the JMP Securities Life Sciences Conference, 2 pages (Jun. 15, 2016).
WAVE Life Sciences Press Release, WAVE Life Sciences to Present at teh LEERINK Partner 5th Annual Global Healthcare Conference, 2 pages (Feb. 3, 2016).
WAVE Life Sciences Press Release, WAVE Life Sciences to Present at the Leerink Partners Rare Disease & Immuno-Oncology Roundtable, 2 pages (Sep. 14, 2016).
WAVE Life Sciences Press Release, WAVE Life Sciences to Present at the SunTrust Robinson Humphrey 2016 Orphan Drug Day Conference, 2 pages (Feb. 16, 2016).
Xiong, H. Y. et al., The human splicing code reveals new insigts into the genetic determinants of disease, Science, 347(6218): 144, 12548051-8 (2015).
Yamato, K. et al., Enhanced specificity of HPV16 E6E7 siRNA by RNA-DNA chimera modification, Cancer Gene Therapy, 18: 587-597 (2011).
Yu, D. et al., Single-Stranded RNAs Use RNAi to Potently and Allele-Selectively Inhibit Mutant Huntingtin Expresssion, Cell, 150: 895-908 (2012).
Yu, D. et al., Stero-Enriched Phosphorothioate Oligodeoxynucleotides: Synthesis, Biophysical and Biological Properties, Bioorganic & Medicinal Chemistry, 8: 275-284 (2000).
Yu, R.Z. et al., Cross-species comparison of in vivo PK/PD relationships for second-generation antisense oligonucleotides targeting apolipoprotein B-100, Biochem, Pharmacol., 77: 910-919 (2009).
Zhang, J. et al., Optimization of Exon Skipping Therapies for Duchenne Muscular Dystrophy, WAVE Life Sciences, PPMD: Parent Project Muscular Dystrophy Meeting, Orlando, FL (Jul. 25, 2016).
Cieslak, J. et al., P NMR Study of the Desulfurization of Oligonucleoside Phosphorothioates Effected by "Aged" Trichloroacetic Acid Solutions, J. Org. Chem., 70: 3303-3306 (2005).
Efimov, V.A. et al., Rapid synthesis of long-chain deoxyribooligonadeotides by the N-methylimidazolide phosphotriester method, Nucleic Acids Research, 11(23): 8369-8397 (1983).
Isis Pharmaceuticals, Inc. 2014 Annual Report, Improving Patients' Lives by Treating Disease Through Targeting RNA, 192 pp. (2014).
*Isis Pharmaceuticals, Inc. v. Santaris Pharma A/S Corp.*, Order Denying Defendants' Motion for Summary Judgment Without Prejudice, Case No. 11cv02214 BTM (KSC), United States District Court, S.D. California, 5 pages (Sep. 19, 2012).
Iwamoto, N. et al., Control of phosphorothioate stereochemistry substantially increases the efficacy of antisense oligonucleotides, Nature Biotechnology, Supplementary Text and Figures 1-9, 13 pages (2017).
Iwamoto, N. et al., Control of phosphorothioate stereochemistry substantially increases the efficacy of antisense oligonucleotides, Nature Biotechnology, with Supplemental Data, 19 pages (2017).
Koch, T., A New Dimension in LNA Therapeutics, Roche Innovation Center, Copenhagen, Denmark, Presentation, 39 pages (May 3, 2017).

Koizumi, M. et al., Triplex formation with 2'-O,4'-C-ethylene-bridged nucleic acids (ENA) having C3'-endo conformation at physiological pH, Nuc. Acids Res., 31(12): 3267-3273 (2003).
Lauritsen, A. et al., Methylphosphonate LNA: A Locked Nucleic Acid with a Methylphosphonate Linkage, Chem. Comm., 13: 253-256 (2003).
Lauritsen, A. et al., Oligodeoxynucleotides containing amide-linked LNA-type dinucleotides: synthesis and high-affinity nucleic acid hybridization, Bioo. Med. Chem. Lett., 5: 530-531 (2002).
Lopez, C. et al., Inhibition of AAC(6')-lb-Mediated Resistance to Amikacin in Acinetobacter baumannii by an Antisense Peptide-Conjugated 2',4'- Bridged Nucleic Acid-NC-DNA Hybrid Oligomer, Antimicrobial Agents and Chemotherapy, 59(9): 5798-5803 (2015).
Martinez-Montero, S. et al., Locked 2'-Deoxy-2',4'-Difluororibo Modified Nucleic Acids: Thermal Stability, Structural Studies, and siRNA Activity, ACS Chem. Biol., 10: 2016-2023 (2015).
Nielsen, P.E. et al., Synthesis of 29-0,39-C-linked bicyclic nucleosides and bicyclic Oligonucleotides, J. Chem. Soc. Perkins Trans., 1: 3423-3433 (1997).
Obika, S. et al., Synthesis of 2'-0,4'-C-Methyleneuridine and -cytidine. Novel Bicyclic Nucleosides Having a Fixed C a ,-endo Sugar Puckering, Tetrahedron Lett., 38(50): 8735-8 (1997).
Pallan, P.S. et al., Structure and nuclease resistance of 20,40-constrained 20-O-methoxyethyl (cMOE) and 20-O-ethyl (cEt) modified DNAs, Chem. Comm., 48: 8195-8197 (2012).
Prakash, T.P. et al., Lipid Nanoparticles Improve Activity of Single-Stranded siRNA and Gapmer Antisense Oligonucleotides in Animals, ACS Chem. Biol., 5 pages (2013).
Rossetti, G., Structural aspects of the Huntingtin protein investigated by biocomputing methods, Thesis, RWTH Aachen University, Forschungszentrum Juelich, 173 page (2011).
Written Opinion for PCT/JP2015/050718 and English Translation, 6 pages (dated Apr. 21, 2015).
Aaronson, J.G. et al., Rapid HATU-Mediated Solution Phase siRNA Conjugation, Bioconjugate. Chem., 22: 1723-1728 (2011).
Aartsma-Rus, A. et al., Antisense-Induced Multiexon Skipping for Duchenne Muscular Dystrophy Makes More Sense, Am. J. Hum. Genet., 74:83-92 (2004).
Aartsma-Rus, A. et al., Therapeutic antisense-induced exon skipping in cultured muscle cells from six different DMD patients, Human Molecular Genetics, 12(8):907-914 (2003).
ALS Association, The ALS Association and the Packard Center Partner to Develop Animal Model Systems for Most Common Cause of Familial ALS, 4 pages (Mar. 1, 2012). URL: http://www.alsa.org/news/archive/new-animal-model-systems.html [Retrieved Dec. 14, 2017].
Anthony, K. et al., Exon Skipping Quantification by Quantitative Reverse-Transcription Polymerase Chain Reaction in Duchenne Muscular Dystrophy Patients Treated with the Antisense Oligomer Eteplirsen, Human Gene Therapy Methods, 23: 336-345 (2012).
Bartz, H. et al., Poly-guanosine strings improve cellular uptake and stimulatory activity of phosphodiester CpG oligonucleotides in human leukocytes, Vaccine, 23: 148-155 (2004).
Birts, C.N. et a., Transcription of Click-Linked Dna un Human Cells, Angew. Chem. Int. Ed., 53:2362-2365 (2014).
Blade, H. et al., Modular Synthesis of Constrained Ethyl (cEt) Purine and Pyrimidine Nucleosides, J. Org. Chem., 80: 5337-5343 (2015).
Burgers, P. M. J. et al., Stereochemistry of Hydrolysis by Snake Venom Phosphodiesterase, J. Biol. Chem., 254(16): 7476-7478 (1979).
Burgers, P.M.J. And Eckstein, F., A Study of the Mechanism of DNA Polymerase I from *Escherichia coli* with Diastereomeric Phosphorothioate Analogs of Deoxyadenosine Triphosphate, J. Biol. Chem., 254(15): 6889-6893 (1979).
Burgers, P.M.J. and Eckstein, F., Diastereomers of 5'-O-adenosyl 3'-O-uridyl phosphorothioate: chemical synthesis and enzymatic properties, Biochemistry, 18: 592-596 (1979).
Cankurtaran, E.S. et al., Clinical Experience with Risperidone and Memantine in the Treatment of Huntington's Disease, Journal of the National Medical Association, 98(8): 1353-1355 (2006).

(56) References Cited

OTHER PUBLICATIONS

Chak, L-L, and Okamura, K., Argonaute-dependent small RNAs derived from single-stranded, non-structured precursors, Frontiers in Genetics, 5(172): 1-15 (2014).
Chan, J.H.P. et al., Antisense Oligonucleotides: From Design to Therapeutic Application, Clinical and Experimental Pharmacology and Physiology, 33: 544-540 (2006).
Chappell, C. et al., Involvement of human polynucleotide kinase in double-strand break repair by non-homologous end joining, The EMBO Journal, 21(11): 2827-2832 (2002).
Cheloufi, S. et al., a Dicer-independent miRNA biogenesis pathway that requires Ago catalysis, Nature, 465(7298): 584-589 (2010).
Chen, B. and Bartlett, M., A One-Step Solid Phase Extraction Method for Bioanalysis of a Phosphorothioate Oligonucleotide and Its 3' n-1 Metabolite from Rat Plasma by uHPLC-MS/MS, The AAPS Journal, 14(4): 772-780 (2012).
Chmielewski, M.K. and Markiewicz, W.T., Novel Method of Synthesis of 5"-Phosphate 2'-O-ribosyl-ribonucleosides and Their 3'-Phosphoramidites, Molecules, 18:14780-14796 (2013).
Cieslak, J. et al., 31P NMR Study of the Desulfurization of Oligonucleoside Phosphorothioates Effected by "Aged" Trichloroacetic Acid Solutions, J. Org. Chem., 70: 3303-3306 (2005).
Crooke, S.T., Antisense Strategies, Current Molecular Medicine, 4: 465-487 (2004).
Crooke, S.T., Progress in Antisense Technology, Annu. Rev. Med., 55: 61-95 (2004).
Dejesus-Hernandez, M. et al., Expanded GGGGCC hexanucleotide repeat in non-coding region of C9ORF72 causes chromosome 9p-linked frontotemporal dementia and amyotrophic lateral sclerosis, Neuron, 72(2): 245-256 (2011).
Dias, N. and Stein, C.A., Antisense Oligonucleotides: Basic Concepts and Mechanisms, Molecular Cancer Therapeutics, 1: 347-355 (2002).
Dikfidan, A. et al., RNA Specificity and Regulation of Catalysis in the Eukaryotic Polynucleotide Kinase Clp1, Molecular Cell, 54: 975-986 (2014).
Documents submitted to and/or received from the United States Securities and Exchange Commission; downloaded from EDGAR (Nov. 9, 2016 to May 10, 2017).
Donnelly, C.J. et al., M1415. Development of C9orf72 ALS Biomarkers and Therapeutics, Annals of Neurology, 72 (suppl 16): S67-S68 (2012).
Donnelly, C.J. et al., RNA Toxicity from the ALS/FTD C90RF72 Expansion Is Mitigated by antisense Intervention, Neuron, 80:415-428 (2013).
Efimov, V.A. et al., Rapid synthesis of long-chain deoxyribooligonucleotides by the N-methylimidazolide phosphotriester method, Nucleic Acids Research, 11(23): 8369-8387 (1983).
Egholm, M. et al., PNA hybridizes to complementary oligonucleotides obeying the Watson-Crick hydrogen-bonding rules, Nature, 365, 566-568 (1993).
El-Sagheer, A.H. and Brown, T., Efficient RNA synthesis by in vitro transcription of a triazole-modified DNA template, Chem. Commun., 47(44):12057-12058 (2011).
El-Sagheer, A.H. and Brown, T., New strategy for the synthesis of chemically modified RNA constructs exemplified by hairpin and hammerhead ribozymes, PNAS, 107(35):15329-15334 (2010).
El-Sagheer, A.H. et al., Biocompatible artificial DNA linker that is read through by DNA polymerases and is functional in *Escherichia coli*, PNAS, 108(28):11338-11343 (2011).
Erler, W. et al., Patient Advisory Board Meeting, WAVE Life Sciences, London, 46 pages (Mar. 2, 2017).
Erler, W., Stereopure Exon 51-Skipping Oligonucleotide as a Potential Disease-Modifying Therapy for Duchenne Muscular Dystrophy, WAVE Life Sciences, 10 pages (2017).
Ewles, M. et al, Quantification of oligonucleotides by LC-MS/MS: the challenges of quantifying a phosphorothioate oligonucleotide and multiple metabolites, Bioanalysis, 6(4), 447-464 (2014).
Exiqon, Locked Nucleic Acid (LNA), Custom Oligonucleotides for RNA and DNA Research, 16 pages (Aug. 2009).

Fearon, K. et al., Phosphorothioate oligodeoxynucleotides: large-scale synthesis and analysis, impurity characterization, and the effect of phosphorus stereochemistry, Oligonucleotides as Therapeutic Agents, Ciba Found. Symp. 209: 19-31 (1997).
Freschauf, G., Identification of Small Molecule Inhibitors of the Human DNA Repair Enzyme Polynucleotide Kinase/Phosphatase, Master of Science in Experimental Oncology Thesis, University of Alberta, 155 pages (2011).
Gallier, F. et al., 5',6'-Nucleoside Phosphonate Analogues Architecture: Synthesis and Comparative Evaluation towards Metabolic Enzymes, Chem Med Chem, 6: 1094-1106 (2011).
Giacometti, R.D. et al., Design, synthesis, and duplex-stabilizing properties of conformationally constrained tricyclic analogues of LNA, Org. Biomol. Chem., 14: 2034-2040 (2016).
Gould, W.A. et al., Pyrrolidines. IX. 3-Aryl-3-pyrrolidinols, Journal of Medicinal Chemistry, 7(1): 60-67 (1964).
Gryaznov, S. and, Chen, J.-K., Oligodeoxyribonucleotide N3'4P5' Phosphoramidates: Synthesis and Hybridization Properties, J. Am. Chem. Soc., 116: 3143-3144 (1994).
Hagedorn, P.H. et al., Locked nucleic acid: modality, diversity, and drug discovery, Drug Discovery, 1-14 (Oct. 2017).
Haringsma, H.J. et al., mRNA knockdown by single strand RNA is improved by chemical modifications, Nucleic Acids Research, 40(9): 4125-4136 (2012).
Heemskerk, H.A. et al., In vivo comparison of 2'-O-methyl phosphorothioate and morpholino antisense oligonucleotides for Duchenne muscular dystrophy exon skipping, The Journal of Gene Medicine, 11:257-266 (2009).
Hendrix, C. et al., 1',5'-Anhydrohexitol Oligonucleotides: Synthesis, Base Pairing and Recognition by Regular Oligodeoxyribonucleotides and Oligoribonucleotides, Chem. Eur. J., 3(1): 110-120 (1997).
Hirama, T. et al., PCR-Based Rapid Identification System Using Bridged Nucleic Acids for Detection of Clarithromycin-Resistant Mycobacterium avium-M. intracellulare Complex Isolates, Journal of Clinical Microbiology, 54(3): 699-704 (2016).
Hirose, M. et al., MDM4 expression as an indicator of TP53 reactivation by combined targeting of MDM2 and MDM4 in cancer cells without TP53 mutation, Oncoscience, 1(12): (2014).
Hu, J. et al., Allele-Selective Inhibition of Huntingtin Expression by Switching to an miRNA-like RNAi Mechanism, Chemistry & Biology 17: 1183-1188 (2010).
Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).
Hu, J. et al., Recognition of c9orf72 Mutant RNA by Single-Stranded Silencing RNAs, Nucleic Acid Therapeutics, 8 (2016). Supplementary Figure, 1 page.
Hyrup., B. and Nielsen, P.E., Peptide Nucleic Acids (PNA): Synthesis, Properties and Potential Applications, Bioorg. Med. Chem., 4(1): 5-23 (1996).
International Search Report for PCT/JP2015/050714, and English Translation, 8 pages (dated Apr. 21, 2015).
International Search Report for PCT/JP2015/050716 and English Translation, 8 pages (dated Apr. 21, 2015).
International Search Report for PCT/JP2015/050718 and English Translation, 8 pages (dated Apr. 21, 2015).
International Search Report for PCT/US2016/043542, 6 pages (dated Dec. 28, 2016).
International Search Report for PCT/US2016/043598, 4 pages (dated Nov. 28, 2016).
International Search Report for PCT/US2016/056123, 5 pages (dated Mar. 17, 2017).
International Search Report for PCT/US2017/022135, 3 pages (dated Jun. 6, 2017).
International Search Report for PCT/US2017/030753, 6 pages (dated Sep. 26, 2017).
International Search Report for PCT/US2017/030777, 5 pages (dated Oct. 2, 2017).
International Search Report for PCT/US2017/035837, 4 pages (dated Aug. 24, 2017).
International Search Report for PCT/US2017/043431, ISA/US, 5 pages (dated Dec. 21, 2017).

(56) References Cited

OTHER PUBLICATIONS

International Search Report for PCT/US2017/045218, 3 pages (dated Sep. 27, 2017).
International Search Report for PCT/US2017/055601, ISR/US, 6 pages (dated Feb. 15, 2018).
International Search Report for PCT/US2017/062996, 4 pages (dated Mar. 9, 2018).
Ionis Pharmaceuticals, Inc., Ionis Pharmaceuticals Licenses IONIS-HTT Rx to Partner Following Successful Phase 1/2a Study in Patients with Huntington's Disease, Press Release, 2 pages (Dec. 11, 2017).
Isis Pharmaceuticals, Inc. 2014 Annual Report, Improving Patients' Lives by Treating Disease Through Targeting RNA, 192 pages (2014).
*Isis Pharmaceuticals, Inc.* v. *Santaris Pharma A/S Corp.*, Order Denying Defendants' Motion for Summary Judgment Without Prejudice, Case No. 11cv02214 BTM (KSC), United States District Court, S.D. California, 5 pages (dated Sep. 19, 2012).
Iwamoto, N. et al., Control of phosphorothioate stereochemistry substantially increases the efficacy of antisense oligonucleotides, Nature Biotechnology, Life Sciences Reporting Summary, 6 pages (2017).
Iwamoto, N. et al., Control of phosphorothioate stereochemistry substantially increases the efficacy of antisense oligonucleotides, Nature Biotechnology, pages 1-9 (2017).
Iwamoto, N. et al., Control of phosphorothioate stereochemistry substantially increases the efficacy of antisense oligonucleotides, Nature Biotechnology, Supplementary Methods, Supplementary Tables 1-4, and Supplementary Note, 23 pages (2017).
Iwamoto, N. et al., Control of phosphorothioate stereochemistry substantially increases the efficacy of antisense oligonucleotides, Nature Biotechnology, Supplementary Text and Figures 1-9, 13 pp. (2017).
Iwamoto, N. et al., Control of phosphorothioate stereochemistry substantially increases the efficacy of antisense oligonucleotides, Nature Biotechnology, with Supplemental Data, 19 pp. (2017).
Jepsen, J.S. et al., Lna-Antisense Rivals Sirna for Gene Silencing, Current Opinion in Drug Discovery and Development, 7(2): 188-194 (2004).
Jepsen, J.S. et al., Locked Nucleic Acid: a Potent Nucleic Acid Analog in Therapeutics and Biotechnology, Oligonucleotides,14: 130-146 (2004).
Jones, R.J. et al., Synthesis and binding properties of pyrimidine oligodeoxynucleoside analogs containing neutral phosphodiester replacements: the Formacetal and 3'-Thioformacetal Internucleoside Linkages, J. Org. Chem., 58: 2983-2991 (1993).
Kashida, H. et al., Acyclic artificial nucleic acids with phosphodiester bonds exhibit unique functions, Polymer Journal, 1-6 (2016).
Kaur, H. et al., Activation of natural killer-like Yt-Indy cells by oligodeoxynucleotides and binding by homologous pattern recognition proteins, Scandinavian Journal of Immunology, 62: 361-370 (2005).
Kay, C. et al., Huntingtin Haplotypes Provide Prioritized Target Panels for Allele-specific Silencing in Huntington Disease Patients of European Ancestry, the American Society of Gene & Cell Therapy, 1-13 (2015).
Kay, C. et al., Personalized gene silencing therapeutics for Huntington disease, Clinical Genetics, 1-8 (2014).
Kim, M., Beta conformation of polyglutamine track revealed by a crystal structure of Huntingtin N-terminal region with insertion of three histidine residues, Prion, 7(3): 221-228 (2013).
Kim, S-K. et al., Bridged Nucleic Acids (BNAs) as Molecular Tools, J Biochem Mol Biol Res., 1(3): 67-71 (2015).
Koch, T., a New Dimension in Lna Therapeutics, Roche Innovation Center, Copenhagen, Denmark, Presentation, 39 pp. (May 3, 2017).
Koizumi, M. et al., Triplex formation with 2'-0,4'-C-ethylene-bridged nucleic acids (Ena) having C3'-endo conformation at physiological pH, Nuc. Acids Res., 31(12): 3267-3273 (2003).
Koseoglu, M. et al., Effects of hemolysis interference on routine biochemistry parameters. Biochemia Medica., 21(1): 79-85 (2011). Retrieved May 18, 2017, Url: <http://www.biochemia-medica.com/2011/21/79>.
Koshkin, a.A. et al., Lna (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).
Kremer, B. et al., a Worldwide Study of the Huntington's Disease Mutation, the New England Journal of Medicine, 330(20): 1401-1406 (1994).
Kretschmer-Kazemi Far, R. And Sczakiel, G., the activity of siRNA in mammalian cells is related to structural target accessibility: a comparison with antisense oligonucleotides, Nucleic Acids Research, 31(15):4417-4424 (2003).
Krieg, a.M., Development of TLR9 agonists for cancer therapy, the Journal of Clinical Investigation, 117(5): 1184-1194 (2007).
Krieg, a.M., Therapeutic potential of Toll-like receptor 9 activation, Nature Reviews, 471-484 (2006).
Krishna, H. et al., Alkynyl Phosphonate Dna: a Versatile "Click-"able Backbone for Dna-Based Biological Applications, J. Am. Chem. Soc., 134: 11618?11631 (2012).
Krotz, a.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).
Kumar, R. et al., The First Analogues of LNA (Locked Nucleic Acids): Phosphorothioate-LNA and 2'-THIO-LNA, Bioo. Med. Chem. Let., 8: 2219-2222 (1998).
Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).
Lahiri, N., Shooting the messenger with single-stranded RNA gene silencing, edited by Wild, E., HDBuzz, 7 pages (Sep. 24, 2012). Retrieved Oct. 7, 2015. URL: http://en.hdbuzz.net/099.
Lauritsen, A. et al., Methylphosphonate LNA: A Locked Nucleic Acid with a Methylphosphonate Linkage, Bioo. Med. Chem. Lett., 13: 253-256 (2003).
Lauritsen, A. et al., Oligodeoxynucleotides containing amide-linked LNA-type dinucleotides: synthesis and high-affinity nucleic acid hybridization, Chem. Comm., 5: 530-531 (2002).
Lee, K-W et al., CG sequence- and phosphorothioate backbone modification-dependent activation of the NF-$_K$B-responsive gene expression by CpG-oligodeoxynucleotides in human RPMI 8226 B cells, Molecular Immonulogy, 41: 955-964 (2004).
Lee, K.-W. et al., CG sequence- and phosphorothioate backbone modification-dependent activation of the NF-$_K$B-responsive gene expression by CpG-oligodeoxynucleotides in human RPMI 8226 B cells, Molecular Immunology, 41: 955-964 (2004).
Leviten, M., Wave's Purity Progress, Biocentury, 1-6 (Sep. 28, 2017).
Li, M. et al., Synthesis and cellular activity of stereochemically-pure 2'-O-(2-methoxyethyl)-phosphorothioate oligonucleotides, Chem. Commun., 53: 541-544 (2017).
Liu, J. et al., Modulation of Splicing by Single-Stranded Silencing RNAs, Nucleic Acid Therapeutics, 25(3): 113-120 (2015).
Liu, S. et al., Evaluation of protective effect of multi-epitope DNA vaccine encoding six antigen segments of Toxoplasma gondii in mice Parasitol Res, 105:267-274 (2009).
Lopez, C. et al., Inhibition of AAC(6')-Ib-Mediated Resistance to Amikacin in Acinetobacter baumannii by an Antisense Peptide-Conjugated 2',4'-Bridged Nucleic Acid-NC-DNA Hybrid Oligomer, Antimicrobial Agents and Chemotherapy, 59(9): 5798-5803 (2015).
Madsen, A., Antisense Against C90RF72, MDA/ALS News Magazine, 2 pages (Jul. 1, 2012). URL: http://alsn.mda.org/article/antisense-against-c90rf72 [Retrieved Dec. 14, 2017].
Martinez, J. et al., Single-Stranded Antisense siRNAs Guide Target RNA Cleavage in RNAi, Cell, 110: 563-574 (2002).
Martinez-Montero, S. et al., Locked 2'-Deoxy-2',4'm-Difluororibo Modified Nucleic Acids: Thermal Stability, Structural Studies, and siRNA Activity, ACS Chem. Biol., 10: 2016-2023 (2015).

(56) References Cited

OTHER PUBLICATIONS

Matranga, C. et al., Passenger-Strand Cleavage Facilitates Assembly of siRNA into Ago2-Containing RNAi Enzyme Complexes, Cell, 123: 607-620 (2005). Supplemental Data, 6 pages.

Matsui, M. et al., Argonaute 2-dependent Regulation of Gene Expression by Single-stranded miRNA Mimics, Molecular Therapy, 10 pages (2016).

Matsui, M. et al., Transcriptional Silencing by Single-Stranded RNAs Targeting a Noncoding RNA That Overlaps a Gene Promoter, ACS Chem. Biol., 8: 122-126 (2013).

Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page (2016).

Mesmaeker, A.D. et al. Amides as a New Type of Backbone Modification in Oligonucleotides, Angew. Chem., Int. Ed. Engl., 33: 226-229 (1994).

Midturi, J. et al., Spectrum of Pulmonary Toxicity Associated with the Use of Interferon Therapy for Hepatitis C: Case Report and Review of the Literature, Clinical Infectious Diseases, 39(11): 1724-1729 (2004).

Monteys, A.M. et al., Artificial miRNAs Targeting Mutant Huntingtin Show Preferential Silencing In Vitro and In Vivo, Molecular THerapy—Nucleic Acids, 4: e234 1-11 (2015).

Morita, K. et al., 2'-O,4'-C-Ethylene-bridged nucleic acids (ENA) with nuclease-resistance and high affnity for RNA, Nucl. Acids Res., Supp. 1: 241-242 (2001).

Morita, K. et al., 20-O,40-C-Ethylene-Bridged Nucleic Acids (ENA): Highly Nuclease-Resistant and Thermodynamically Stable Oligonucleotides for Antisense Drug, Bioo. Med. Chem. Lett., 12: 73-76 (2002).

Morita, K. et al., Synthesis and properties of 2'-O,4'-C-Ethylene-bridged nucleic acids (ENA) as effective antisense oligonucleotides, Bioorganic & Medicinal Chemistry, 11(10): 2211-2226 (2003).

Nencka, R. et al., Novel Conformationally Locked Nucleosides and Nucleotides, Collection Symposoim Series, 14: 119-122 (2014).

Nielsen, P.E. and Haaima, G., Peptide nucleic acid (PNA). A DNA mimic with a pseudopeptide backbone, Chem. Soc. Rev., 73-78 (1997).

Nielsen, P.E. et al., Sequence-Selective Recognition of DNA by Strand Displacement with a Thymine-Substituted Polyamide, Science, 254(5037): 1497-1500 (1991).

Nielsen, P.E. et al., Synthesis of 29-O,39-C-linked bicyclic nucleosides and bicyclic Oligonucleotides, J. Chem. Soc. Perkins Trans., 1: 3423-3433 (1997).

Nishina, K. et al., DNA/RNA heteroduplex oligonucleotide for highly efficient gene silencing, Nature Communications, 6:7969, pages 1-13 (2015).

Obika et al. Stability and structural features of the duplexes containing nucleoside analogues with a fixed N-type conformation, 2'-O,4'-C-methyleneribonucleosides, Tetrahedron Lett. 39: 5401-5404 (1998).

Obika, S. et al., Synthesis of 2'-O,4'-C-Methyleneuridine and -cytidine. Novel Bicyclic Nucleosides Having a Fixed C a ,-endo Sugar Puckering, Tetrahedron Lett., 38(50): 8735-8 (1997).

Onizuka, K. et al., Short Interfering RNA Guide Strand Modifiers from Computational Screening, J. Am. Chem. Soc., 135: 17069-17077 (2013).

Osawa, T. et al., Synthesis and Properties of the 5-Methyluridine Derivative of 3,4-Dihydro-2H-pyran-Bridged Nucleic Acid (DpNA), J. Org. Chem., 80: 10474-10481 (2015).

Ostergaard, M.E. et al., Efficient Synthesis and Biological Evaluation of 5?-GalNAc Conjugated Antisense Oligonucleotides, Bioconjugate. Chem., 26: 1452-1455 (2015).

Pallan, P.S. et al., Structure and nuclease resistance of 20,40-constrained 20-O-methoxyethyl (cM0E) and 20-O-ethyl (cEt) modified DNAs, Chem. Comm., 48: 8195-8197 (2012).

Panzara, M. et al., Duchenne Muscular Dystrophy Advisory Board Meeting, WAVE Life Sciences, 70 pages (Mar. 3, 2017).

Parmer, R. et al., 5'-(E)-Vinylphosphonate: A Stable Phosphate Mimic Can Improve the RNAi Activity of siRNA-GalNAc Conjugates, Chem. Bio. Chem., 17: 1-6 (2016).

Pedersen, L. et al, A Kinetic Model Explains Why Shorter and Less Affine Enzyme-recruiting Oligonucleotides Can Be More Potent, Mol Ther Nucleic Acids, 3: e149 1-8 (2014).

Pendergraff, H.M. et al., Single-Stranded Silencing RNAs: Hit Rate and Chemical Modification, Nucleic Acid Therapeutics, 1-7 (2016).

Petersen, M. and Wengel, J., LNA: a versatile tool for therapeutics and genomics, TRENDS in Biotechnology, 21(2): 74-81 (2003).

Pontarollo, R.A. et al., Monocytes are required for optimum in vitro stimulation of bovine peripheral blood mononuclear cells by non-methylated CpG motifs, Veterinary Immunology and Immunopathology, 84(1-2): 43-59 (2002).

Prakash, T.P. et al., Identification of metabolically stable 5-phosphate analogs that support single-stranded siRNA activity, Nucleic Acids Research, 43(6): 2993-3011 (2015). Supplementary Data, 80 pages.

Prakash, T.P. et al., Lipid Nanoparticles Improve Activity of Single-Stranded siRNA and Gapmer Antisense Oligonucleotides in Animals, ACS Chem. Biol., 5 pp. (2013), DOI: 10.1021/cb4001316.

Prakash, T.P. et al., Synergistic effect of phosphorothioate, 50-vinylphosphonate and GalNAc modifications for enhancing activity of synthetic siRNA, Bioorg. Med. Chem. Lett., 26: 2817-2820 (2016).

Prakash, T.P. et al., Targeted delivery of antisense oligonucleotides to hepatocytes using triantennary N-acetyl galactosamine improves potency 10-fold in mice, Nucleic Acids Res., 42(13): 8796-807 (2014).

Pubchem, Substance Record for SID 174316404, Available Date: Mar. 31, 2014 (retrieved on Feb. 26, 2018). Retrieved from the Internet: <URL: https://pubchem.ncbi.nlm.nih.gov/substance/174316404>.

Pubchem, Substance Record for SID 174316700, Available Date: Mar. 31, 2014 (retrieved on Feb. 26, 2018). Retrieved from the Internet: <URL: https://pubchem.ncbi.nlm.nih.gov/substance/174316700>.

Pubchem, Substance Record for SID 174316999, Available Date: Mar. 31, 2014 {retrieved on Feb. 26, 2018). Retrieved from the Internet: <URL: https://pubchem.ncbi.nlm.nih.gov/substance/174316999>.

Rajwanshi, V.K. et al., LNA stereoisomers: xylo-LNA (b-d-xylo configured locked nucleic acid) and a-l-LNA (a-l-ribo configured locked nucleic acid), Chem. Commun., 1395-1396 (1999).

Ravn, J. et al., Stereodefined LNA Phosphorthioate Oligonucleotides, Roche Pharma Research and Early Development, RTR Research, Roche Innovation Center Copenhagen, RNA & Oligonucleotide Therapeutics Meeting, Poster, 1 page (Mar. 29-Apr. 1, 2017).

Renton, A.E. et al., A Hexanucleotide Repeat Expansion in C9ORF72 Is the Cause of Chromosome 9p21-Linked ALS-FTD, Neuron 72, 257-268 (Oct. 20, 2011).

Rossetti, G., Structural aspects of the Huntingtin protein investigated by biocomputing methods, Thesis, RWTH Aachen University, Forschungszentrum Juelich, 173 pages (2011).

Saetrom, P., Predicting the efficacy of short oligonucleotides in antisense and RNAi experiments with boosted genetic programming, Bioinformatics, 20(17): 3055-3063 (2004).

Sanhueza, C.A. et al., Efficient Liver Targeting by Polyvalent Display of a Compact Ligand for the Asialoglycoprotein Receptor, J. Am. Chem. Soc., 9 pages (2016).

Schirle, N. T. and Macrae, I.J., The Crystal Structure of Human Argonaute2, Science, 336(6084): 1037-1040 (2012).

Schirle, N.T. et al., Structural analysis of human Argonaute-2 bound to a modified siRNA guide, J. Am. Chem. Soc., 1-6 (2016).

Schirle, N.T. et al., Structural Basis for microRNA Targeting, Science, 346(6209): 608-613 (2014).

Schirle, N.T. et al., Water-mediated recognition of t1-adenosine anchors Argonaute2 to microRNA targets, eLife, 4: e07646 1-16 (2015).

Schultz, R.G. and Gryaznov, S.M., Oligo-24-fluoro-24-deoxynucleotide N34_P54 phosphoramidates: synthesis and properties, Nucleic Acids Res., 24(15): 2966-2973 (1996).

(56) References Cited

OTHER PUBLICATIONS

Scrimgeour, E.M. Huntington Disease (Chorea) in the Middle East, SQU. Med. J., 9(1): 16-23 (2009).
Seth, P., and Olson, R., Nucleic Acid Therapeutics—Making Sense of Antisesnse, 2016 Drug Design and Delivery Symposium, ACS Webinar, 1-36 (Jul. 26, 2016).
Seth, P.P. et al., Configuration of the 50-Methyl Group Modulates the Biophysical and Biological Properties of Locked Nucleic Acid (LNA) Oligonucleotides, J. Med. Chem., 53: 8309-8318 (2010).
Seth, P.P. et al., Design, Synthesis and Evaluation of Constrained Methoxyethyl, (cMOE) and Constrained Ethyl (cEt) Nucleoside Analogs, Nucleic Acids Symposium Series, 52(1), 553-554 (2008).
Seth, P.P. et al., Short Antisense Oligonucleotides with Novel 2'-4' Conformationaly Restricted Nucleoside Analogues Show Improved Potency without Increased Toxicity in Animals, J. Med. Chem., 52: 10-13 (2009).
Seth, P.P. et al., Structural requirements for hybridization at the 50-position are different in a-L-LNA as compared to b-D-LNA, Bioo. Med. Chem. Lett., 22: 296-299 (2012).
Seth, P.P. et al., Structure Activity Relationships of α-l-LNA Modified, Phosphorothioate Gapmer Antisense Oligonucleotides in Animals, Mol. Ther-Nuc. Acids., 1: e47 1-8 (2012).
Seth, P.P. et al., Synthesis and Biophysical Evaluation of 2',4'-Constrained 2'O-Methoxyethyl and 2',4'-Constrained 2'O-Ethyl Nucleic Acid Analogues, J. Org. Chem., 75: 1569-1581 (2010).
Sha, S.J. and Boxer, A., Treatment implications of C9ORF72, Alzheimer's Research & Therapy, 4(46): 7 pages (2012).
Shivalingam, A. et al., Molecular Requirements of High-Fidelity Replication-Competent DNA Backbones for Orthogonal Chemical Ligation, J. Am. Chem. Soc., 139(4):1575-1583 (2017).
Simon-Sanchez, J. et al., the clinical and pathological phenotype of C9ORF72 hexanucleotide repeat expansions, Brain, 135: 723-735 (2012).
Singh, P.P. et al., Universality of LNA-mediated high-affinity nucleic acid recognition, Chem. Comm., 1247-1248 (1998).
Singh, S.K. et al., Synthesis of 2'-Amino-LNA: A Novel Conformationally Restricted High-Affinity Oligonucleotide Analogue with a Handle, J. Org. Chem., 63: 10035-10039 (1998).
Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6079 (1998).
Sobkowski, M. et al., Recent Advances in H-Phosphonate Chemistry. Part 1. H-Phosphonate Esters: Synthesis and Basic Reactions, Top Curr Chem, 361:137-177 (2014).
Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).
Stout, A.K. et al., Inhibition of wound healing in mice by local interferon a/b injection, Int J Exp Pathol, 74 (1): 79-85 (1993).
Surono, A. et al., Chimeric RNA/Ethylene Bridged Nucleic Acids Promote Dystrophin Expression in Myocytes of Duchenne Muscular Dystrophy by Inducing Skipping of the Nonsense Mutation-Encoding Econ, Human Gene Therapy, 15:749-757 (2004).
Suter, S.R. et al., Structure-Guided Control of siRNA Off Target Effects, J. Am. Chem. Soc., 1-9 (2016).
Takahashi, T. et al., Interactions between the non-seed region of siRNA and RNA-binding RLC/RISC proteins, Ago and TRBP, in mammalian cells, Nucleic Acids Research, 42(8): 5256-5269 (2014).
Takeshima, Y. et al., Oligonucleotides against a splicing enhancer sequence led to dystrophin production in muscle cells from a Duchenne muscular dystrophy patient, Brain & Development, 23:788-790 (2001).
TS'O, P.O. et al., An Approach to Chemotherapy Based on Base Sequence Information and Nucleic Acid Chemistry, Ann. N. Y. Acad. Sci., 507: 220-241 (1988).
Tulic, M.K. et al Amb a 1-immunostimulatory oligodeoxynucleotide conjugate immunotherapy decreases the nasal inflammatory response, J. Allergy Clin. Immunol., 235-241 (2004).
Van Aerschot, A. et al., 1,5-Anhydrohexitol Nucleic Acids, a New Promising Antisense Construc, Angew. Chem. Int. Ed. Engl., 34: 1338-1339 (1995).
Van Deutekom, J.C.T. et al., Antisense-induced exon skipping restores dystrophin expression in DMD patient derived muscle cells, Human Molecular Genetics, 10(15):1547-1554 (2001).
Vasseur, J-J. et al., Oligonucleosides: Synthesis of a Novel Methylhydroxylamine-Linked Nucleoside Dimer and Its Incorporation into Antisense Sequences, J. Am. Chem. Soc., 114: 4006-4007 (1992).
Veedu, R.N. et al., Novel Applications of Locked Nucleic Acids, Nucleic Acids Symposium Series, 51: 29-30 (2007).
Verhagen et al., A Conformationally locked Aminomethyl C-Glycoside and Studies on Its N-Pyren-1-ylcarbonyl Derivative Inserted into Oligodeoxynucleotides, European Journal of Organic Chemistry, 2538-2548 (2006).
Wan, W.B. and Seth, P.P., The Medicinal Chemistry of Therapeutic Oligonucleotides, J. Med. Chem., 59: 9645-9667 (2016).
Wang, Y. et al., Structure of an argonaute silencing complex with a seed-containing guide DNA and target RNA duplex, Nature, 456(7224): 921-926 (2008).
Watts, J.K. and Corey, D.R., Gene silencing by siRNAs and antisense oligonucleotides in the laboratory and the clinic, J. Pathol. 226(2): 365-79 (2012).
Weiner, G. J. et al., Immunostimulatory oligodeoxynucleotides containing the CpG motif are effective as immune adjuvants in tumor antigen immunization, 94(20): 10833-10837 (1997).
Weinfeld, M., et al., Influence of nucleic acid base aromaticity on substrate reactivity with enzymes acting on single-stranded DNA, Nucleic Acids Res., 21(3): 621-626 (1993).
Whittaker, B. et al., Stereoselective synthesis of highly functionalised P-stereogenic nucleosides via palladium-catalysed P-C cross-coupling reactions, Tetrahedron Letters, 49: 6984-6987 (2008).
Woolf, T.M. et al., Specificity of antisense oligonucleotides in vivo, Prov. Natl. Aca. Sci. USA, 89: 7305-7309 (1992).
Written Opinion for PCT/JP15/50716 and English Translation, 11 pages (dated Apr. 21, 2015).
Written Opinion for PCT/JP2015/050714, and English Translation, 11 pages (dated Apr. 21, 2015).
Written Opinion for PCT/JP2015/050718 and English Translation, 6 ppages (dated Apr. 21, 2015).
Written Opinion for PCT/US2016/043542, 14 pages (dated Dec. 28, 2016).
Written Opinion for PCT/US2016/043598, 10 pages (dated Nov. 28, 2016).
Written Opinion for PCT/US2016/056123, 15 pages (dated Mar. 17, 2017).
Written Opinion for PCT/US2017/022135, 11 pages (dated Jun. 6, 2017).
Written Opinion for PCT/US2017/030753, 13 pages (dated Sep. 26, 2017).
Written Opinion for PCT/US2017/030777, 10 pages (dated Oct. 2, 2017).
Written Opinion for PCT/US2017/035837, 15 pages (dated Aug. 24, 2017).
Written Opinion for PCT/US2017/043431, ISA/US, 38 pages (dated Dec. 21, 2017).
Written Opinion for PCT/US2017/045218, 11 pages (dated Sep. 27, 2017).
Written Opinion for PCT/US2017/055601, ISR/US, 16 pages (dated Feb. 15, 2018).
Written Opinion for PCT/US2017/062996, 9 pages (dated Mar. 9, 2018).
Xu, Y. et al., Functional comparison of single- and double-stranded siRNAs in mammalian cells, Biochemical and Biophysical Research Communications, 316: 680-687 (2004).
Yasuda, K. et al., CpG motif-independent activation of TLR9 upon endosomal translocation of "natural" phosphodiester DNA, European Journal of Immunology, 431-436 (2006).
Ye, S. et al., An efficient procedure for genotyping single nucleotide polymorphisms, Nucleic Acids Research, 29(17): e88 1-8 (2001).

(56) References Cited

OTHER PUBLICATIONS

Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).

Zhang, Y. et al., Structural Isosteres of Phosphate Groups in the Protein Data Bank, J. Chem. Inf. Model, 1-18 (2017).

Zhang, Y., Investigating phosphate structural replacements through computational and experimental approaches, Academic Dissertain, University of Helsinki, 119 pages (2014).

Zhong, Z. et al., WAVE Life Sciences: Developing Stereopure Nucleic Acid Therapies for the Treatment of Genetic Neurological Diseases, World CNS Summit 2017, Boston, MA, WAVE Life Sciences, Poster, 1 page (Feb. 20-22, 2017).

Zlatev, I. et al., 5'-C-Malonyl RNA: Small Interfering RNAs Modified with 5'-Monophosphate Bioisostere Demonstrate Gene Silencing Activity, ACS Chem. Biol., 8 pages (2015).

* cited by examiner

CHIRAL AUXILIARIES

CLAIM FOR PRIORITY

This application is a U.S. National Stage of PCT/JP2011/071559 filed Sep. 22, 2011, and claims the priority benefit of U.S. provisional application 61/386,1016, filed Sep. 24, 2010, the contents of which is expressly incorporated by reference herein in its entirety.

TECHNICAL FIELD

The present invention relates to novel compounds that can act as an auxiliary group for asymmetric induction in the manufacture of phosphorus atom-modified nucleic acid derivatives.

BACKGROUND ART

Nucleic acid derivatives such as oligonucleotides are substances useful for variety of uses, such as the use for therapeutic and prophylactic treatments and diagnosis of diseases as well as the use as nanomaterials. However, natural DNAs and RNAs have a problem that they are unstable against nucleases (refer to, for example, Wada, T., "Frontier of Development of Nucleic acid Medicine", Chapter 1 Development of nucleic acid medicines, 3.3 Chemical synthesis of phosphorus atom-modified nucleic acids, pp.67-'75, CMC Publication, published on February, 2009 and the like). Meanwhile, it has been elucidated by in vivo researches that properties of antisense nucleic acids, such as sequence-specific binding ability for binding with complementary RNAs and stability against nucleases, are influenced by three-dimensional configuration of phosphorus atom in nucleic acid derivatives. Therefore, it is desired to provide a method for preparing a nucleic acid derivative having stability against decomposition by a nuclease and having affinity for a complementary DNA or RNA sequence in vivo or in vitro by controlling three-dimensional configuration of phosphorus atom. It is also desired to provide a means that enables easy preparation of such nucleic acid derivatives by the solid phase method or the liquid phase method, and various chemical modifications of nucleic acid derivatives at sugar or base moieties.

From the aforementioned points of view, nucleic acid derivatives having a phosphorus atom modified with a sulfur atom or boron atom have been focused, and several techniques for controlling the three-dimensional configuration of phosphorus atom in the manufacture of such derivatives have been provided. For example, Japanese Patent Unexamined Publication (KOKAI) No. 2005-89441 discloses a method for preparing a phosphorus atom-modified nucleic acid derivative of high stereoregularity, of which process utilizes a compound represented by the general formula (3) as an activator, and proceeds via a compound represented by the general formula (13) as a reaction intermediate (oxazaphospholidine method). In this method, an optically active nucleoside 3'-phosphoramidite represented by the general formula (1) is prepared, and reacted as a starting material (monomer) with a nucleoside together with the activator represented by the general formula (3), and the resultant is appropriately protected, and then reacted with an electrophilic reagent to prepare the compound represented by the general formula (13). However, this method has problems that the yield of the synthesis of the monomer is low, the monomer is chemically unstable, and thus industrial application thereof is considered to be difficult.

In International Patent Publication WO2010/064146, a method for preparing a phosphorus atom-modified nucleic acid derivative is proposed, which uses an auxiliary group for asymmetric induction (henceforth also referred to as "chiral auxiliary" in the specification). This publication discloses a method for preparing a phosphorus atom-modified nucleic acid derivative in a high asymmetric yield, in which a compound represented by Formula 3 is reacted with a phosphorus atom of a nucleic acid derivative to prepare a compound of Formula 4 wherein D is a group represented by Formula A (residue of the compound of Formula 3) or a compound represented by Formula 5, and then the chiral auxiliary is removed. The outline of this method is shown in the following scheme. This method, utilizing the chiral auxiliary, can use an achiral H-phosphonate monoester as a starting material, which is chemically stable and can be synthesized in a large scale, and can perform the condensation reaction by forming the optically active monomer within the reaction system without isolation and purification thereof. Therefore, the method is more industrially advantageous compared with the method disclosed in Japanese Patent Unexamined Publication (KOKAI) No. 2005-89441.

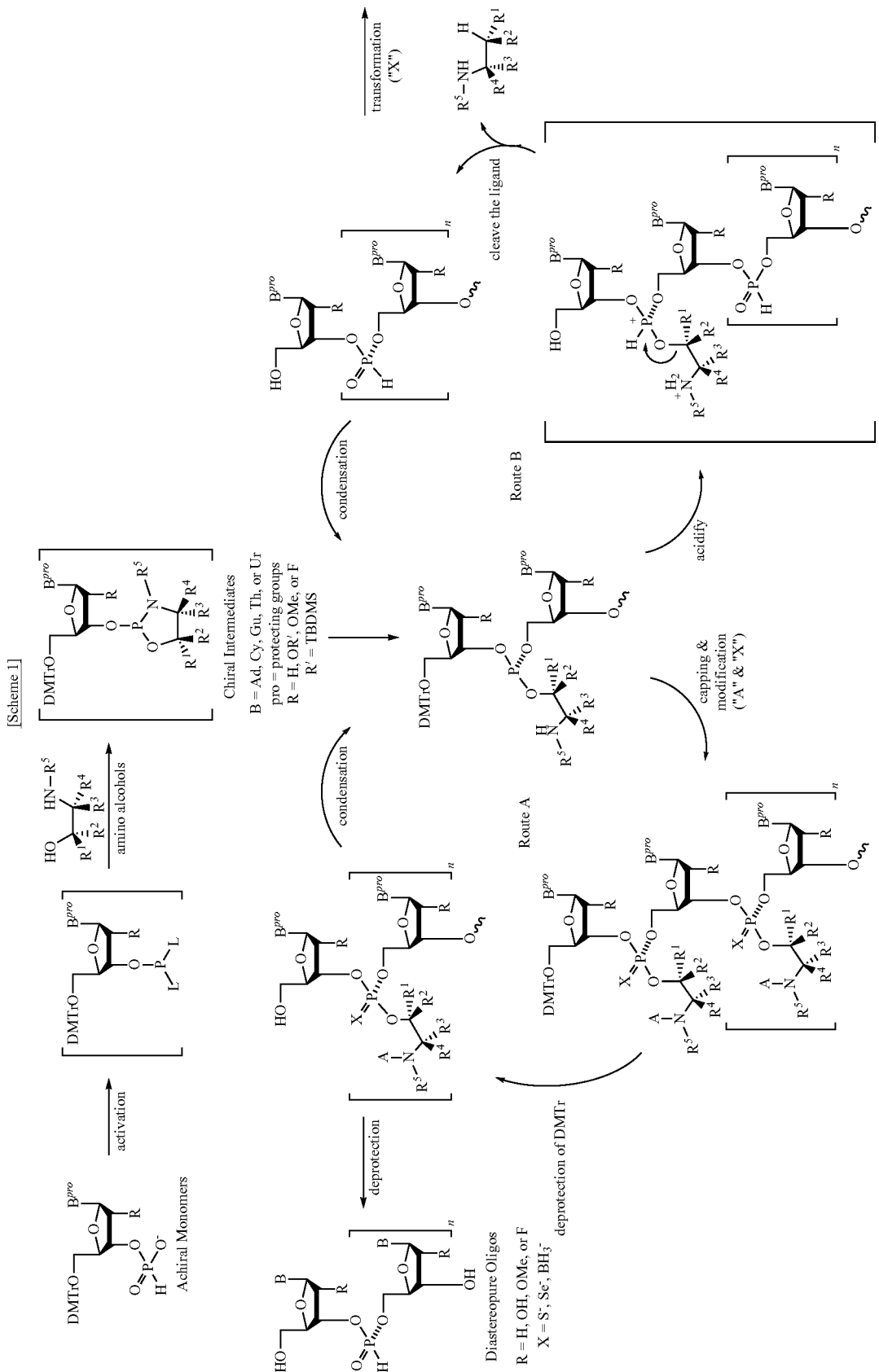

-continued
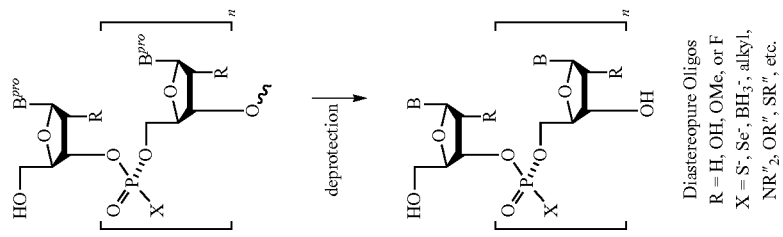

The compound used for introducing the chiral auxiliary in the method described above is a compound having the following structure (compound represented by Formula 3 in the aforementioned publication).

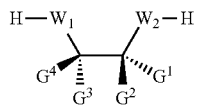

[In the formula, $W_1$ and $W_2$ independently represent $-NG^5-$, $-O-$, or $-S-$, and $G^1$, $G^2$, $G^3$, $G^4$, and $G^5$ independently represent hydrogen atom, an alkyl group, an aralkyl group, a cycloalkyl group, a cycloalkylalkyl group, a heterocyclic group, a heteroaryl group, or an aryl group, or two of $G^1$, $G^2$, $G^3$ $G^4$, and $G^5$ bind together to become $G^6$ and represent a saturated or partially unsaturated or unsaturated monocyclic, polycyclic, condensed ring or non-condensed ring hydrocarbon ring group or heteroatom-containing ring group comprising up to about 20 members (provided that at most four of $G^1$, $G^2$, $G^3$, $G^4$, and $G^5$ can become $G^6$)].

However, this publication discloses only the following four kinds of compounds as the compound of Formula 3, and all of these are compounds wherein $W_1$ is $-NG^5-$, and $G^4$ and $G^5$ bind together to form a ring system according to the aforementioned definitions. In this method, the chiral auxiliary introduced by using the compound represented by Formula O or Formula P is removed under a basic condition, and the chiral auxiliary introduced by using the compound represented by Formula Q or Formula R is removed under an acidic condition. In the aforementioned scheme, Route A represents a synthetic method in which the chiral auxiliary is removed under a basic condition in the final step of the condensation cycle for chain length extension, and Route B represents a synthetic method in which the chiral auxiliary is removed under an acidic condition in each condensation cycle for chain length extension.

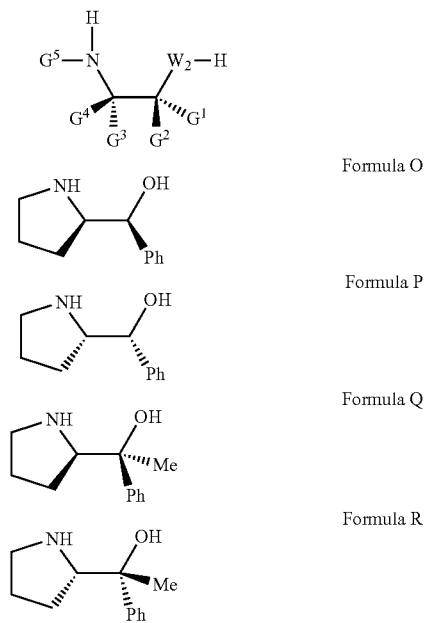

Formula O

Formula P

Formula Q

Formula R

PRIOR ART REFERENCES

Patent Documents

Patent document 1: Japanese Patent Unexamined Publication (KOKAI) No. 2005-89441
Patent document 2: International Patent Publication WO2010/064146

Non-Patent Document

Non-patent document 1: Wada, T., "Frontier of Development of Nucleic acid Medicine", Chapter 1 Development of nucleic acid medicines, 3.3 Chemical synthesis of phosphorus atom-modified nucleic acids, pp.67-'75, CMC Publication, published on February, 2009

SUMMARY OF THE INVENTION

Object to be Achieved by the Invention

An object of the present invention is to provide a means for efficiently preparing a phosphorus atom-modified nucleic acid derivative with high stereoregularity. More specifically, the object of the present invention is to provide a chiral auxiliary useful for efficiently preparing a phosphorus atom-modified nucleic acid derivative with high stereoregularity and a compound for introducing the chiral auxiliary.

Means for Achieving the Object

The inventors of the present invention conducted various researches to achieve the aforementioned object, and recognized that the chiral auxiliaries introduced by using four kinds of the compounds disclosed in International Patent Publication WO2010/064146 formed a chemically stable bond with a phosphorus atom, and a treatment under a severe condition was required for removal thereof in the following step, and from these reasons, it sometimes becomes difficult to efficiently synthesize a long chain nucleic acid derivative, because a decomposition reaction might proceed to produce by-products or the like.

More specifically, the chiral auxiliary introduced by using the compound represented by Formula Q or Formula R among the four kinds of the aforementioned compounds can be removed by generating a cation under a strongly acidic condition, for example, by using 1% trifluoroacetic acid (TFA) in dichloromethane, according to the following $S_N1$ mechanism. However, since this acidic condition is also a condition that causes removal of an adenine base of which base moiety is protected with an acyl type protective group (depurination) (for adenine bases, an acyl type protective group is generally introduced), there arises a problem that when the aforementioned chiral auxiliary is used, the adenine base must be protected with a protective group of amidine type, trityl type, diacyl type or the like (in the following scheme, Bs represents a nucleobase, Me represents methyl group, and Ph represents phenyl group).

[Scheme 2]

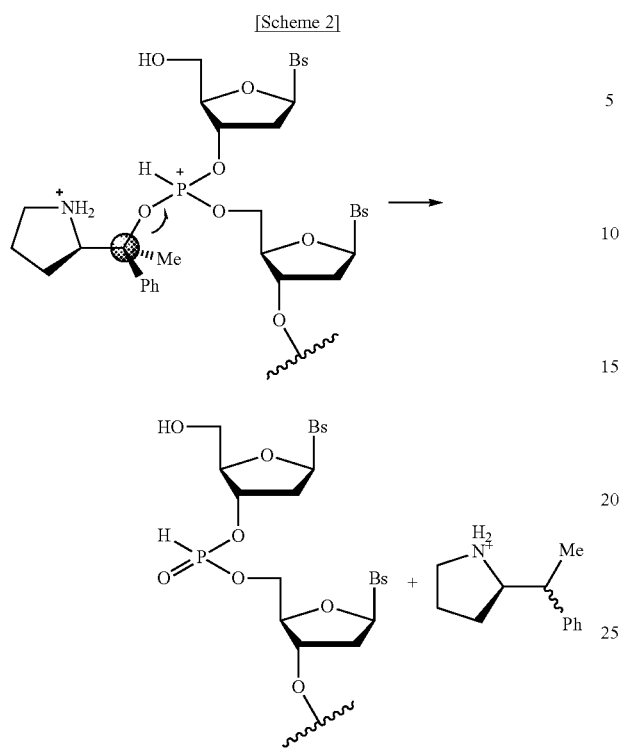

[Scheme 3]

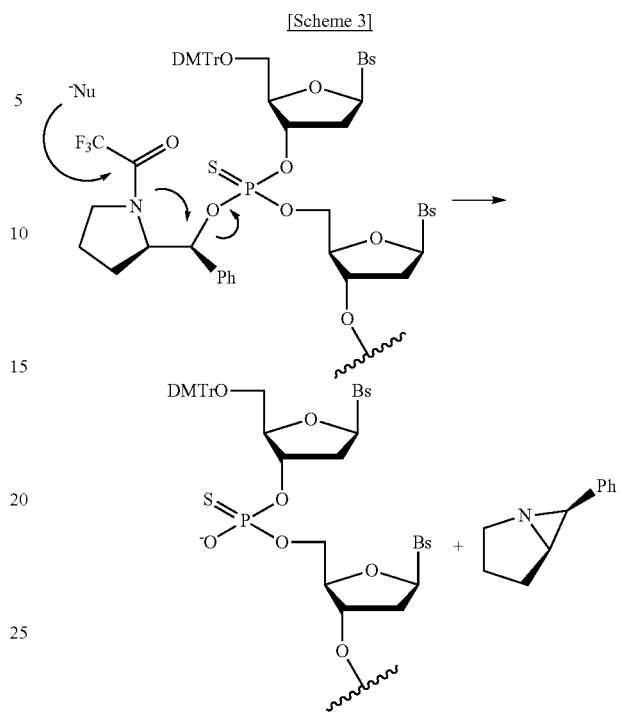

The inventors of the present invention further conducted researches, and as a result, found that when a chiral auxiliary, not specifically disclosed in the aforementioned International Patent Publication WO2010/064146, was introduced by using a compound represented by the following general formula (I), the reaction advanced in a high asymmetric yield, and the chiral auxiliary was successfully removed according to the $S_N1$ mechanism under a milder acidic condition, for example, a condition of using 3% dichloroacetic acid (DCA) in dichloromethane, which is used for removal of dimethoxytrityl (DMTr) group at the 5' end for chain length extension in the nucleic acid synthesis cycle, and that a long chain nucleic acid derivative was successfully and highly efficiently producible by using this chiral auxiliary.

The chiral auxiliary introduced by using the compound represented by Formula O or Formula P, among the four kinds of the compounds specifically disclosed in the aforementioned International Patent Publication WO2010/064146, can be removed as an aziridine compound under a basic condition, for example, by a treatment using aqueous ammonia at 55° C. for 12 hours. Although this removal of the asymmetric protective group under such a basic condition does not cause a problem in synthesis of a comparatively short DNA strand, it causes problems in synthesis of a relatively long DNA strand or synthesis of a chemically unstable RNA strand, for example, side reactions such as decomposition of the strand may occur or it may become difficult to completely remove the group (in the following scheme, Bs represents a nucleobase, Ph represents phenyl group, Nu represents a nucleophilic agent, and DMTr represents dimethoxytrityl group).

The inventors of the present invention further conducted researches, and as a result, found that if a chiral auxiliary was introduced by using a compound represented by the following general formula (XI), which is not specifically disclosed in the aforementioned International Patent Publication WO2010/064146, the reaction advanced in a high asymmetric yield, and the chiral auxiliary was successfully removed under a milder acidic condition according to the β-elimination mechanism, and that a long chain nucleic acid derivative was successfully and highly efficiently producible by using this chiral auxiliary.

The present invention was accomplished on the basis of these findings.

The present invention thus provides a compound represented by the following general formula (I):

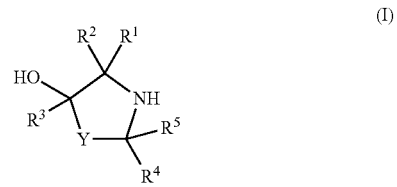

[in the formula, $R^1$ and $R^2$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent; $R^3$ represents an aryl group which may have a substituent, or an alkyl group which may have a substituent; $R^4$ and $R^5$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent; Y represents -$Y^1$-$Y^2$-, $Y^1$ represents —C($R^6$)($R^7$)— ($R^6$ and $R^7$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent, and $R^7$ may bind with the aryl group represented by $R^3$ to form a ring), or an o-aryldiyl group which may have a substituent (the aryl ring of the aryldiyl group may bind with the aryl group represented by $R^3$ to form a ring), and $Y^2$ represents a single bond or —C($R^8$)($R^9$)— ($R^8$ and $R^9$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent)], or a salt thereof.

According to a preferred embodiment of the aforementioned invention, there is provided the aforementioned compound or a salt thereof, wherein $R^1$ and $R^2$ are hydrogen atom or an alkyl group, $R^3$ is phenyl group, $R^4$ and $R^5$ are hydrogen atom or an alkyl group, and Y is —C($R^6$)($R^7$)— ($R^6$ and $R^7$ are independently hydrogen atom or an alkyl group, and when $R^7$ represents an alkyl group, $R^7$ may bind with the phenyl group represented by $R^3$ to form a ring), o-phenylene group, or naphthalene-1,2-diyl group.

According to more preferred embodiments, the following compounds are provided.

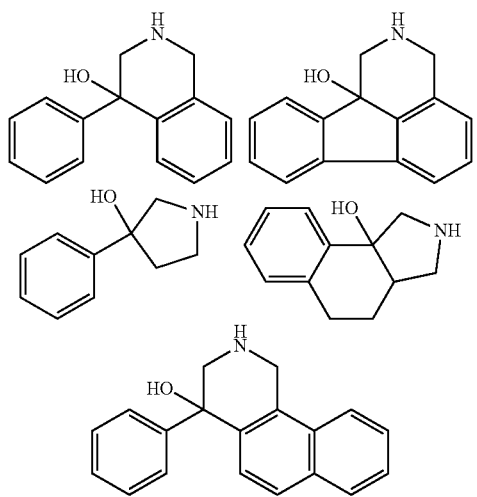

As another aspect, the present invention provides a nucleic acid derivative, wherein a chiral auxiliary represented by the following general formula (II):

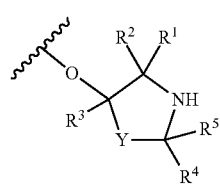

(II)

(the symbols in the formula have the same meanings as those defined above) binds to a phosphorus atom.

According to a preferred embodiment of this invention, there is provided a nucleic acid derivative represented by the following general formula (III):

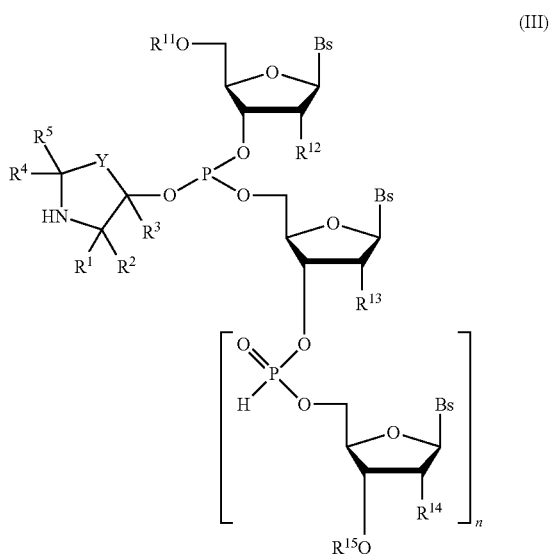

(III)

(in the formula, $R^1$, $R^2$, $R^3$, $R^4$, $R^5$, and Y have the same meanings as those defined above; $R^{11}$ represents hydrogen atom, or a protective group of hydroxyl group; $R^{12}$, $R^{13}$, and $R^{14}$ independently represent hydrogen atom, an alkoxy group, fluorine atom, or a protected hydroxyl group; $R^{15}$ represents hydrogen atom, a protective group of hydroxyl group, or a solid phase support, which may bind via a linker as required; Bs represents a nucleobase; and n represents 0 or an integer of 1 or larger).

The present invention also provides a nucleotide derivative represented by the following general formula (IV):

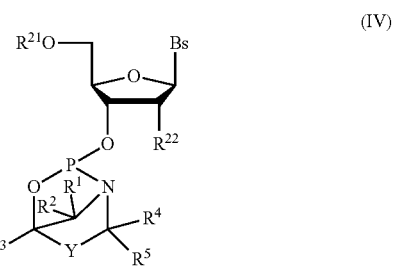

(IV)

(in the formula, $R^1$, $R^2$, $R^3$, $R^4$, $R^5$, and Y have the same meanings as those defined above; $R^{21}$ represents a protective group of hydroxyl group; $R^{22}$ represent hydrogen atom, an alkoxy group, fluorine atom, or a protected hydroxyl group; and Bs represents a nucleobase).

The present invention further provides a method for preparing a nucleic acid derivative, which comprises the following steps:

(a) the step of reacting a nucleic acid derivative represented by the following general formula (V):

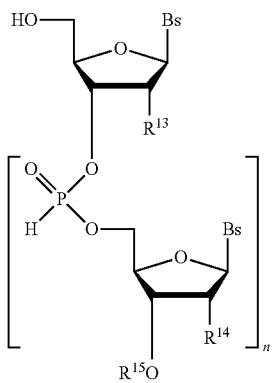

(in the formula, $R^{13}$, $R^{14}$, $R^{15}$, and n have the same meanings as those defined above) and a nucleotide derivative represented by the aforementioned general formula (IV) ($R^1$, $R^2$, $R^3$, $R^4$, $R^5$, and Y have the same meanings as those defined above; $R^{21}$ represents a protective group of hydroxyl group; $R^{22}$ represents hydrogen atom, an alkoxy group, fluorine atom, or a protected hydroxyl group; and Bs represents a nucleobase) to prepare a nucleic acid derivative represented by the aforementioned general formula (III) ($R^1$, $R^2$, $R^3$, $R^4$, $R^5$, Y and n have the same meanings as those defined above; $R^{11}$ represents a protective group of hydroxyl group; $R^{12}$, $R^{13}$, and $R^{14}$ independently represent hydrogen atom, an alkoxy group, fluorine atom, or a protected hydroxyl group; $R^{15}$ represents a solid phase support, which may bind via a linker as required; and Bs represents a nucleobase);
(b) the step of repeating the step of removing the protective group of hydroxyl group represented by $R^{11}$ from the nucleic acid derivative represented by the general formula (III) obtained by the aforementioned step (a) and reacting the obtained nucleic acid derivative and a nucleotide derivative represented by the general formula (IV) as required;
(c) the step of removing the chiral auxiliary(s) represented by the general formula (II) under an acidic condition to prepare a nucleic acid derivative represented by the following general formula (VI):

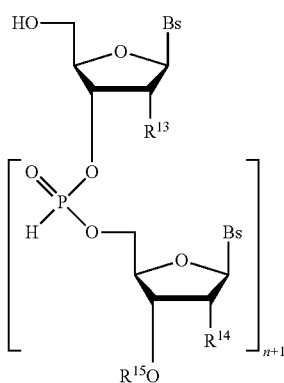

(in the formula, $R^{13}$, $R^{14}$, $R^{15}$, and n have the same meanings as those defined above); and
(d) the step of modifying the phosphorus atom(s) of the nucleic acid derivative obtained in the aforementioned step (c) and then removing the protective group(s) as required.

In the aforementioned method, for the acidic condition for removing the chiral auxiliary represented by the general formula (II) in the step (c), for example, 3% dichloroacetic acid (DCA) in dichloromethane can be used.

The modification of the phosphorus atom in the step (d) may be introduction of a group represented by X (X represents an alkylthio group which may have a substituent, an alkenylthio group which may have a substituent, an alkynylthio group which may have a substituent, an arylthio group which may have a substituent, thiol group, an alkoxy group which may have a substituent, —$BH_3$, —$Se^-$, an alkyl group which may have a substituent, an alkenyl group which may have a substituent, an alkynyl group which may have a substituent, an aryl group which may have a substituent, an acyl group which may have a substituent, or —$N(R^{116})(R^{117})$ ($R^{116}$ and $R^{117}$ independently represent hydrogen atom, an alkyl group which may have a substituent, an alkenyl group which may have a substituent, an alkynyl group which may have a substituent, or an aryl group which may have a substituent) on the phosphorus atom.

As another aspect, the present invention provides a compound represented by the following general formula (XI):

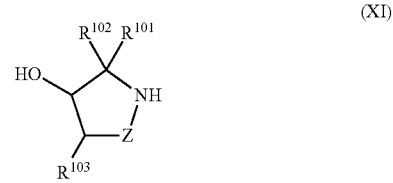

[in the formula, $R^{101}$ and $R^{102}$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent; $R^{103}$ represents cyano group, a halogen atom, a halogenated alkyl group which may have a substituent, a halogenated alkanoyl group which may have a substituent, sulfonyl group, a halogenated alkylsulfonyl group which may have a substituent, or nitro group; Z represents -$Z^1$-$Z^2$-, $Z^1$ represents —$C(R^{104})(R^{105})$— ($R^{104}$ and $R^{105}$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent), and $Z^2$ represents a single bond or —$C(R^{106})(R^{107})$— ($R^{106}$ and $R^{107}$ independently represent hydrogen atom, an alkyl group which may have and a substituent, an alkenyl group which may have a substituent, an alkynyl group which may have a substituent, an alkoxy group which may have a substituent, an aralkyl group which may have a substituent, or an aryl group which may have a substituent)], or a salt thereof.

According to a preferred embodiment of the aforementioned invention, there is provided the aforementioned compound or a salt thereof, wherein $R^{101}$ and $R^{102}$ are hydrogen atom or an alkyl group, $R^{103}$ is cyano group, and Z is —$C(R^{104})(R^{105})$— ($R^{104}$ and $R^{105}$ are hydrogen atom or an alkyl group), and according to a more preferred embodiment, there is provided the aforementioned compound or a salt thereof, wherein $R^{101}$ and $R^{102}$ are hydrogen atoms, $R^{103}$ is cyano group, and Z is —$C(R^{104})(R^{105})$— ($R^{104}$ and $R^{105}$ are hydrogen atoms).

The present invention also provides a nucleic acid derivative, wherein a chiral auxiliary represented by the following general formula (XII):

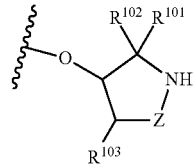

(XII)

(the symbols in the formula have the same meanings as those defined above) binds to a phosphorus atom.

According to a preferred embodiment of this invention, there is provided a nucleic acid derivative represented by the following general formula (XIII):

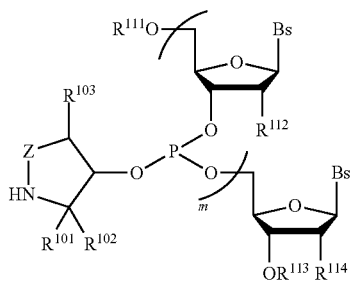

(XIII)

(in the formula, $R^{101}$, $R^{102}$, $R^{103}$, and Z have the same meanings as those defined above; $R^{111}$ represents hydrogen atom, or a protective group of hydroxyl group; $R^{112}$ and $R^{114}$ independently represent hydrogen atom, an alkoxy group, fluorine atom, or a protected hydroxyl group; $R^{113}$ represents hydrogen atom, a protective group of hydroxyl group, or a solid phase support, which may bind via a linker as required; Bs represents a nucleobase; and m represents an integer of 1 or larger).

The present invention also provides a nucleotide derivative represented by the following general formula (XIV):

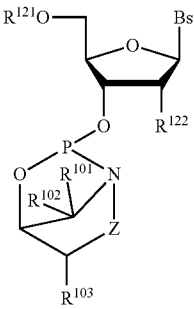

(XIV)

(in the formula, $R^{101}$, $R^{102}$, $R^{103}$, and Z have the same meanings as those defined above; R121 represents a protective group of hydroxyl group; $R^{122}$ represents hydrogen atom, an alkoxy group, fluorine atom, or a protected hydroxyl group; and Bs represents a nucleobase).

As another aspect of the present invention, there is provided a method for preparing a nucleic acid derivative comprising the following steps:

(a) the step of reacting a nucleic acid derivative represented by the following general formula (XIII'):

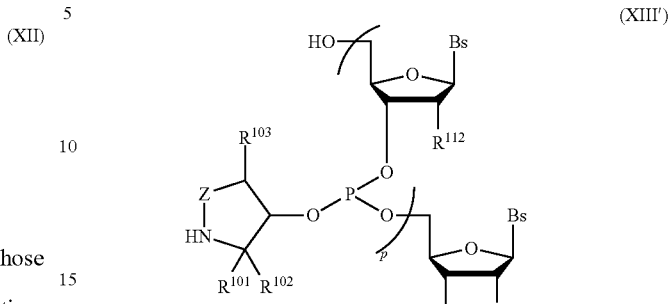

(XIII')

(in the formula, $R^{101}$, $R^{102}$, $R^{103}$, and Z have the same meanings as those defined above, $R^{112}$ and $R^{114}$ independently represent hydrogen atom, an alkoxy group, fluorine atom, or a protected hydroxyl group; $R^{113}$ represents a solid phase support, which may bind via a linker as required; p represents 0 or an integer of 1 or larger; and Bs represents a nucleobase)

and a nucleotide derivative represented by the aforementioned general formula (XIV) (R121 represents a protective group of hydroxyl group; and $R^{122}$ represents hydrogen atom, an alkoxy group, fluorine atom, or a protected hydroxyl group), then introducing X (X represents thiol group, $—BH_3$, or $—Se^-$) by using an electrophilic agent, and removing the protective group of hydroxyl group represented by $R^{121}$ to prepare a nucleic acid derivative represented by the following general formula (XV):

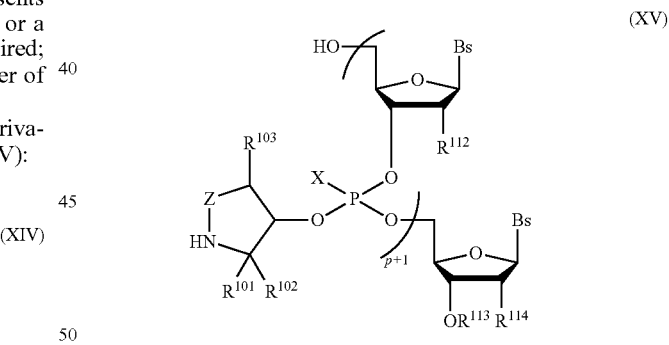

(XV)

(in the formula, $R^{101}$, $R^{102}$, $R^{103}$, and Z have the same meanings as those defined above, $R^{112}$ and $R^{114}$ independently represent hydrogen atom, an alkoxy group, fluorine atom, or a protected hydroxyl group; $R^{113}$ represents a solid phase support, which may bind via a linker as required; p represents 0 or an integer of 1 or larger; and Bs represents a nucleobase), and repeating the aforementioned reaction as required to prepare a nucleic acid derivative represented by the general formula (XV); and (b) the step of removing the chiral auxiliary represented by the general formula (XII) from the nucleic acid derivative represented by the aforementioned general formula (XV), which is obtained in the aforementioned step (a), under a basic condition to prepare a nucleic acid derivative represented by the following general formula (XVII):

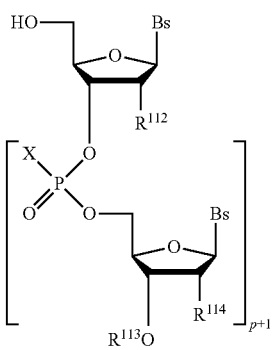

(XVII)

(in the formula, $R^{112}$, $R^{113}$, $R^{114}$, and p have the same meanings as those defined above).

Modes for Carrying out the Invention

As the alkyl group, a linear, branched or cyclic alkyl group, or an alkyl group consisting of a combination of the foregoing alkyl groups can be used. For example, a $C_1$-$C_{15}$ alkyl is preferred, a $C_1$-$C_{10}$ alkyl group is more preferred, and a $C_1$-$C_6$ alkyl group is still more preferred. The same shall apply to alkyl moieties of other substituents having an alkyl moiety (for example, alkoxy group, halogenated alkyl group, and the like). Examples include, for example, methyl group, ethyl group, n-propyl group, isopropyl group, n-butyl group, isobutyl group, sec-butyl group, tert-butyl group, n-pentyl group, isopentyl group, 2-methylbutyl group, 1-methylbutyl group, neopentyl group, 1,2-dimethylpropyl group, 1-ethylpropyl group, n-hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group, 1-ethylbutyl group, 1-ethyl-1-methylpropyl group, n-heptyl group, n-octyl group, n-nonyl group, n-decyl group, n-undecyl group, n-dodecyl group, n-tridecyl group, n-tetradecyl group, n-pentadecyl group, cyclopropyl group, cyclobutyl group, cyclopentyl group, cyclohexyl group, cycloheptyl group, cyclooctyl group, cyclopropylmethyl group, 1-cyclopropylethyl group, 2-cyclopropylethyl group, 3-cyclopropylpropyl group, 4-cyclopropylbutyl group, 5-cyclopropylpentyl group, 6-cyclopropylhexyl group, cyclobutylmethyl group, cyclopentylmethyl group, cyclobutylmethyl group, cyclopentylmethyl group, cyclohexylmethyl group, cyclohexylpropyl group, cyclohexylbutyl group, cycloheptylmethyl group, cyclooctylmethyl group, 6-cyclooctylhexyl group, and the like, but are not limited to these examples. The cyclic alkyl group encompasses a saturated heterocyclic group corresponding to a heteroaryl group in which all double bonds are replaced with single bonds.

As the alkenyl group, a linear, branched or cyclic alkenyl group, or an alkenyl group consisting of a combination of the foregoing alkenyl groups can be used. For example, a $C_2$-$C_{15}$ alkenyl group is preferred, a $C_2$-$C_{10}$ alkenyl group is more preferred, and a $C_2$-$C_6$ alkenyl group is still more preferred. Although the number of the double bond contained in the alkenyl group is not particularly limited, for example, one to several double bonds are contained, and about 1 or 2 double bonds are preferably contained. Examples include, for example, vinyl group, prop-1-en-1-yl group, an aryl group, isopropenyl group, but-1-en-1-yl group, but-2-en-1-yl group, but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group, 4-methylpent-3-en-1-yl group, 4-methylpent-3-en-1-yl group, hept-1-en-1-yl group, hept-6-en-1-yl group, oct-1-en-1-yl group, oct-7-en-1-yl group, non-1-en-1-yl group, non-8-en-1-yl group, dec-1-en-1-yl group, dec-9-en-1-yl group, undec-1-en-1-yl group, undec-10-en-1-yl group, dodec-1-en-1-yl group, dodec-11-en-1-yl group, tridec-1-en-1-yl group, tridec-12-en-1-yl group, tetradec-1-en-1-yl group, tetradec-13-en-1-yl group, pentadec-1-en-1-yl group, pentadec-14-en-1-yl group, 2-cyclopropen-1-yl group, 2-cyclobuten-1-yl group, 2-cyclopenten-1-yl group, 3-cyclopenten-1-yl group, 2-cyclohexen-1-yl group, 3-cyclohexen-1-yl group, 1-cyclobuten-1-yl group, 1-cyclopenten-1-yl group, 2-cyclohexen-1-ylmethyl group, 2-cyclohexen-1-ylmethyl group, and the like, but are not limited to these examples. The cyclic alkenyl group encompasses a partially saturated carbon ring group corresponding to an aryl group in which an arbitrary number of double bonds, except for at least one double bond, are replaced with single bonds, and a partially saturated heterocyclic group corresponding to a heteroaryl group in which an arbitrary number of double bonds, except for at least one double bond, are replaced with single bonds.

As the alkynyl group, a linear or branched alkynyl group can be used. For example, a $C_2$-$C_{15}$ alkynyl group is preferred, a $C_2$-$C_{10}$ alkynyl group is more preferred, and a $C_2$-$C_6$ alkynyl group is still more preferred. Although the number of the triple bond contained in the alkynyl group is not particularly limited, for example, one to several triple bonds may be contained, and about 1 or 2 triple bonds are preferably contained. The alkynyl group may contain one to several double bonds. The alkynyl group may be combined with a cyclic alkyl group or a cyclic alkenyl group. Examples include, for example, ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group, hex-5-yn-1-yl group, hept-1-yn-1-yl group, hept-6-yn-1-yl group, oct-1-yn-1-yl group, oct-7-yn-1-yl group, non-1-yn-1-yl group, non-8-yn-1-yl group, dec-1-yn-1-yl group, dec-9-yn-1-yl group, undec-1-yn-1-yl group, undec-10-yn-1-yl group, dodec-1-yn-1-yl group, dodec-11-yn-1-yl group, tridec-1-yn-1-yl group, tridec-12-yn-1-yl group, tetradec-1-yn-1-yl group, tetradec-13-yn-1-yl group, pentadec-1-yn-1-yl group, pentadec-14-yn-1-yl group, and the like.

As the aryl group, a monocyclic or condensed polycyclic aromatic hydrocarbon group can be used, and examples include, for example, phenyl group, 1-naphthyl group, 2-naphthyl group, anthranyl group, phenanthryl group, and the like. Phenyl group is preferred.

The term aryl group used in the specification encompasses a heteroaryl group. As the heteroaryl group, a monocyclic or condensed polycyclic aromatic heterocyclic group can be used. Although number of ring-constituting heteroatom is not particularly limited, it may contain one to several heteroatoms, and it preferably contains about 1 to 5 heteroatoms. When two or more ring-constituting heteroatoms are contained, they may be the same or different. Examples of the heteroatom include, for example, oxygen atom, nitrogen atom, sulfur atom, and the like, but are not limited to these examples.

Examples of the monocyclic heteroaryl group include, for example, a 5- to 7-membered monocyclic heteroaryl group such as 2-furyl group, 3-furyl group, 2-thienyl group, 3-thienyl group, 1-pyrrolyl group, 2-pyrrolyl group, 3-pyrrolyl group, 2-oxazolyl group, 4-oxazolyl group, 5-oxazolyl group, 3-isoxazolyl group, 4-isoxazolyl group, 5-isoxazolyl group, 2-thiazolyl group, 4-thiazolyl group, 5-thiazolyl group, 3-isothiazolyl group, 4-isothiazolyl group, 5-isothiazolyl group, 1-imidazolyl group, 2-imidazolyl group, 4-imidazolyl group, 5-imidazolyl group, 1-pyrazolyl group, 3-pyrazolyl group, 4-pyrazolyl group, 5-pyrazolyl group, (1,2,3-oxadiazol)-4-yl group, (1,2,3-oxadiazol)-5-yl group, (1,2,4-oxadiazol)-3-yl group, (1,2,4-oxadiazol)-5-yl group, (1,2,5-oxadiazol)-3-yl group, (1,2,5-oxadiazol)-4-yl group, (1,3,4-oxadiazol)-2-yl group, (1,3,4-oxadiazol)-5-yl group, furazanyl group, (1,2,3-thiadiazol)-4-yl group, (1,2,3-thiadiazol)-5-yl group, (1,2,4-thiadiazol)-3-yl group, (1,2,4-thiadiazol)-5-yl group, (1,2,5-thiadiazol)-3-yl group, (1,2,5-thiadiazol)-4-yl group, (1,3,4-thiadiazol)-2-yl group, (1,3,4-thiadiazol)-5-yl group, (1H-1,2,3-triazol)-1-yl group, (1H-1,2,3-triazol)-4-yl group, (1H-1,2,3-triazol)-5-yl group, (2H-1,2,3-triazol)-2-yl group, (2H-1,2,3-triazol)-4-yl group, (1H-1,2,4-triazol)-1-yl group, (1H-1,2,4-triazol)-3-yl group, (1H-1,2,4-triazol)-5-yl group, (4H-1,2,4-triazol)-3-yl group, (4H-1,2,4-triazol)-4-yl group, (1H-tetrazol)-1-yl group, (1H-tetrazol)-5-yl group, (2H-tetrazol)-2-yl group, (2H-tetrazol)-5-yl group, 2-pyridyl group, 3-pyridyl group, 4-pyridyl group, 3-pyridazinyl group, 4-pyridazinyl group, 2-pyrimidinyl group, 4-pyrimidinyl group, 5-pyrimidinyl group, 2-pyrazinyl group, (1,2,3-triazin)-4-yl group, (1,2,3-triazin)-5-yl group, (1,2,4-triazin)-3-yl group, (1,2,4-triazin)-5-yl group, (1,2,4-triazin)-6-yl group, (1,3,5-triazin)-2-yl group, 1-azepinyl group, 1-azepinyl group, 2-azepinyl group, 3-azepinyl group, 4-azepinyl group, (1,4-oxazepin)-2-yl group, (1,4-oxazepin)-3-yl group, (1,4-oxazepin)-5-yl group, (1,4-oxazepin)-6-yl group, (1,4-oxazepin)-7-yl group, (1,4-thiazepin)-2-yl group, (1,4-thiazepin)-3-yl group, (1,4-thiazepin)-5-yl group, (1,4-thiazepin)-6-yl group, and (1,4-thiazepin)-7-yl group, but are not limited to these examples.

Examples of the condensed polycyclic heteroaryl group include, for example, a 8- to 14-membered condensed polycyclic heteroaryl group such as 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzo[b]thienyl group, 3-benzo[b]thienyl group, 4-benzo[b]thienyl group, 5-benzo[b]thienyl group, 6-benzo[b]thienyl group, 7-benzo[b]thienyl group, 1-benzo[c]thienyl group, 4-benzo[c]thienyl group, 5-benzo[c]thienyl group, 1-indolyl group, 1-indolyl group, 2-indolyl group, 3-indolyl group, 4-indolyl group, 5-indolyl group, 6-indolyl group, 7-indolyl group, (2H-isoindol)-1-yl group, (2H-isoindol)-2-yl group, (2H-isoindol)-4-yl group, (2H-isoindol)-5-yl group, (1H-indazol)-1-yl group, (1H-indazol)-3-yl group, (1H-indazol)-4-yl group, (1H-indazol)-5-yl group, (1H-indazol)-6-yl group, (1H-indazol)-7-yl group, (2H-indazol)-1-yl group, (2H-indazol)-2-yl group, (2H-indazol)-4-yl group, (2H-indazol)-5-yl group, 2-benzoxazolyl group, 2-benzoxazolyl group, 4-benzoxazolyl group, 5-benzoxazolyl group, 6-benzoxazolyl group, 7-benzoxazolyl group, (1,2-benzisoxazol)-3-yl group, (1,2-benzisoxazol)-4-yl group, (1,2-benzisoxazol)-5-yl group, (1,2-benzisoxazol)-6-yl group, (1,2-benzisoxazol)-7-yl group, (2,1-benzisoxazol)-3-yl group, (2,1-benzisoxazol)-4-yl group, (2,1-benzisoxazol)-5-yl group, (2,1-benzisoxazol)-6-yl group, (2,1-benzisoxazol)-7-yl group, 2-benzothiazolyl group, 4-benzothiazolyl group, 5-benzothiazolyl group, 6-benzothiazolyl group, 7-benzothiazolyl group, (1,2-benzisothiazol)-3-yl group, (1,2-benzisothiazol)-4-yl group, (1,2-benzisothiazol)-5-yl group, (1,2-benzisothiazol)-6-yl group, (1,2-benzisothiazol)-7-yl group, (2,1-benzisothiazol)-3-yl group, (2,1-benzisothiazol)-4-yl group, (2,1-benzisothiazol)-5-yl group, (2,1-benzisothiazol)-6-yl group, (2,1-benzisothiazol)-7-yl group, (1,2,3-benzoxadiazol)-4-yl group, (1,2,3-benzoxadiazol)-5-yl group, (1,2,3-benzoxadiazol)-6-yl group, (1,2,3-benzoxadiazol)-7-yl group, (2,1,3-benzoxadiazol)-4-yl group, (2,1,3-benzoxadiazol)-5-yl group, (1,2,3-benzothiadiazol)-4-yl group, (1,2,3-benzothiadiazol)-5-yl group, (1,2,3-benzothiadiazol)-6-yl group, (1,2,3-benzothiadiazol)-7-yl group, (2,1,3-benzothiadiazol)-4-yl group, (2,1,3-benzothiadiazol)-5-yl group, (1H-benzotriazol)-1-yl group, (1H-benzotriazol)-4-yl group, (1H-benzotriazol)-5-yl group, (1H-benzotriazol)-6-yl group, (1H-benzotriazol)-7-yl group, (2H-benzotriazol)-2-yl group, (2H-benzotriazol)-4-yl group, (2H-benzotriazol)-5-yl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 3-cinnolinyl group, 4-cinnolinyl group, 5-cinnolinyl group, 6-cinnolinyl group, 7-cinnolinyl group, 8-cinnolinyl group, 2-quinazolinyl group, 4-quinazolinyl group, 5-quinazolinyl group, 6-quinazolinyl group, 7-quinazolinyl group, 8-quinazolinyl group, 2-quinoxalinyl group, 5-quinoxalinyl group, 6-quinoxalinyl group, 1-phthalazinyl group, 5-phthalazinyl group, 6-phthalazinyl group, 2-naphthyridinyl group, 3-naphthyridinyl group, 4-naphthyridinyl group, 2-purinyl group, 6-purinyl group, 7-purinyl group, 8-purinyl group, 2-pteridinyl group, 4-pteridinyl group, 6-pteridinyl group, 7-pteridinyl group, 1-carbazolyl group, 2-carbazolyl group, 3-carbazolyl group, 4-carbazolyl group, 9-carbazolyl group, 2-(α-carbolinyl) group, 3-(α-carbolinyl) group, 4-(α-carbolinyl) group, 5-(α-carbolinyl) group, 6-(α-carbolinyl) group, 7-(α-carbolinyl) group, 8-(α-carbolinyl) group, 9-(α-carbolinyl) group, 1-(6-carbolinyl) group, 3-(β-carbolinyl) group, 4-(β-carbolinyl) group, 5-(β-carbolinyl) group, 6-(β-carbolinyl) group, 7-(β-carbolinyl) group, 8-(β-carbolinyl) group, 9-(β-carbolinyl) group, 1-(γ-carbolinyl) group, 2-(γ-carbolinyl) group, 4-(γ-carbolinyl) group, 5-(γ-carbolinyl) group, 6-(γ-carbolinyl) group, 7-(γ-carbolinyl) group, 8-(γ-carbolinyl) group, 9-(γ-carbolinyl) group, 1-acridinyl group, 2-acridinyl group, 3-acridinyl group, 4-acridinyl group, 9-acridinyl group, 1-phenoxazinyl group, 2-phenoxazinyl group, 3-phenoxazinyl group, 4-phenoxazinyl group, 10-phenoxazinyl group, 1-phenothiazinyl group, 2-phenothiazinyl group, 3-phenothiazinyl group, 4-phenothiazinyl group, 10-phenothiazinyl group, 1-phenazinyl group, 2-phenazinyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 2-phenanthrolinyl group, 3-phenanthrolinyl group, 4-phenanthrolinyl group, 5-phenanthrolinyl group, 6-phenanthrolinyl group, 7-phenanthrolinyl group, 8-phenanthrolinyl group, 9-phenanthrolinyl group, 10-phenanthrolinyl group, 1-thianthrenyl group, 2-thianthrenyl group, 1-indolizinyl group, 2-indolizinyl group, 3-indolizinyl group, 5-indolizinyl group, 6-indolizinyl group, 7-indolizinyl group, 8-indolizinyl group, 1-phenoxathiinyl group, 2-phenoxathiinyl group, 3-phenoxathiinyl group, 4-phenoxathiinyl group, thieno[2,3-b]furyl group, pyrrolo[1,2-b]pyridazinyl group, pyrazolo

[1,5-a]pyridyl group, imidazo[11,2-a]pyridyl group, imidazo[1,5-a]pyridyl group, imidazo[1,2-b]pyridazinyl group, imidazo[1,2-a]pyrimidinyl group, 1,2,4-triazolo[4,3-a]pyridyl group, and 1,2,4-triazolo[4,3-a]pyridazinyl group, but are not limited to these examples.

Examples of the alkoxy group include, for example, methoxy group, ethoxy group, n-propoxy group, isopropoxy group, n-butoxy group, isobutoxy group, sec-butoxy group, tert-butoxy group, n-pentyloxy group, isopentyloxy group, 2-methylbutoxy group, 1-methylbutoxy group, neopentyloxy group, 1,2-dimethylpropoxy group, 1-ethylpropoxy group, n-hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 2-ethylbutoxy group, 1-ethylbutoxy group, 1-ethyl-1-methylpropoxy group, dn-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, cyclopropyloxy group, cyclobutyloxy group, cyclohexyloxy group, and the like, but are not limited to these examples. The term alkoxy group used in the specification encompasses, besides an alkyloxy group, an alkenyloxy group and an alkynyloxy group. As the alkenyl moiety of the alkenyloxy group and the alkynyl moiety of the alkynyloxy group, the alkenyl group and alkynyl group explained above can be used.

The aralkyl group means a group consisting of the aforementioned alkyl group on which one or two or more of the aforementioned aryl groups substitute, and when two or more aryl groups substitute, they may be the same or different. Examples include, for example, benzyl group, pyridylmethyl group, 1-naphthylmethyl group, 2-naphthylmethyl group, anthracenylmethyl group, phenanthrenylmethyl group, acenaphthylenylmethyl group, diphenylmethyl group, 1-phenethyl group, 2-phenethyl group, 1-(1-naphthyl)ethyl group, and the like, but are not limited to these examples.

Examples of the halogen atom include fluorine atom, chlorine atom, bromine atom, and iodine atom.

As the alkyl moiety, alkenyl moiety, alkynyl moiety, and aryl moiety of the alkylthio group, alkenylthio group, alkynylthio group, and arylthio group, the alkyl group, alkenyl group, alkynyl group, and aryl group explained above can be used.

The halogenated alkyl group means a group consisting of the aforementioned alkyl group on which one or two or more halogen atoms substitute, and when two or more halogen atoms substitute, they may be the same or different. Examples include, for example, fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, 2,2,2-trifluoroethyl group, pentafluoroethyl group, 3,3,3-trifluoropropyl group, heptafluoropropyl group, heptafluoroisopropyl group, nonafluorobutyl group, perfluorohexyl group, and the like, but are not limited to these examples.

When the expression "which may have a substituent" is used for a certain functional group in the specification, it means that one or more substituents may exist on the functional group at chemically substitutable positions. Type, number and substitution position of the substituent existing on the functional group are not particularly limited, and when two or more substituents exist, they may be the same or different. Examples of substituent existing on the functional groups include, for example, a halogen atom, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, mesoxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, a $C_1$-$C_6$ alkyl group, a $C_2$-$C_6$ alkenyl group (for example, vinyl group, allyl group, 1-propenyl group, and the like), a $C_2$-$C_6$ alkynyl group (for example, ethynyl group, 1-propynyl group, and the like), a $C_1$-$C_6$ alkylidene group, a $C_6$-$C_{10}$ aryl group, a $C_7$-$C_{12}$ aralkyl group (for example, benzyl group, phenethyl group, 1-naphthylmethyl group, 2-naphthylmethyl group, and the like), a $C_7$-$C_{12}$ aralkylidene group (for example, benzylidene group, phenethylidene group, 1-naphthylmethylidene group, 2-naphthylmethylidene group, and the like), a $C_1$-$C_6$ alkoxy group, a $C_6$-$C_{10}$ aryloxy group (for example, phenoxy group, 1-naphthyloxy group, 2-naphthyloxy group, and the like), a $C_7$-$C_{12}$ aralkyloxy group (for example, benzyloxy group, (1-naphthylmethyl)oxy group, (2-naphthylmethyl)oxy group, and the like), a $C_1$-$C_6$ alkylsulfanyl group (for example, methylsulfanyl group, ethylsulfanyl group, and the like), a $C_6$-$C_{10}$ arylsulfanyl group (for example, phenylsulfanyl group, 1-naphthylsulfanyl group, 2-naphthylsulfanyl group, and the like), a $C_7$-$C_{12}$ aralkyloxysulfanyl group (for example, benzylsulfanyl group, (1-naphthylmethyl)sulfanyl group, (2-naphthylmethyl)sulfanyl group, and the like), a $C_1$-$C_6$ alkanoyl group (for example, acetyl group, propionyl group, n-butyryl group, pivaloyl group, and the like), a $C_6$-$C_{10}$ aroyl group (for example, benzoyl group, 1-naphthoyl group, 2-naphthoyl group, and the like), a $C_1$-$C_6$ alkylsulfonyl group (for example, methanesulfonyl group, ethanesulfonyl group, propanesulfonyl group, and the like), a $C_6$-$C_{10}$ arylsulfonyl group (for example, benzenesulfonyl group, 1-naphthalenesulfonyl group, 2-naphthalenesulfonyl group, and the like), a $C_1$-$C_6$ alkoxycarbonyl group, amino group, hydrazino group, hydrazono group, diazenyl group, ureido group, thioureido group, guanidino group, carbamimidoyl group (amidino group), azido group, imino group, hydroxyamino group, hydroxyimino group, aminoxy group, diazo group, semicarbazino group, semicarbazono group, allophanyl group, hydantoyl group, phosphano group, phosphoroso group, phospho group, boryl group, silyl group, stanyl group, selanyl group, oxido groups, a heteroaryl group, a partially saturated or fully saturated heterocyclic group corresponding to a heteroaryl group all or a part of which double bonds are replaced with single bonds, and the like, but are not limited to these examples.

These substituents may be further substituted with one or two or more kinds of other substituents. Examples of such a substituent include, for example, a halogenated $C_1$-$C_6$ alkyl group (for example, chloromethyl group, dichloromethyl group, trichloromethyl group, difluoromethyl group, trifluoromethyl group, 2,2,2-trifluoroethyl group, pentafluoroethyl group, and the like), a halogenated $C_1$-$C_6$ alkoxy group (for example, trifluoromethoxy group, pentafluoroethoxy group, and the like), a carboxy-substituted $C_1$-$C_6$ alkyl group (for example, carboxymethyl group, carboxyethyl group, and the like), a $C_1$-$C_6$ alkyl-substituted amino group (for example, methylamino group, ethylamino group, and the like), and the like, but are not limited to these examples.

The first embodiment of the present invention is an embodiment in which the compound represented by the general formula (I) is used as a class of chiral auxiliary removable with an acid.

In the general formula (I), $R^1$ and $R^2$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $R^1$ and $R^2$ independently represent hydrogen atom or an alkyl group, and it is more preferred that both $R^1$ and $R^2$ are hydrogen atoms.

$R^3$ represents an aryl group which may have a substituent, or an alkyl group which may have a substituent. $R^3$ is preferably an aryl group, more preferably a phenyl group.

$R^4$ and $R^5$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $R^4$ and $R^5$ independently represent hydrogen atom or an alkyl group, and it is more preferred that both $R^4$ and $R^5$ are hydrogen atoms.

Y represents -$Y^1$-$Y^2$-, and $Y^1$ represents —C($R^6$)($R^7$)—, or an o-aryldiyl group which may have a substituent. $R^6$ and $R^7$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. $R^7$ may bind with the aryl group represented by $R^3$ to form a ring. It is preferred that $R^6$ and $R^7$ independently represent hydrogen atom or an alkyl group, and when $R^7$ represents an alkyl group, $R^7$ may bind to the aryl group represented by $R^3$, preferably phenyl group, to form a ring. Examples of the o-aryldiyl group represented by Y include, for example, o-phenylene group, naphthalene-1,2-diyl group, and the like, but are not limited to these examples. The aryl ring of the aryldiyl group may bind with the aryl group represented by $R^3$ to form a ring.

$Y^2$ represents a single bond or —C($R^8$)($R^9$)—. $R^8$ and $R^9$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $Y^2$ is a single bond, and in such a case, Y represents —C($R^6$)($R^7$)—, or an o-aryldiyl group which may have a substituent.

Preferred compounds of the general formula (I) are exemplified below, but the compounds are not limited to these examples.

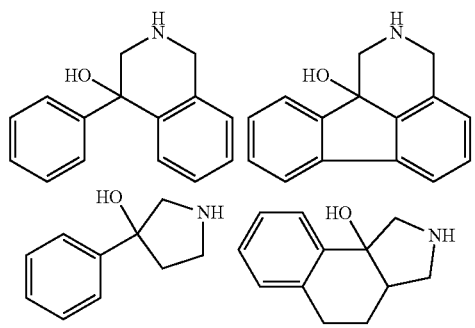

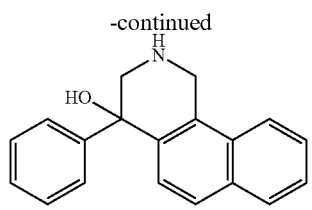

The following compounds can be mentioned as more preferred compounds, but the compounds are not limited to these examples.

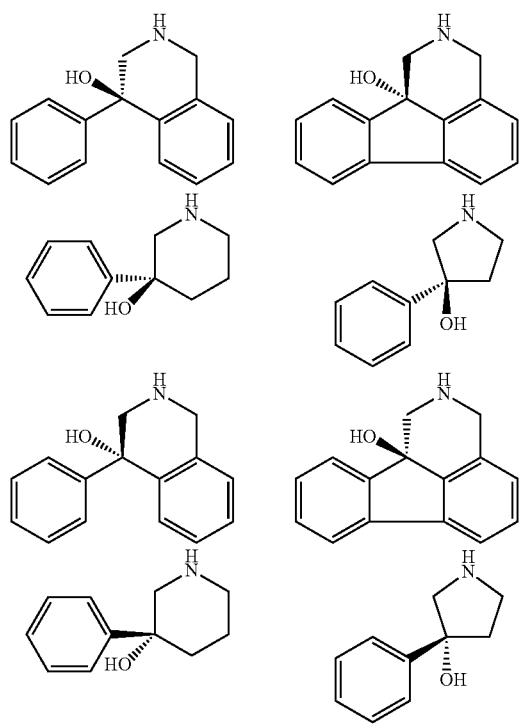

The compounds represented by the general formula (I) may form an acid addition salt, and arbitrary acid addition salts are encompassed by the scope of the present invention. For example, mineral acid salts such as hydrochloride, sulfate, and nitrate, and organic acid salts such as acetate, p-toluenesulfonate, methanesulfonate, maleate, and oxalate can be used, but the salt is not limited to these examples. Further, arbitrary stereoisomers in pure forms, arbitrary mixtures of stereoisomers, racemates, mixtures of diastereomers, and the like of the compounds represented by the general formula (I) are also encompassed by the scope of the present invention, but it is preferable to use a compound in an optically pure form. Furthermore, arbitrary hydrates or solvates of the compounds represented by the general formula (I) or a salt thereof are also encompassed by the scope of the present invention. The same shall apply to the nucleic acid derivatives represented by the general formula (II).

When the compounds represented by the aforementioned general formula (I) are used as a chiral auxiliary, a group represented by the aforementioned general formula (II) can be introduced on a phosphorus atom of a nucleic acid derivative as a chiral auxiliary. As for the general formula (II), examples of the nucleic acid derivative include, for example, phosphorothioate, boranophosphate, alkyl phosphonate, alkenyl phosphonate, alkynyl phosphonate, aryl phosphonate, phosphoroselenoate, phosphoroamidate, and the like, but are not limited to these examples.

As for method for synthesis of nucleic acid derivatives using a chiral auxiliary, methods for introducing a chiral auxiliary and methods for synthesizing a nucleic acid in the presence of a chiral auxiliary are explained in detail in International Patent Publication WO2010/064146, and therefore the present invention can be easily implemented by referring to this patent document. The entire disclosure of the aforementioned international patent publication is incorporated into the disclosure of this specification by reference.

Preferred examples of the nucleic acid derivative binding the chiral auxiliary represented by the general formula (II) include, for example, a nucleic acid derivative represented by the general formula (III). In the general formula (III), examples of the protective group of hydroxyl group include, for example, dimethoxytrityl group, acetyl group, benzoyl group, methoxybenzoyl group, trifluoroacetyl group, trimethylsilyl group, and the like, but are not limited to these examples. As for the protective group of hydroxyl group, publications such as Green et al., Protective Groups in Organic Synthesis, 3rd Edition, 1999, John Wiley & Sons, Inc. can be referred to.

As the nucleobase, a natural or non-natural nucleobase which may have a protective group can be used, and for example, a pyrimidine base such as cytosine, thymine, and uracil, or a purine base such as adenine and guanine can be used. As the base, there can also be used a modified base such as 5-methylcytosine, 5-hydroxymethylcytosine, 5-fluorouracil, 5-methyluracil, 2-thiouracil, 6-azauracil, 5-hydroxyuracil, 2,6-diaminopurine, 8-azaadenine, 8-azaguanine, and isoguanine, but are not limited to these examples.

In this specification, the linker means a generally linear divalent group present in the bond between the solid phase support and the nucleic acid derivative, and for example, a linear alkylene group which may have a substituent, as well as an alkylene group having a branched chain, a peptide linker, and the like can be used. For example, 3-aminopropyl group, succinyl group, 2,2'-diethanolsulfonyl group, a long chain alkylamino (LCAA) group, and the like can be used, but are not limited to these examples. Type of the solid phase support is also not particularly limited, and examples include, for example, controlled pore glass (CPG), oxalylated controlled pore glass (for example, Nucleic Acids Research, 19, 1527, 1991), TentaGel support/amino-polyethylene glycol derivatized support (Tetrahedron Letters, 34, 3373, 1993), a copolymer of Poros-polystyrene/divinylbenzene, and the like, but are not limited to these examples.

The method for preparing a nucleic acid derivative of the present invention using the aforementioned chiral auxiliary typically comprises the following steps: (a) the step of reacting a nucleic acid derivative represented by the general formula (V) and a nucleotide derivative represented by the general formula (IV) to prepare a nucleic acid derivative represented by the general formula (III); (b) the step of repeating the step of removing the protective group(s) of hydroxyl group represented by $R^{11}$ from the nucleic acid derivative represented by the general formula (III) obtained by the above step (a), and reacting the obtained nucleic acid derivative and a nucleotide derivative represented by the general formula (IV) as required; (c) the step of removing the chiral auxiliary represented by the general formula (II) under an acidic condition to prepare a nucleic acid derivative represented by the general formula (VI); and (d) the step of introducing X into the phosphorus atom of the nucleic acid derivative obtained in the above step (c), and then removing the protective group(s) as required.

This method can be performed in the same manner as that of the cycle shown as Route B in the scheme mentioned for explaining the reaction process of International Patent Publication WO2010/064146 in the background art section.

The compound of the general formula (IV) used in the aforementioned method can be prepared by, for example, activating an achiral mononucleotide monomer as required, and then reacting the resultant with a compound represented by the general formula (I) according to the method disclosed in International Patent Publication WO2010/064146. The compound represented by the general formula (IV) is a tricyclic active intermediate, and has higher reactivity compared with a reaction intermediate prepared from the compound represented by Formula Q or Formula R disclosed in International Patent Publication WO2010/064146.

In the aforementioned method, as the acidic condition for removing the chiral auxiliary represented by the general formula (II) in the step (b), for example, 3% dichloroacetic acid (DCA) in dichloromethane can be used. This acidic condition is a milder acidic condition compared with the condition for removing a chiral auxiliary introduced by using the compound represented by Formula Q or Formula R disclosed in International Patent Publication WO2010/064146 (1% trifluoroacetic acid (TFA) in dichloromethane), and does not cause elimination of the adenine base of which base moiety is protected with an acyl type protective group.

Although it is not intended to be bound by any specific theory, it is estimated that the reaction mechanism according to which the chiral auxiliary represented by the general formula (II) is eliminated under an acidic condition is the following $S_N1$ (E1 reaction) mechanism. In the following reaction scheme, one preferred embodiment of the chiral auxiliary represented by the general formula (II) is shown.

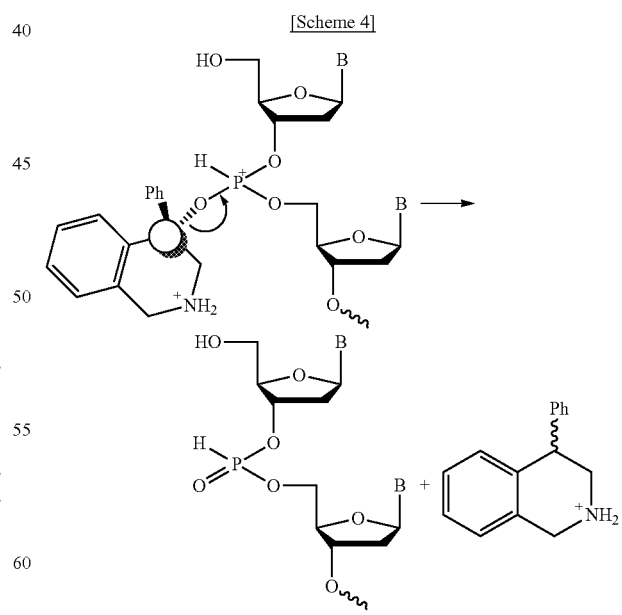

[Scheme 4]

The second embodiment of the present invention is an embodiment in which a compound represented by the general formula (XI) is used as a class of chiral auxiliary to be removed with a base.

In the general formula (XI), $R^{101}$ and $R^{102}$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $R^{101}$ and $R^{102}$ are hydrogen atom or an alkyl group, and it is more preferred that both $R^{101}$ and $R^{102}$ are hydrogen atoms.

$R^{103}$ represents cyano group, a halogen atom, a halogenated alkyl group which may have a substituent, a halogenated alkanoyl group which may have a substituent, sulfonyl group, a halogenated alkylsulfonyl group which may have a substituent, or nitro group. $R^{103}$ is preferably cyano group.

Z represents $-Z^1-Z^2-$, and $Z^1$ represents $-C(R^{104})(R^{105})-$. $R^{104}$ and $R^{105}$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $R^{104}$ and $R^{105}$ are hydrogen atom or an alkyl group, and it is more preferred that both $R^{104}$ and $R^{105}$ are hydrogen atoms.

$Z^2$ represents a single bond or $-C(R^{106})(R^{107})-$. $R^{106}$ and $R^{107}$ independently represent hydrogen atom, an alkyl group which may have a substituent, an alkenyl group which may have a substituent, an alkynyl group which may have a substituent, an alkoxy group which may have a substituent, an aralkyl group which may have a substituent, or an aryl group which may have a substituent. It is preferred that $Z^2$ is a single bond or $-C(R^{106})(R^{107})-$ ($R^{106}$ and $R^{107}$ represent hydrogen atom), and it is more preferred that $Z^2$ is a single bond.

A compound of the general formula (XI) wherein $R^{101}$ and $R^{102}$ are hydrogen atom or an alkyl group, $R^{103}$ is cyano group, and Z is $-C(R^{104})(R^{105})-$ or $-C(R^{104})(R^{105})-CH_2-$ ($R^{104}$ and $R^{105}$ are hydrogen atom or an alkyl group) is preferred, and a compound of the general formula (XI) wherein $R^{101}$ and $R^{102}$ are hydrogen atoms, $R^{103}$ is cyano group, and Z is $-C(R^{104})(R^{105})-$ ($R^{104}$ and $R^{105}$ are hydrogen atoms) is more preferred.

Although the following compounds can be mentioned as more preferred compounds, the compound is not limited to these examples.

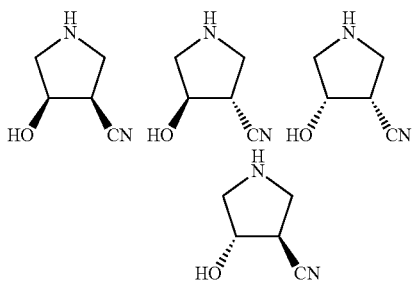

The compounds represented by the general formula (XI) may form an acid addition salt, and arbitrary acid addition salts are encompassed by the scope of the present invention. For example, mineral acid salts such as hydrochloride, sulfate, and nitrate, and organic acid salts such as acetate, p-toluenesulfonate, methanesulfonate, maleate, and oxalate can be used, but the salt is not limited to these examples. Further, arbitrary stereoisomers in pure forms, arbitrary mixtures of stereoisomers, racemates, mixtures of diastereomers, and the like of the compounds represented by the general formula (XI) are also encompassed by the scope of the present invention, but it is preferable to use a compound in an optically pure form. Furthermore, arbitrary hydrates or solvates of the compounds represented by the general formula (XI) or a salt thereof are also encompassed by the scope of the present invention. The same shall apply to the nucleic acid derivatives represented by the general formula (XII).

When the compounds represented by the aforementioned general formula (XI) are used as a chiral auxiliary, a group represented by the aforementioned general formula (XII) can be introduced on a phosphorus atom of a nucleic acid derivative as a chiral auxiliary. As for the general formula (XII), examples of the nucleic acid derivative include, for example, phosphorothioate, boranophosphate, phosphoroselenoate, and the like, but are not limited to these examples.

When the compounds represented by the aforementioned general formula (XI) are used as a chiral auxiliary, a group represented by the aforementioned general formula (XII) can be introduced on a phosphorus atom of a nucleic acid derivative as a chiral auxiliary. As for the general formula (XII), examples of the nucleic acid derivative include, for example, phosphorothioate, boranophosphate, phosphoroselenoate, and the like, but are not limited to these examples.

Preferred examples of the nucleic acid derivative to which the chiral auxiliary represented by the general formula (XII) binds include, for example, a nucleic acid derivative represented by the general formula (XIII). The protective group of hydroxyl group, nucleobase, linker, and solid phase support may be the same as those explained for the aforementioned general formula (III).

The method for preparing a nucleic acid derivative of the present invention using the aforementioned chiral auxiliary typically comprises the following steps: (a) the step of reacting a nucleic acid derivative represented by the general formula (XIII') and a nucleotide derivative represented by the general formula (XIV) ($R^{121}$ represents a protective group of hydroxyl group; and $R^{122}$ represents hydrogen atom, an alkoxy group, fluorine atom, or a protected hydroxyl group), then introducing X using an electrophilic agent, removing the protective group(s) of hydroxyl group represented by $R^{121}$ to prepare a nucleic acid derivative represented by the general formula (XV), and repeating the above reaction as required to prepare a nucleic acid derivative represented by the general formula (XV); and (b) the step of removing the chiral auxiliary represented by the general formula (XII) from the nucleic acid derivative represented by the general formula (XV) obtained by the above step (a) under a basic condition to prepare a nucleic acid derivative represented by the general formula (XVII).

This method can be performed in the same manner as that of the cycle shown as Route A in the scheme mentioned for explaining the reaction process of International Patent Publication WO2010/064146 in the background art section.

The compound of the general formula (XIV) used in the aforementioned method can be prepared by, for example, activating an achiral mononucleotide monomer as required, and then reacting the resultant with a compound represented by general formula (XI) according to the method disclosed in International Patent Publication WO2010/064146. The compound represented by the general formula (XIV) is a tricyclic active intermediate, and has higher reactivity compared with a reaction intermediate prepared from the compound represented by Formula O or Formula P disclosed in International Patent Publication WO2010/064146.

In the aforementioned method, examples of the basic condition for removing the chiral auxiliary represented by the general formula (II) in the step (b) include, for example, 10% DBU in acetonitrile (room temperature, 15 minutes), 10% piperidine in acetonitrile (room temperature, 15 minutes), aqueous ammonia (room temperature, 12 hours), and the like. This basic condition is a milder basic condition compared with the basic condition for removing a chiral auxiliary introduced by using the compound represented by Formula O or Formula P disclosed in International Patent Publication WO2010/064146 (condition of performing a treatment with aqueous ammonia at 55° C. for 12 hours to remove it as an aziridine compound). The chiral auxiliary represented by the general formula (II) has a characteristic that it can be removed under such a mild condition according to the B elimination mechanism shown below, and therefore it enables extremely efficient production of a long chain nucleic acid derivative.

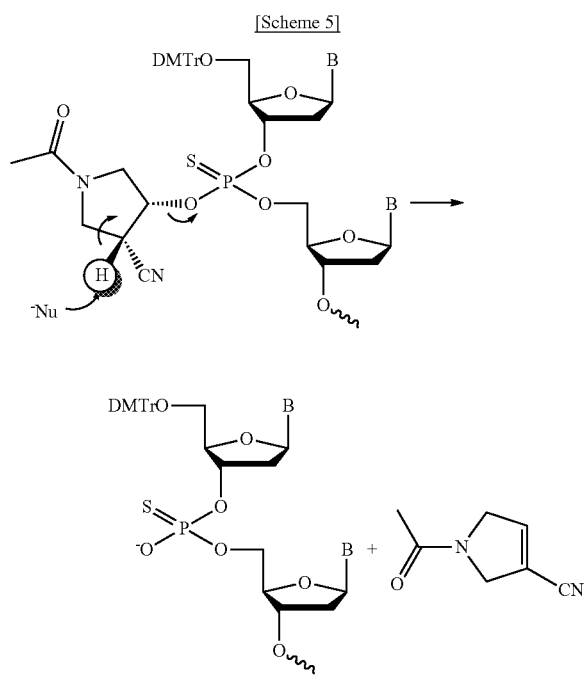

[Scheme 5]

EXAMPLES

Hereafter, the present invention will be more specifically explained with reference to examples. However, the scope of the present invention is not limited by the following examples.

Example 1

(a) 3-Cyano-3-phenylisobenzofuran-1(3H)-one (1)

A mixture of diethylaluminum chloride ($Et_2AlCl$, 34.5 mL of 0.87 M solution in hexane, 30 mmol) and trimethylsilyl cyanide (3.7 mL, 30 mmol) was stirred at room temperature for 30 min, and the mixture was added via cannular at 0° C. to a solution of methyl 2-benzoylbenzoate (6 g, 30 mmol), which was dried by azeotropy with dry toluene, in dichloromethane (DCM, 12.5 mL). After the mixture had been stirred for 1 hr, the reaction was quenched with ice-cooled 3 M aqueous sodium hydroxide (250 mL), and the mixture was extracted with dichloromethane (200 mL, 3 times). The organic layer was washed with saturated brine (300 mL), and back-extracted with dichloromethane (200 mL, twice). The organic layer and washings were combined, dried over sodium sulfate, and concentrated. The residue was chromatographed on silica gel (150 g) eluted with ethyl acetate-n-hexane (1:4) to give Compound 1 (5.68 g, 97%) as white solid.
$^1$H NMR (300 MHz, $CDCl_3$) δ 8.01 (1H, d, J=7.8 Hz), 7.81 (1H, t, J=7.2 Hz), 7.71 (1H, t, J=7.2 Hz), 7.56 (1H, d, J=7.8 Hz), 7.52-7.40 (5H, m); $^{13}$C NMR (75.5 MHz, $CDCl_3$) δ 167.3, 146.6, 135.8, 133.6, 131.4, 130.7, 129.3, 126.3, 125.7, 123.9, 123.2, 115.8, 79.6

(b) 4-Phenyl-1,2,3,4-tetrahydroisoquinolin-4-ol (2)

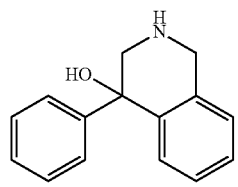

Compound 1 (2 g, 8.5 mmol) was dried by azeotropy with dry toluene, and dissolved in dry diethyl ether (35 mL), which was added via cannular to a solution of lithium aluminum hydride in dry diethyl ether (40 mL) at −78° C., and stirred for 1.5 hr. The reaction mixture was warmed to room temperature, stirred for 12 hr, and quenched with 10% sodium hydroxide (20 mL), and stirring was continued for 10 min. The residue was diluted with water (20 mL +60 mL), filtered through a celite pad. The filtrate was extracted with chloroform (100 mL, 3 times), and combined organic layer was washed with brine (200 mL). The organic layer and washings were combined, dried over sodium sulfate, filtered, and concentrated to dryness under reduced pressure. The residue was chromatographed on silica gel (150 g) using a gradient of methanol (0-4%) in dichloromethane containing 1% triethylamine as an eluent. The fractions containing Compound 2 were combined and concentrated to dryness under reduced pressure to give Compound 2 (1.89 g, 99%) as a white solid.

$^1$H NMR (300 MHz, CDCl$_3$) δ 7.22-7.18 (9H, m), 4.42 (1H, d, J=11.7 Hz), 4.09 (1H, d, J=11.7 Hz), 3.53 (1H, d, J=12.0 Hz), 3.23 (1H, d, J=12.0 Hz), 1.64 (2H, brs); $^{13}$C NMR (75.5 MHz, CDCl$_3$) δ 145.4, 143.1, 140.8, 133.0, 128.2, 128.1, 127.5, 127.0, 125.7, 125.6, 77.3, 64.4, 51.7; ESI TOF-MS m/z Calcd for C$_{15}$H$_{16}$NO [M+H]+ 226.12, found 226.15

(c) N-Boc-3-Phenylpiperidin-3-ol (3)

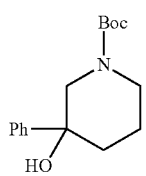

N-Boc-3-Pipelidone (1 g, 5 mmol) was dried by azeotropy with dry toluene, and dissolved in dry tetrahydrofuran (THF, 10 ml). 1.08 M Phenyl magnesium bromide in tetrahydrofuran (6.9 ml, 7.5 mmol) was carefully added to the solution at −30° C., and the mixture was stirred for 30 min at −30° C. The reaction mixture was then gradually warmed to room temperature, and stirring was continued for 12 h. A mixture of concentrated aqueous ammonia and saturated aqueous ammonium chloride (30 ml, 1:2, v/v) was added to the reaction mixture at 0° C., and extracted with dichloromethane (15 mL, 3 times) and the combined organic layers were dried over sodium sulfate, filtered, and concentrated under reduced pressure. The residue was chromatographed on silica gel (90 g) using a gradient of methanol (0-2%) in dichloromethane to give Compound 3 (469 mg, 34%) as light yellow oil.

$^1$H NMR (300 MHz, CD$_3$OD) δ 7.53 (2H, d, J=6.9 Hz), 7.34 (2H, t, J=6.9 Hz), 7.25 (1H, d, J=6.9 Hz), 4.20-3.88 (1H, m), 3.88-3.71 (1H, m), 3.42-3.18 (1H, m), 3.08-2.93 (1H, m), 2.13-1.77 (3H, m), 1.58-1.47 (1H, m), 1.46 (9H, s); $^{13}$C NMR (75.5 MHz, CD$_3$OD) δ 157.2, 147.5, 129.2, 128.1, 126.3, 81.0, 79.5, 72.4, 37.8, 28.7, 22.3

(d) 3-Phenylpiperidin-3-ol (4)

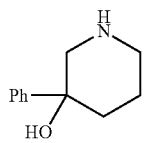

Compound 3 (469 mg, 1.7 mmol) and p-toluenesulfonic acid monohydrate (675 mg, 3.5 mmol) were dissolved in dichloromethane (8.5 mL) and stirred for 2 h at room temperature. 3 N Potassium hydroxide (10 mL) was added to the reaction mixture, and extracted with dichloromethane (10 mL, 4 times). The combined organic layers were washed with saturated brine (50 mL), and the aqueous layer was back extracted with dichloromethane (30 mL, 4 times). The combined organic layers were dried over sodium sulfate, filtered and concentrated under reduced pressure to afford Compound 4 (291 mg, 97%) as pale yellow solid.

$^1$H NMR (300 MHz, CD$_3$OD) δ 7.53-7.46 (2H, m), 7.37-7.29 (2H, m), 7.26-7.18 (1H, m), 3.08-2.99 (1H, m), 2.93-2.85 (1H, m), 2.81-2.72 (1H, m), 2.68-2.56 (1H, m), 2.13-1.80 (3H, m), 1.61-1.51 (1H, m); $^{13}$C NMR (75.5 MHz, CD$_3$OD) δ 148.7, 129.2, 127.9, 125.8, 71.8, 57.4, 46.3, 37.2, 23.4; ESI TOF-MS m/z Calcd for C$_{11}$H$_{16}$NO [M+H]+ 178.12, found 178.14

(e) N-Boc-3-Phenylpyrrolidin-3-ol (5)

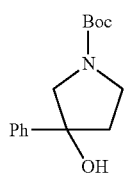

Compound 5 was obtained as brown solid (41% yield) using N-Boc-3-pyrrolidone instead of N-Boc-3-pipelidone in a similar manner to that used for Compound 3.

$^1$H NMR (300 MHz, CDCl$_3$) δ 7.52-7.28 (5H, m), 3.80-3.54 (4H, m), 2.42-2.10 (2H, m), 1.93 (1H, brs), 1.48 (9H, s)

(f) 3-Phenylpyrrolidin-3-ol (6)

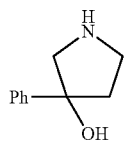

Compound 6 was obtained as brown solid (84% yield) using Compound 5 instead of Compound 3 in a similar manner to that used for Compound 4.

$^1$H NMR (300 MHz, CDCl$_3$) δ 7.52-7.46 (2H, m), 7.41-7.24 (3H, m), 3.34 (1H, dt, J=10.8, 7.8 Hz), 3.20-3.09 (2H, m), 3.03 (1H, d, J=12.0 Hz), 2.27 (1H, ddd, J=13.4, 9.3, 7.5 Hz), 2.18-2.06 (1H, m), 1.95 (1H, brs); $^{13}$C NMR (75.5 MHz, CD$_3$OD) δ 146.0, 129.2, 128.0, 126.4, 83.1, 61.9, 46.8, 42.9; ESI TOF-MS m/z Calcd for C$_{10}$H$_{14}$NO [M+H]+ 164.11, found 164.13

(g) (±)-trans-N-Boc-4-Cyanopyrrolidin-3-ol (7)

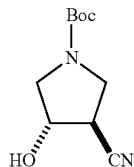

A mixture of diethylaluminum chloride (16.2 mL of 0.87 M solution in hexane, 14 mmol) and trimethylsilyl cyanide (1.8 mL, 14 mmol) was stirred at room temperature for 30 min, and the mixture was added via cannular at 0° C. to N-Boc-(1R,5S)-6-oxa-3-azabicyclo[3.1.0]hexane (2.2 g, 12 mmol), which was dried by azeotropy with dry toluene. After the mixture had been stirred for 1.5 h, the reaction was quenched with ice-cooled 3 M aqueous sodium hydroxide (100 mL), and the mixture was extracted with dichloromethane (50 mL, 4 times). The organic layer was washed with saturated brine (300 mL), and back-extracted with dichloromethane (200 mL, 2 times). The organic layers were combined, dried over sodium sulfate, and concentrated. The residue was chromatographed on silica gel (150 g) eluted with ethyl acetate-n-hexane (1:4) to give Compound 7 (1.38 g, 55%, 2 steps) as light yellow oil.
$^1$H NMR (300 MHz, CDCl$_3$) δ 4.64 (1H, q, J=4.5 Hz), 3.87-3.62 (3H, m), 3.47-3.31 (1H, m), 3.15-2.99 (1H, m), 2.46 (1H, brs), 1.47 (9H, s); ESI TOF-MS m/z Calcd for C$_{10}$H$_{14}$NO [M+H]+ 164.11, found 164.13

(h) (±)-trans-4-Cyanopyrrolidin-3-ol (8)

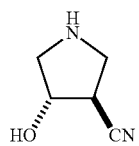

8

Compound 7 (21.2 mg, 100 μmnol) was dissolved in dichloromethane (1 mL). Cleaned Amberlyst 15 Resin (150 mg) was added, and the reaction mixture was gently shaken for 2 h. The resin was then separated by filtration, and washed with hexane, tetrahydrofuran, and ethanol successively. The resin was transferred to 2 M ammonia in ethanol (1 mL), and gently shaken for 1 h. The resin was then removed by filtration, and washed with methanol, and the filtrate was evaporated under reduced pressure to afford Compound 8 (10.2 mg, 91%) as light yellow solid.
$^1$H NMR (300 MHz, CD$_3$OD) δ 4.49 (1H, dt, J=6.0, 3.6 Hz), 3.39 (1H, dd, J=11.9, 8.1 Hz), 3.08 (1H, dd, 12.3, 5.4 Hz), 3.00 (1H, dd, J=11.9, 5.7 Hz), 2.92-2.85 (1H, m), 2.80 (1H, dd, J=12.3, 3.6 Hz); $^{13}$C NMR (100 MHz, CD$_3$OD) δ 121.7, 77.5, 55.5, 50.8, 39.1; ESI TOF-MS m/z Calcd for C$_5$H$_9$N$_2$O [M+H]+ 113.07, found 113.07

(i) (R)-4-Phenyl-1,2,3,4-tetrahydroisoquinolin-4-ol (2a) and (S)-4-phenyl-1,2,3,4-tetrahydroisoquinolin-4-ol (2b)

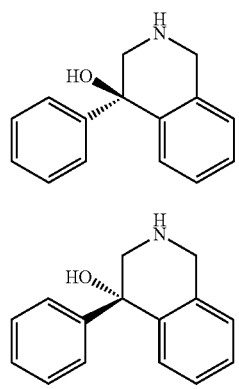

Resolving Compound 2 by chiral column chromatography gives Compounds 2a and 2b.

(j) (S)-3-Phenylpiperidin-3-ol (4a) and (R)-3-Phenylpiperidin-3-ol (4b)

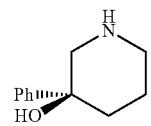

4a

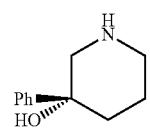

4b

Resolving Compound 4 by chiral column chromatography gives Compounds 4a and 4b.

(k) (S)-3-Phenylpyrrolidin-3-ol (6a) and (R)-3-phenylpyrrolidin-3-ol (6b)

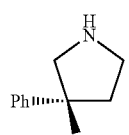

6a

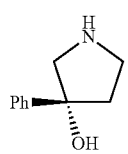

6b

Resolving Compound 6 by chiral column chromatography gives Compounds 6a and 6b.

(l) (3R,4R)-4-Cyanopyrrolidin-3-ol (8a) and (3S,4S)-4-cyanopyrrolidin-3-ol (8b)

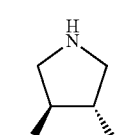

8a

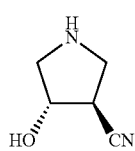

8b

Resolving Compound 8 by chiral column chromatography gives Compounds 8a and 8b.

(m) (±)-trans-4-Cyanopiperidin-3-ol (12)

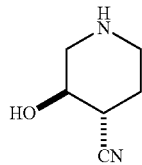

Compound 12 was synthesized from 1-benzylpiperidin-4-one according to the literature (Tetrahedron, 2008, 64, 2456-2464).

(n) (3R,4R)-4-Cyanopiperidin-3-ol (12a) and (3S,4S)-4-Cyanopiperidin-3-ol (12b)

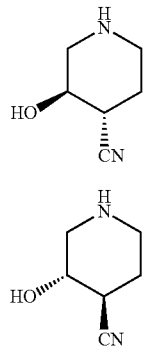

Resolving Compound 12 by chiral column chromatography gives Compound 12a and 12b.

Example 2

(a) General Procedure for the Solid-Phase Synthesis of X-phosphonate DNAs Using a Class of Chiral Auxiliary Removable with Acid (General Formula I)

5'-O-(DMTr)nucleoside (0.5 µmol) loaded to a HCP or CPG resin via a succinyl or oxalyl linker is treated with 3% dichloroacetic acid (DCA) in dichloromethane for the removal of the 5'-O-DMTr group, washed with dichloromethane and dried in vacuo. Chain elongation is performed by repeating the following steps (a) and (b). (a) Coupling reaction (5 min) using a solution containing the corresponding pre-activated monomer solution under argon. After the condensation, the solid support is washed with dry acetonitrile (MeCN) and dichloromethane. (b) Removal of the 5'-O-DMTr group and the chiral auxiliary simultaneously by treatment with 3% dichloroacetic acid in dichloromethane and triethylsilane (1:1, v/v), and following washings with dichloromethane and dry acetonitrile. After the chain elongation, the resultant oligonucleoside H-phosphonates on the resin are converted to X-phosphonate DNAs as described below.

A pre-activated ($R_P$)- or ($S_P$)-monomer solution is prepared as follows. 8-Diazabicyclo[5.4.0]undec-7-enium 5'-O-(DMTr)-2'-deoxynucleosid-3'-yl phosphonate (25 µmol) is dried by azeotropy with dry toluene, and then dissolved in dry acetonitrile —N-cyanomethylpyrrolidine (9:1, v/v). To the solution, triphenylphosphine dichloride (62.5 µmol) is added, and stirred for 10 min. Compound 2a, 4a, or 6a (30 µmol; Compound 2b, 4b, or 6b for "$S_P$" solution) is then added and stirred for additional 10 min to give a pre-activated monomer solution.

(b) Phosphorothioate (X=S—)

Oligonucleoside H-phosphonate loaded to a HCP or CPG resin via a succinyl linker obtained as above is treated with 10 wt % $S_8$ in carbon disulfide-pyridine-triethylamine (35:35:1, v/v/v) at room temperature for 3 h, and successively washed with carbon disulfide, pyridine, and acetonitrile. The resin is treated with 25% aqueous ammonia at room temperature over 12 h, and washed with water. The aqueous solutions are combined and concentrated to dryness under reduced pressure, and the residue is purified by reverse phase HPLC to afford stereoregulated phosphorothioate DNAs.

(c) Boranophosphate (X=BH$_3$—)

Dry dimethylformamide, N,O-bis(trimethylsilyl)acetamide (BSA), and borane dimethyl sulfide (BH$_3$—SMe$_2$) are added to the oligonucleside H-phosphonate loaded to a HCP or CPG resin via a oxalyl linker obtained as above at room temperature. After 15 min, the resin is successively washed with dimethylformamide, acetonitrile, and methanol. The resin is then treated with a saturated ammonia solution in methanol at room temperature for 12 h, and washed with methanol. The methanol solutions are combined and concentrated to dryness under reduced pressure, and the residue is purified by reverse phase HPLC to afford stereoregulated boranophosphate DNAs.

(d) Hydroxymethylphosphonate (X=CH$_2$OH)

Oligonucleoside H-phosphonate loaded to a HCP or CPG resin via a oxalyl linker obtained as above is treated with 0.1 M trimethylsilyl chloride (TMSCl) in pyridine-1-methyl-2-pyrrolidone (NMP) (1:9, v/v) at room temperature for 10 min, and with gaseous formaldehyde at room temperature for 30 min, and then washed with 1-methyl-2-pyrrolidone, and acetonitrile. The resin is then treated with 25% aqueous ammonia at room temperature for 12 h, and washed with water. The combined aqueous solutions are concentrated to dryness under reduced pressure, and the residue is purified by reverse phase HPLC to afford stereoregulated hydroxymethylphosphonate DNAs.

(e) Phosphoramidate (X=NH$_2$)

Oligonucleoside H-phosphonate loaded to a HCP or CPG resin via an oxalyl linker obtained as above is treated with a saturated ammonia solution in carbon tetrachloride-1,4-dioxane (4:1, v/v) at 0° C. for 30 min, and washed with 1,4-dioxane. The combined organic solutions are concentrated to dryness under reduced pressure, treated with 25% aqueous ammonia at room temperature for 12 h, and washed with water. The combined aqueous solutions are concentrated to dryness under reduced pressure, and the residue is purified by reverse phase HPLC to afford stereoregulated phosphoramidate DNAs.

(f) N-Propylphosphoramidate (X=NHPr)

Oligonucleoside H-phosphonate loaded to a HCP or CPG resin via an oxalyl linker obtained as above is treated with carbon tetrachloride-propylamine (9:1, v/v) at room temperature for 1 h, and washed with methanol. The combined organic solutions are concentrated to dryness under reduced pressure, treated with 25% aqueous ammonia at room temperature for 12 h, and washed with water. The combined aqueous solutions are concentrated to dryness under reduced pressure, and the residue is purified by reverse phase HPLC to afford stereoregulated N-propylphophoramidate DNAs.

(f) N-[(2-Dimethylamino)ethyl]phosphoramidate [X=NH(CH$_2$)$_2$NMe$_2$]

Oligonucleoside H-phosphonate loaded to a HCP or CPG resin via an oxalyl linker obtained as above is treated with carbon tetrachloride-2-dimethylaminoethylamine (9:1, v/v) at room temperature for 1 h, and washed with acetonitrile. The combined organic solutions are concentrated to dryness under reduced pressure, treated with 25% aqueous ammonia at room temperature for 12 h, and washed with water. The combined aqueous solutions are concentrated to dryness under reduced pressure, and the residue is purified by reverse phase HPLC to afford stereoregulated N-[(2-dimethylamino)ethyl]phosphoramidate DNAs.

Example 3

(a) General Procedure for the Solid-Phase Synthesis of X-phosphonate RNAs Using a Class of Chiral Auxiliary Removable with Acid (General Formula I)

5'-O-(DMTr)ribonucleoside (0.5 μmol) loaded to a HCP or CPG resin via a succinyl or oxalyl linker is treated with 3% dichloroacetic acid in dichloromethane for the removal of the 5'-O-DMTr group, washed with dichloromethane and dried in vacuo. Chain elongation is performed by repeating the following steps (a) and (b). (a) Coupling reaction (15 min) using a solution containing the corresponding pre-activated monomer solution under argon. After the condensation, the solid support is washed with dry acetonitrile and dichloromethane. (b) Removal of the 5'-O-DMTr group and the chiral auxiliary simultaneously by treatment with 3% dichloroacetic acid in dichloromethane-triethylsilane (1:1, v/v), and following washings with dichloromethane and dry acetonitrile. After the chain elongation, the resultant oligonucleoside H-phosphonates on the resin are converted to X-phosphonate RNAs as described below.

A pre-activated (R$_P$)- or (S$_P$)-monomer solution is prepared as follows. 8-Diazabicyclo[5.4.0]undec-7-enium 5'-(DMTr)-2'-O-(TBS)ribonucleosid-3'-yl phosphonate (25 μmol) is dried by azeotropy with dry toluene, and then dissolved in dry acetonitrile-N-cyanomethylpyrrolidine (9:1, v/v). To the solution, triphenylphosphine dichloride (62.5 μmol) is added, and stirred for 10 min. Compound 2a, 4a, or 6a (30 μmol; Compound 2b, 4b, or 6b for "S$_P$" solution) is then added and stirred for additional 10 min to give a pre-activated monomer solution.

(b) Phosphorothioate (X=S—)

Oligonucleoside H-phosphonate loaded to a HCP or CPG resin via a succinyl linker obtained as above is treated with 10 wt % S$_8$ in carbon disulfide-pyridine-triethylamine (35:35:1, v/v/v) at room temperature for 3 h, and successively washed with carbon disulfide, pyridine, and ethanol. The resin is then treated with 25% aqueous ammonia-ethanol (3:1, v/v) for 2 h at room temperature and removed by filtration. The filtrate is diluted with 25% ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected phosphorothioate RNAs are collected and lyophilized. The residue is treated with a 1 M tetrabutylammonium fluoride solution in dry tetrahydrofuran for 24 h at room temperature. A 0.05 M triethylammonium acetate buffer solution (pH 6.9) is added, and tetrahydrofuran is removed by evaporation. The residue is desalted with a Sep-Pak PLUS tC$_{18}$ cartridge, and purified by reverse phase HPLC to afford stereoregulated phosphorothioate RNAs.

(c) Boranophosphate (X=BH3—)

Dry dimethylformamide, N,O-bis(trimethylsilyl)acetamide (BSA), and borane dimethyl sulfide are added to the oligonucleoside H-phosphonate loaded to a HCP or CPG resin via an oxalyl linker obtained as above at room temperature. After 15 min, the resin is successively washed with dimethylformamide, acetonitrile, and ethanol. The resin is then treated with 25% aqueous ammonia-ethanol (3:1, v/v) for 2 h at room temperature and removed by filtration. The filtrate is diluted with a 25% aqueous ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected boranophosphate RNAs are collected and lyophilized. The residue is treated with a 1 M tetrabutylammonium fluoride solution in dry tetrahydrofuran for 24 h at room temperature. A 0.05 M triethylammonium acetate buffer solution (pH 6.9) is added, and tetrahydrofuran is removed by evaporation. The residue is desalted with a Sep-Pak PLUS tC$_{18}$ cartridge, and purified by reverse phase HPLC to afford stereoregulated boranophosphate RNAs.

(d) Hydroxymethylphosphonate (X=CH$_2$OH)

Oligonucleoside H-phosphonate loaded to a HCP or CPG resin via an oxalyl linker obtained as above is treated with 0.1 M trimethylsilylchloride (TMSCl) in pyridine-1-methyl-2-pyrrolidone (NMP) (1:9, v/v) at room temperature for 10 min, and with gaseous formaldehyde at room temperature for 30 min, and then washed with 1-methyl-2-pyrrolidone, and ethanol. The resin is then treated with 25% aqueous ammonia-ethanol (3:1, v/v) for 2 h at room temperature and removed by filtration. The filtrate is diluted with 25% aqueous ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected hydroxymethylphosphonate RNAs are collected and lyophilized. The residue is treated with a 1 M tetrabutylammonium fluoride solution in dry tetrahydrofuran for 24 h. A 0.05 M triethylammonium acetate buffer solution (pH 6.9) is added, and tetrahydrofuran is removed by evaporation. The residue is desalted with a Sep-Pak PLUS tC$_{18}$ cartridge, and purified by reverse phase HPLC to afford stereoregulated hydroxymethylphosphonate RNAs.

(e) Phosphoramidate (X=NH$_2$)

Oligonucleoside H-phosphonate loaded to a HCP or CPG resin via an oxalyl linker obtained as above is treated with a saturated ammonia solution in carbon tetrachloride-1,4-dioxane (4:1, v/v) at 0° C. for 30 min, and washed with 1,4-dioxane. The combined organic solutions are concentrated to dryness under reduced pressure. The filtrate is diluted with 25% aqueous ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected phosphoramidate RNAs are collected and lyophilized. The residue is treated with a 1 M tetrabutylammonium fluoride solution in dry tetrahydrofuran for 24 h. A 0.05 M triethylammonium acetate buffer solution (pH 6.9) is added, and tetrahydrofuran is removed by evaporation. The residue is desalted with a Sep-Pak PLUS $tC_{18}$ cartridge, and purified by reverse phase HPLC to afford stereoregulated phosphoramidate RNAs.

(f) N-propylphosphoramidate (X=NHPr)

Oligonucleoside H-phosphonate loaded to a HCP or CPG resin via an oxalyl linker obtained as above is treated with carbon tetrachloride-propylamine (9:1, v/v) at room temperature for 1 h, and washed with methanol. The combined organic solutions are concentrated to dryness under reduced pressure. The filtrate is diluted with 25% aqueous ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected N-propylphophoramidate RNAs are collected and lyophilized. The residue is treated with a 1 M tetrabutylammonium fluoride solution in dry tetrahydrofuran for 24 h. A 0.05 M triethylammonium acetate buffer solution (pH 6.9) is added, and tetrahydrofuran is removed by evaporation. The residue is desalted with a Sep-Pak PLUS $tC_{18}$ cartridge, and purified by reverse phase HPLC to afford stereoregulated Npropylphophoramidate RNAs.

(g) N-[(2-dimethylamino)ethyl]phosphoramidate [X=NH(CH$_2$)$_2$NMe$_2$]

Oligonucleoside H-phosphonate loaded to a HCP or CPG resin via an oxalyl linker obtained as above is treated with carbon tetrachloride-2-dimethylaminoethylamine (9:1, v/v) at room temperature for 1 h, and washed with acetonitrile. The combined organic solutions are concentrated to dryness under reduced pressure. The result is diluted with 25% aqueous ammonia-ethanol (3:1, v/v) and placed in a tightly sealed flask for 12 h at room temperature. The solution is concentrated under reduced pressure, and the residue is purified by reverse phase HPLC. Fractions containing the desired 2'-O-TBS-protected N-[(2-dimethylamino)ethyl] phosphoramidate RNAs are collected and lyophilized. The residue is treated with a 1 M tetrabutylammonium fluoride solution in dry tetrahydrofuran for 24 h. A 0.05 M triethylammonium acetate buffer solution (pH 6.9) is added, and tetrahydrofuran is removed by evaporation. The residue is desalted with a Sep-Pak PLUS $tC_{18}$ cartridge, and purified by reverse phase HPLC to afford stereoregulated N-[(2-dimethylamino)ethyl]phosphoramidate RNAs.

Example 4

(a) General Procedure for the Solid-Phase Synthesis of X-phosphonate DNAs Using a class of Chiral Auxiliary Removable with Base (General Formula XI)

5'-O-(DMTr)nucleoside (0.5 μmnol) loaded to a HCP or CPG resin via a succinyl or oxalyl linker is used for the synthesis. Repeating the steps in Table 1 performs chain elongation. After the chain elongation, chiral auxiliaries are removed by treatment with an anhydrous 10% DBU solution in acetonitrile at room temperature for 15 min, and washed with acetonitrile. The 5'-O-DMTr group is then removed by treatment with 3% dichloroacetic acid in dichloromethane, and washed with dichloromethane. The oligomer on the HCP or CPG resin is then transferred into a screw-capped O-ring Eppendorf. The support containing 0.5 μmol of the oligonucleotide is suspended in 25% aqueous ammonia (1 mL) at 55° C. for 12 h to remove the protecting groups of the nucleobases and also to release the oligomer from the HCP or CPG resin. After centrifugation, the supernatant is removed in a round flask, and the support is washed with water (0.5 mL, twice). After centrifugation, the combined supernatants are concentrated under reduced pressure. The residue diluted in water (1 mL) is loaded onto a Sep-Pak PLUS $tC_{18}$ cartridge equilibrated in water. The column is first flushed with water (20 mL) to remove the salts. Then, the desalted stereoregulated X-phosphonate DNAs is eluted with 50% aqueous acetonitrile (10 mL) and analyzed by reverse phase UPLC and MALDI-TOF MS.

TABLE 1

| Step | Operation | Reagents and solvents | Time |
|---|---|---|---|
| 1 | Detritylation | 3% DCA/DCM | 3 × 30 s |
| 2 | Washing | (i) DCM (ii) dry MeCN (iii) drying in vacuo. 5M CMPT/MeCN (50 μL, 250 μmol) | — |
| 3 | Coupling | pre-activated ($R_P$)- or ($S_P$)-monomer solution (200 μL, 25 μmol)* | 5 min |
| 4 | Washing | (i) MeCN (ii) drying in vacuo. | — |
| 5 | Capping | (i) 0.5M CF$_3$COIm/dry THF (ii) 1M DMAN/dry THF | 30 s |
| 6 | Washing | (i) dry MeCN (ii) drying in vacuo. | — |
| 7 | Transformation | Sulfur electrophile, selenium electrophile, or borane agent | 5 min |
| 8 | Washing | (i) MeCN (ii) DCM | — |

A pre-activated ($R_P$)- or ($S_P$)-monomer solution is prepared as follows. 8-Diazabicyclo[5.4.0]undec-7-enium 5'-O-(DMTr)-2'-deoxynucleosid-3'-yl phosphonate (25 μmol) is dried by azeotropy with dry toluene, and then dissolved in dry acetonitrile-cyanomethylpyrrolidine (9:1, v/v). To the solution, triphenylphosphine dichloride (62.5 μmol) is added, and stirred for 10 min. Compound 8a, or 12a (30 μmol; Compound 8b, or 12b for "$S_P$" solution) is then added and stirred for additional 10 min to give a pre-activated monomer solution.

Example 5

(a) General Procedure for the Solid-Phase Synthesis of X-phosphonate RNAs Using a Class of Chiral Auxiliary Removal with a Base (General Formula XI)

5'-O-(DMTr)ribonucleoside (0.5 μmol) loaded to a HCP or CPG resin via a succinyl or oxalyl linker is used for the synthesis. Repeating the steps in Table 2 performs chain elongation. After the chain elongation, chiral auxiliaries are removed by treatment with an anhydrous 10% DBU solution in acetonitrile at room temperature for 15 min, and washed with acetonitrile. The 5'-O-DMTr group is removed by treatment with 3% dichloroacetic acid in dichloromethane and the resin is washed with dichloromethane. The oligomer on the HCP or CPG resin is then transferred into a screw-capped O-ring Eppendorf. The support containing 0.5 μmol of the oligonucleotide is suspended in 25% aqueous ammonia-ethanol (3:1, v/v) at room temperature for 48 h to remove the protecting groups of the nucleobases and also to release the oligomer from the HCP or CPG resin. After centrifugation, the supernatant is removed in a round flask, and the support is washed with water (0.5 mL, twice). After centrifugation, the combined supernatants are concentrated under reduced pressure, and the residue is purified by reverse phase HPLC. Fractions containing the desired 2'-O-TBS-protected X-phosphonate RNAs are collected and lyophilized. The residue is treated with a 1 M tetrabutylammonium fluoride solution in dry tetrahydrofuran for 24 h at room temperature. A 0.05 M triethylammonium acetate buffer solution (pH 6.9) is added, and tetrahydrofuran is removed by evaporation. The residue is desalted with a Sep-Pak PLUS tC$_{18}$ cartridge, and purified by reverse phase HPLC to afford stereoregulated X-phosphonate RNAs.

TABLE 2

| Step | Operation | Reagents and solvents | Time |
|---|---|---|---|
| 1 | Detritylation | 3% DCA/DCM | 3 × 30 s |
| 2 | Washing | (i) DCM (ii) dry MeCN (iii) drying in vacuo. 5M CMPT/MeCN (50 μL, 250 μmol) | — |
| 3 | Coupling | pre-activated (R$_P$)- or (S$_P$)-monomer solution (200 μL, 25 μ☐mol)* | 15 min |
| 4 | Washing | (i) MeCN (ii) drying in vacuo. | — |
| 5 | Capping | (i) 0.5M CF$_3$COIm/dry THF (ii) 1M DMAN/dry THF | 30 s |
| 6 | Washing | (i) dry MeCN (ii) drying in vacuo. | — |
| 7 | Transformation | Sulfur electrophile, selenium electrophile, or borane agent | 5 min |
| 8 | Washing | (i) MeCN (ii) DCM | — |

A pre-activated (R$_P$)- or (S$_P$)-monomer solution is prepared as follows. 8-Diazabicyclo[5.4.0]undec-7-enium 5'-O-(DMTr)-2'-O-(TBS)ribonucleosid-3'-yl phosphonate (25 μmol) is dried by azeotropy with dry toluene, and then dissolved in dry acetonitrile-N-cyanomethylpyrrolidine (9:1, v/v). To the solution, triphenylphosphine dichloride (62.5 μmol) is added, and stirred for 10 min. Compound 8a, 11a, 12a, or 15a (30 μmol; Compound 8b, 11b, 12b, or 15b for "S$_P$" solution) is then added and stirred for additional 10 min to give a pre-activated monomer solution.

INDUSTRIAL APPLICABILITY

Where a chiral auxiliary is introduced by using the compound represented by the general formula (I) or the compound represented by the general formula (XI) of the present invention, the reaction advances with a high asymmetric yield, the chiral auxiliary can be removed under a milder condition, and therefore a long chain nucleic acid derivative can be extremely efficiently prepared.

What is claimed is:

1. A nucleic acid derivative comprising a chiral auxiliary, wherein the chiral auxiliary is represented by formula (II) and binds to a phosphorus atom of a phosphite moiety of the nucleic acid derivative through the oxygen atom of the chiral auxiliary, wherein the squiggly line represents the point of attachment to a phosphorus atom of a phosphite moiety of the nucleic acid derivative:

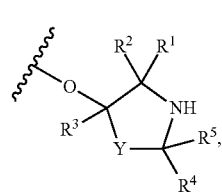

in which $R^1$ and $R^2$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

$R^3$ represents an unsubstituted or substituted aryl group or an unsubstituted or substituted alkyl group;

$R^4$ and $R^5$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

Y represents -$Y^1$-$Y^2$-, where $Y^1$ represents —C($R^6$)($R^7$)— in which $R^6$ and $R^7$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group, or $Y^1$ represents an unsubstituted or substituted o-aryldiyl group, and $Y^2$ represents a single bond or —C($R^8$)($R^9$)— in which $R^8$ and $R^9$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group.

2. The nucleic acid derivative of claim 1, wherein $R^3$ represents an unsubstituted or substituted aryl group.

3. The nucleic acid derivative of claim 2, wherein $Y^2$ represents a single bond.

4. The nucleic acid derivative of claim 1, wherein $Y^1$ represents an unsubstituted or substituted o-aryldiyl group.

5. A nucleoside-3'-phosphoramidite reagent represented by formula (IV):

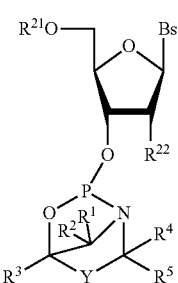

in which $R^1$ and $R^2$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

$R^3$ represents an unsubstituted or substituted aryl group or an unsubstituted or substituted alkyl group;

$R^4$ and $R^5$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

Y represents $-Y^1-Y^2-$, where $Y^1$ represents $—C(R^6)(R^7)—$ in which $R^6$ and $R^7$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group, or $Y^1$ represents an unsubstituted or substituted o-aryldiyl group, and $Y^2$ represents a single bond or $—C(R^8)(R^9)—$ in which $R^8$ and $R^9$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

$R^{21}$ represents a protective group of a hydroxyl group;

$R^{22}$ represents a hydrogen atom, an alkoxy group, a fluorine atom, or a protected hydroxyl group; and Bs represents a nucleobase.

6. The reagent of claim 5, wherein $R^3$ represents an unsubstituted or substituted aryl group.

7. The reagent of claim 5, wherein $Y^1$ represents an unsubstituted or substituted o-aryldiyl group.

8. The reagent of claim 7, wherein $Y^2$ represents a single bond.

9. A compound represented by formula (XI), or a salt thereof:

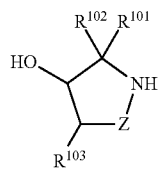

(XI)

in which $R^{101}$ and $R^{102}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

$R^{103}$ represents a cyano group, a halogen atom, a halogenated unsubstituted or substituted alkyl group, a substituted or unsubstituted halogenated alkanoyl group, a $C_1$-$C_6$ alkylsulfonyl group, a substituted or unsubstituted halogenated alkylsulfonyl group, or a nitro group;

Z represents $-Z^1-Z^2-$, in which $Z^1$ represents $—C(R^{104})(R^{105})—$ wherein $R^{104}$ and $R^{105}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group, and $Z^2$ represents a single bond or $—C(R^{106})(R^{107})—$ wherein $R^{106}$ and $R^{107}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group.

10. The compound or a salt thereof according to claim 9, wherein $R^{101}$ and $R^{102}$ are independently a hydrogen atom or an unsubstituted or substituted alkyl group, $R^{103}$ is a cyano group, and Z is $—C(R^{104})(R^{105})—$ wherein $R^{104}$ and $R^{105}$ are independently a hydrogen atom or an unsubstituted or substituted alkyl group.

11. The compound or a salt thereof of claim 9, wherein $R^{101}$ and $R^{102}$ are hydrogen atoms, $R^{103}$ is a cyano group, and Z is $—C(R^{106})(R^{105})—$ wherein $R^{104}$ and $R^{105}$ are hydrogen atoms.

12. The compound or a salt thereof of claim 9, wherein $R^{103}$ is a cyano group.

13. A nucleic acid derivative, wherein a chiral auxiliary represented by the following general formula (XII) binds to a phosphorus atom of a phosphite moiety of the nucleic acid derivative through the oxygen of the chiral auxiliary, wherein the squiggly line represents the point of attachment to a phosphorus atom of a phosphite moiety of the nucleic acid derivative:

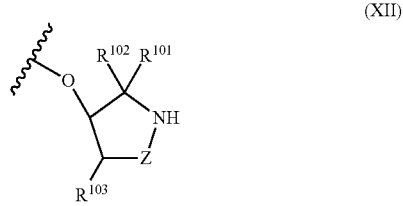

(XII)

in which $R^{101}$ and $R^{102}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

$R^{103}$ represents a cyano group, a halogen atom, a halogenated unsubstituted or substituted alkyl group, a substituted or unsubstituted halogenated alkanoyl group, a $C_1$-$C_6$ alkylsulfonyl group, a substituted or unsubstituted halogenated alkylsulfonyl group, or a nitro group; and Z represents $-Z^1-Z^2-$, in which $Z^1$ represents $—C(R^{104})(R^{105})—$ wherein $R^{104}$ and $R^{105}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group, and $Z^2$ represents a single bond or —C(R$^{106}$)(R$^{107}$)— wherein R$^{106}$ and R$^{107}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group.

14. The nucleic acid derivative of claim 13, wherein R$^{103}$ is a cyano group.

15. The nucleic acid derivative of claim 14, wherein R$^{101}$ and R$^{102}$ are independently a hydrogen atom or an unsubstituted or substituted alkyl group, and Z is —C(R$^{104}$)(R$^{105}$)— wherein R$^{104}$ and R$^{105}$ are independently a hydrogen atom or an unsubstituted or substituted alkyl group.

16. The nucleic acid derivative of claim 14, wherein R$^{101}$ and R$^{102}$ are hydrogen atoms, and Z is —C(R$^{104}$)(R$^{105}$)— wherein R$^{104}$ and R$^{105}$ are hydrogen atoms.

17. A nucleoside-3'-phosphoramidite reagent represented by formula (XIV):

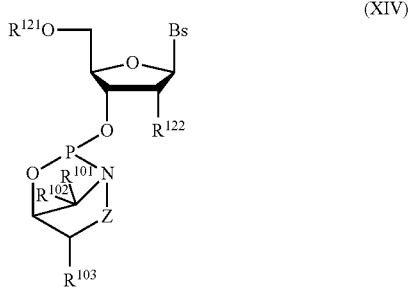

in which R$^{101}$ and R$^{102}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

R$^{103}$ represents a cyano group, a halogen atom, a halogenated unsubstituted or substituted alkyl group, a substituted or unsubstituted halogenated alkanoyl group, a $C_1$-$C_6$ alkylsulfonyl group, a substituted or unsubstituted halogenated alkylsulfonyl group, or a nitro group;

Z represents -Z$^1$-Z$^2$-, in which Z$^1$ represents —C(R$^{104}$)(R$^{105}$)— wherein R$^{104}$ and R$^{105}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group, and Z$^2$ represents a single bond or —C(R$^{106}$)(R$^{107}$)— wherein R$^{106}$ and R$^{107}$ independently represent a hydrogen atom, an unsubstituted or substituted alkyl group, an unsubstituted or substituted alkenyl group, an unsubstituted or substituted alkynyl group, an unsubstituted or substituted alkoxy group, an unsubstituted or substituted aralkyl group, or an unsubstituted or substituted aryl group;

R$^{121}$ represents a protective group of a hydroxyl group;

R$^{122}$ represents a hydrogen atom, an alkoxy group, a fluorine atom, or a protected hydroxyl group; and Bs represents a nucleobase.

18. The nucleoside of claim 17, wherein R$^{103}$ is a cyano group.

19. The nucleoside of claim 18, wherein R$^{101}$ and R$^{102}$ are independently a hydrogen atom or an unsubstituted or substituted alkyl group, and Z is —C(R$^{104}$)(R$^{105}$)— wherein R$^{104}$ and R$^{105}$ are independently a hydrogen atom or an unsubstituted or substituted alkyl group.

20. The nucleoside of claim 18, wherein R$^{101}$ and R$^{102}$ are hydrogen atoms, and Z is —C(R$^{104}$)(R$^{105}$)— wherein R$^{104}$ and R$^{105}$ are hydrogen atoms.

* * * * *